US006902907B1

(12) United States Patent
Tsui et al.

(10) Patent No.: US 6,902,907 B1
(45) Date of Patent: Jun. 7, 2005

(54) CYSTIC FIBROSIS GENE

(75) Inventors: Lap-Chee Tsui, Toronto (CA); John R. Riordan, Toronto (CA); Francis S. Collins, Ann Arbor, MI (US); Johanna M. Rommens, Willowdale (CA); Michael C. Iannuzzi, Ann Arbor, MI (US); Bat-Sheva Kerem, Toronto (CA); Mitchell L. Drumm, Ann Arbor, MI (US); Manuel Buchwald, Toronto (CA)

(73) Assignees: HSC Research Development Corporation, Toronto (CA); The Board of Regents Acting for and on Behalf of The University of Michigan, Ann Arbor, MI (US)

(*) Notice: Subject to any disclaimer, the term of this patent is extended or adjusted under 35 U.S.C. 154(b) by 0 days.

(21) Appl. No.: 08/252,778

(22) Filed: Jun. 2, 1994

Related U.S. Application Data

(60) Division of application No. 08/123,864, filed on Sep. 20, 1993, now abandoned, which is a continuation of application No. 07/401,609, filed on Aug. 31, 1989, now abandoned, which is a continuation-in-part of application No. 07/399, 945, filed on Aug. 24, 1989, now abandoned, which is a continuation-in-part of application No. 07/396,894, filed on Aug. 22, 1989, now abandoned.

(51) Int. Cl.[7] .......................... C12P 21/06; C07K 14/00
(52) U.S. Cl. ................ 435/69.1; 435/252.3; 435/320.1; 435/325; 536/23.1; 530/350
(58) Field of Search ............................ 435/69.1, 320.1, 435/252.3, 325, 70.1, 240.1; 536/23.1; 530/350

(56) References Cited

U.S. PATENT DOCUMENTS

| 4,322,274 A | 3/1982 | Wilson et al. ........... 204/180 G |
| 4,844,893 A | 7/1989 | Honsik et al. ............. 424/85.8 |
| 4,847,201 A | 7/1989 | Kaswasaki et al. ........... 435/70 |
| 4,853,331 A | 8/1989 | Herrnstadt et al. ....... 435/252.1 |
| 4,861,589 A | 8/1989 | Ju .............................. 424/93 |
| 4,861,719 A | 8/1989 | Miller ........................ 435/236 |
| 4,868,116 A | 9/1989 | Morgan et al. .......... 435/240.2 |
| 4,980,286 A | 12/1990 | Morgan et al. .......... 435/172.3 |
| 5,240,846 A | 8/1993 | Collins et al. ........... 435/240.1 |
| 5,407,796 A | * 4/1995 | Cutting et al. ................ 435/6 |

FOREIGN PATENT DOCUMENTS

| EP | 0 226 288 | 6/1987 | .................... 1/68 |
| EP | 0 288 299 | 10/1988 | .................... 1/68 |
| EP | 0 446 017 | 9/1991 | .................... 5/12 |
| GB | 2 203 742 | 10/1988 | .................... 21/4 |
| WO | WO 91/02796 | 3/1991 | .................... 15/12 |
| WO | WO 91/10734 | 7/1991 | .................... 15/12 |
| WO | WO 92/05252 | 4/1992 | .................... 15/12 |
| WO | WO 92/05273 | 4/1992 | .................... 21/6 |
| WO | WO 93/17040 | 9/1993 | |
| WO | WO 94/12649 | 9/1994 | .................... 15/86 |

OTHER PUBLICATIONS

Drumm et al., Correction of the Cystic Fibrosis Defect in Vitro by Retrovirus–Mediated Gene Transfer, *Cell* 62:1227–1233 (1990).

Bear et al., Purification and Functional Reconstitution of the Cystic Fibrosis Transmembrane Conductance Regulator (CFTR), *Cell* 68:809–818 (1992).

Dean et al., Multiple Mutations in Highly Conserved Residues are Found in Mildly Affected Cystic Fibrosis Patients, *Cell* 61:863–870 (1990).

Cutting et al., A Cluster of Cystic Fibrosis Mutations in the First Nucleotide–Binding Fold of the Cystic Fibrosis Conductance Regulator Protein, *Nature* 346:366–369 (1990).

Rommens et al., cAMP–Inducible Chloride Conductance in Mouse Fibroblast Lines Stably Expressing the Human Cystic Fibrosis Transmembrane Conductance Regulator, *Proc. Natl. Acad. Sci. USA* 88:7500–7504 (1991).

Kartner et al., Expression of the Cystic Fibrosis Gene in Non–Epithelial Invertebrate Cells Produces a Regulated Anion Conductance, *Cell* 64:681–691 (1991).

Zielenski et al., Genomic DNA Sequence of the Cystic Fibrosis Transmembrane Conductance Regulator (CFTR) Gene, *Genomics* 10:214–228 (1991).

Kerem et al., Identification of Mutations in Regions Corresponding to the Two Putative Nucleotide (ATP)–Binding Folds of the Cystic Fibrosis Gene, *Proc. Natl. Acad. Sci. USA* 87:8447–8451 (1990).

White et al., A Frame–Shift Mutation in the Cystic Fibrosis Gene, *Nature* 344:665–667 (1990).

Hyde et al., Structural Model of ATP–Binding Proteins Associated with Cystic Fibrosis, Multidrug Resistance and Bacterial Transport, *Nature* 346:362–365 (1990).

Quinton, P.M., Cystic Fibrosis: A Diseasse in Electrolyte Transport, *FASEB J.* 4:2709–2717 (1990).

Frizzell, R.A., Cystic Fibrosis: A Disease of Ion Channels, *TINS* 10(5):190–193 (1987).

Landry et al., Purification and Reconstitution of Chloride Channels from Kidney and Trachae, *Science* 244:1469–1472 (1989).

Jensen et al., Chloride Channel Expression in Cultures of Sweat Gland Epithelial Cells in Cystic Fibrosis, *J. Cell. Biol.* 107(6):139a, Abstract No. 788 (1989).

Orr et al., In Vivo and In Vitro Phosphorylation of Apical Membrane Proteins of the T–84 Colonic Epithelial Cell Line, *J. Cell Biol.* 107(6):493a, Abstract No. 2776 (1989).

(Continued)

Primary Examiner—Karen Cochrane Carlson
(74) Attorney, Agent, or Firm—Sterne, Kessler, Goldstein & Fox P.L.L.C.

(57) ABSTRACT

The cystic fibrosis gene and its gene product are described for both the normal and mutant forms. The genetic and protein information is used in developing DNA diagnosis, protein diagnosis, carrier and patient screening, drug and gene therapy, cloning of the gene and manufacture of the protein, and development of cystic fibrosis affected animals.

14 Claims, 36 Drawing Sheets

OTHER PUBLICATIONS

Welsh, M.J., Abnormal Regulation of Ion Channels in Cystic Fibrosis Epithelial, *FASEB J. 4*:2718–2725 (1990).

Willumsen et al., Activation of an Apical Cl⁻ Conductance by $Ca^{2+}$ Ionophores in Cystic Fibrosis Airway Epithelia, *Am. J. Physiol. 256*:C226–C233 (1989).

Schoumacher et al., Phosphorylation Fails to Activate Chloride Channels from Cystic Fibrosis Airway Cells, *Nature 330*:752–754 (1987).

Venglarik et al., A Simple Assay for Agonist–Regulated Cl and K Conductances in Salt–Secreting Epithelial Cells, *Am. J. Physiol. 259*:C358–C364 (1990).

Scholte et al., Immortalization of Nasal Polyp Epithelial Cells from Cystic Fibrosis Patients, *Experimental Cell Research 182*:559–571 (1989).

Welsh et al., Chloride and Potassium Channels in Cystic Fibrosis Airway Epithelia, *Nature 322*:467–470 (1986).

Stutts et al., Chloride Uptake into Cultured Airway Epithelial Cells from Cystic Fibrosis Patients and Normal Individuals, *Proc. Natl. Acad. Sci. USA 82*:6677–6681 (1985).

Yankaskas et al., Culture of Human Nasal Epithelial Cells on Collagen Matrix Supports, *Am. Rev. Respir. Dis. 132*:1281–1287 (1985).

Jetten et al., Persistence of Abnormal Chloride Conductance Regulation in Transformed Cystic Fibrosis Epithelia, *Science 244*:1472–1475 (1989).

Widdicombe et al., Cystic Fibrosis Decreases the Apical Membrane Chloride Permeability of Monolayers Cultured from Cells of Tracheal Epithelium, *Proc. Natl. Acad. Sci. USA 82*:6167–6171 (1985).

Li et al., Cyclic AMP–Dependent Protein Kinase Opens Chloride Channels in Normal but not Cystic Fibrosis Airway Epithelium, *Nature 331*:358–360 (1988).

Cliff et al., Separate Cl⁻ Conductances Activated by cAMP and $Ca^{2+}$ in Cl⁻–Secreting Epithelial Cells, *Proc. Natl. Acad. Sci. USA 87*:4956–4960 (1990).

Frizzell et al., Altered Regulation of Airway Epithelial Cell Chloride Channels in Cystic Firosis, *Science 233*:558–560 (1986).

Boucher et al., Na⁺ Transport in Cystic Fibrosis Respiratory Epithelia, *J. Clin. Invest. 78*:1245–1252 (1986).

Sato et al., Defective Beta Adrenergic Response of Cystic Fibrosis Sweat Glands In Vivo and In Vitro, *J. Clin. Invest. 73*:1763–1771 (1984).

Reddy et al., Lack of β–Adenergic Responsiveness in Cells Cultured from Reabsorptive Sweat Ducts of Cystic Fibrosis (CF) Subjects, *Pediatric Pulmonology Supp. 1*:115 Abstract No. 31 (1987).

Reddy et al., Retention of Basic Electrophysiologic Properties by Human Sweat Duct Cells in Primary Culture, *In Vitro Cellular & Developmental Biology 24(9)*:905–910 (1988).

Riordan et al., Utilization of Cultured Epithelial Cells from the Sweat Gland in Studies of the CF Defect in Genetics and Epithelial Cell Dysfunction in Cystic Fibrosis, Alan R. Liss, Inc., pp. 59–71 (1987).

Riordan et al., Molecular Studies of Cultured Epithelial Cells from the Sweat Gland in Cellular and Molecular Basis of Cystic Fibrosis, (G. Mastella and P.M. Quinton, Eds.) San Francisco Press, Inc., San Francisco, CA, pp. 416–424 (1988).

Reddy et al., Electrical Properties of Cultured Reabsorptive Sweat Duct Cells from Normal and Cystic . . . in Cellular Molecular Basis of Cystic Fibrosis (G. Mastella and P.M. Quinton, Eds.) San Francisco Press, Inc., San Francisco, CA, pp. 383–393 (1988).

Collie et al., Culture of Sweat Gland Epithelial Cells from Normal Individuals and Patients with Cystic Fibrosis, *In Vitro Cellular & Developmental Biology 21(10)*:597–602 (1985).

Cheng et al., Increased Sulfation of Glycoconjugates by Cultured Nasal Epithelial Cells from Patients with Cystic Fibrosis, *J. Clin. Invest. 84*:68–72 (1989).

Boat et al., Human Respiratory Tract Secretions, *Archives of Biochemistry and Biophysics 177*:95–104 (1976).

Corey et al., Familial Concordance of Pancreatic Function in Cystic Fibrosis, *Journal of Pediatrics 115(2)*:274–277 (1989).

Harris et al., Establishment of a Tissue Culture System for Epithelial Cells Derived from Human Pancreas: A Model for the Study of Cystic Fibrosis, *Journal of Cell Science 87*:695–703 (1987).

Schoumacher et al., A Cystic Fibrosis Pancreatic Adenocarcinoma Cell Line, *Proc. Natl. Acad. Sci. USA 87*:4012–4016 (1990).

Chen et al., A cAMP–Regulated Chloride Channel in Lymphocytes That is Affected in Cystic Fibrosis, *Science 243*:657–660 (1989).

Tabcharani et al., Bicarbonate Permeability of the Outwardly Rectifying Anion Channel, *J. Membrane Biol. 112*:109–122 (1989).

The Cystic Fibrosis Genetic Analysis Consortium, Worldwide Survey of the ΔF508 Mutation–Report from the Cystic Fibrosis Genetic Analysis Consortium, *Am J. Hum. Genet. 47*:354–359 (1990).

Riordan et al., Identification of the Cystic Fibrosis Gene: Cloning and Characterization of Complementary DNA, *Science 245*:1066–1073 (1989).

Rommens et al., Identification of the Cystic Fibrosis Gene: Chromosome Walking and Jumping, *Science 245*:1059–1065 (1989).

Kerem et al., Identification of the Cystic Fibrosis Gene: Genetic Analysis, *Science 245*:1073–1080 (1989).

Mark, J.L., The Cystic Fibrosis Gene is Found, *Science 245*:923–925 (1989).

Koshland, D.E., Jr., The Cystic Fibrosis Gene Story, *Science 245(4922)*:1029 (1989).

Fulton et al., A 12 Megabase Restriction Map at the Cystic Fibrosis Locus, *Nucleic Acids Research 17(1)*:271–284 (1989).

Green et al., Chromosomal Region of the Cystic Fibrosis Gene in Yeast Artificial Chromosomes: A Model for Human Genome Mapping, *Science 250*:94–98 (1990).

Dean et al., Approaches to Localizing Disease Genes as Applied to Cystic Fibrosis, *Nucleic Acids Research 18(2)*:345–350 (1989).

Kerem et al., DNA Marker Haplotype Association with Pancreatic Sufficiency in Cystic Fibrosis, *Am. J. Hum. Genet. 44*:827–834 (1989).

Rommens et al., Physical Localization of Two DNA Markers Closely Linked to the Cystic Fibrosis Locus by Pulsed–Field Gel Electrophoresis, *Am. J. Hum. Genet. 45*:932–941 (1989).

Estivill et al., A Candidate for the Cystic Fibrosis Locus Isolated by Selection for Methylation–Free Islands, *Nature* 326:840–845 (1987).

Iannuzzi et al., Isolation of Additional Polymorphic Clones from the Cystic Fibrosis Region, Using Chromosome Jumping from D7S8, *Am. J. Hum. Genet.* 44:695–703 (1989).

Tsue et al., Progress Towards Cloning the Cystic Fobrosis Gene, *Phil. Trans. R. Soc. Lond. B319*:263–273 (1988).

Poustka et al., A Long–Range Restriction Map Encompassing the Cystic Fibrosis Locus and Its Closely Linked Genetic Markers, *Genomics* 2:337–345 (1988).

Dean, M., Molecular and Genetic Analysis of Cystic Fibrosis, *Genomics* 3:93–99 (1988).

Rommens et al., Identification and Regional Localization of DNA Markers on Chromosome 7 for the Cloning of the Cystic Fibrosis Gene, *Am. J. Hum. Genet.* 43:645–663 (1988).

Rommens et al., Genetic and Physical Mapping of the Chromosomal Region Containing the Cystic Fibrosis Locus, *Am. J. Hum. Genetics 43(3 Suppl.)*:A199 (1988).

Drumm et al., Physical Mapping of the Cystic Fibrosis Region by Pulsed–Field Gel Electrophoresis, *Genomics* 2:346–354 (1988).

Collins et al., Construction of a General Human Chromosome Jumping Library, with Application to Cystic Firosis, *Science* 235:1046–1049 (1987).

Farrall et al., Recombinations Between IRP and Cystic Fibrosis, *Am. J. Hum. Genet.* 43:471–475 (1988).

Wahl et al., Cosmid Vectors for Rapid Genomic Walking, Restriction Mapping, and Gene Transfer, *Proc. Natl. Acad. Sci. USA* 84:2160–2164 (1987).

Buchwald et al., Current Status of the Genetics of Cystic Fibrosis in Genetics and Epithelial Cell Dysfunction in Cystic Fibrosis (Alan R. Liss, Inc.), pp. 19–29 (1987).

Buchwald et al., The Genetics of Cystic Fibrosis—Mid 1987, *Excerta Med. Asia Pacific Congress* 74:3–9 (1987).

Tsui et al., Progress Towards Cloning of the Cystic Fibrosis Gene—Identification of New DNA Markers in the 7Q31 Region, *Protides of the Biological Fluids* 35:51–54 (1987).

Riordan, J., Reaching Between the Functional and Genetic Defects in Cystic Fibrosis, *Pediatric Pulmonology Suppl.* 1:29 (1987).

Zengerling et al., Mapping of DNA Markers Linked to the Cystic Fibrosis Locus on the Long Arm of Chromosome 7, *Am. J. Hum. Genet.* 40:228–236 (1987).

Lathrop et al., Refined Linkage Map of Chromosome 7 in the Region of the Cystic Fibrosis Gene, *Am. J. Hum. Genet.* 42:038–044 (1988).

Spence et al., Linkage of DNA Markers to Cystic Fibrosis in 26 Families, *Am. J. Hum. Genet.* 39:729–734 (1986).

Michiels et al., Derivation of Clones Close to met by Preparative Field Inversion of Gel Electrophoresis, *Science* 236:1305–1308 (1987).

Tsui et al., Genetic Analysis of Cystic Fibrosis Using Linked DNA Markers, *Am. J. Hum. Genet.* 39:720–728 (1986).

Estivill et al., Patterns of Polymorphism and Linkage Disequilibrium for Cystic Fibrosis, *Genomics* 1:257–263 (1987).

Estivill et al., Isolation of a New DNA Marker in Linkage Disequilibrium with Cystic Fibrosis, Situated Between J3.11 (D7S8) and IRP, *Am. J. Hum. Genet.* 44:704–710 (1989).

Beaudet et al., Linkage of Cystic Fibrosis to Two Tightly Linked DNA Markers: Joint Report from a Collaborative Study, *Am. J. Hum. Genet.* 39:681–693 (1986).

Scambler et al., Chromosome Mediated Gene Transfer of Six DNA Markers Linked to the Cystic Fibrosis Locus on Human Chromosome Seven, *Nucleic Acids Res.* 14:7159–7174 (1986).

White et al., A Closely Linked Genetic Marker for Cystic Fibrosis, *Nature* 318:382–384 (1985).

Wainwright et al., Localization of Cystic Fibrosis Locus to Human Chromosome 7cen–q22, *Nature* 318:384–385 (1985).

Tsui et al., Mapping of the Cystic Fibrosis Locus on Chromosome 7, *Cold Spring Harbor Symp. Quant. Biol. LI*:325–335 (1986).

Schmiegelow et al., Linkage Between the Loci for Cystic Fibrosis and Paraoxonase, *Clinical Genetics* 29:374–377 (1986).

Buchwald et al., Linkage of Cystic Fibrosis to the pro$\alpha$2(I) Collagen Gene, COL1A2, on Chromosome 7, *Cytogenet. Cell Genet.* 41:234–239 (1986).

Tsui et al., Cystic Fibrosis Locus Defined by a Genetically Linked Polymorphic DNA Marker, *Science* 230:1054–1057 (1985).

Knowlton et al., A Polymorphic DNA Marker Linked to Cystic Fibrosis is Located on Chromosome 7, *Nature* 318(*6044*):380–382 (1985).

Tsui et al., Cystic Fibrosis: Progress in Mapping the Disease Locus Using Polymorphic DNA Markers. I., *Cytogenet. Cell Genet.* 39:299–301 (1985).

Taussig, L.M., Cystic Fibrosis: An Overview, *Cystic Fibrosis* (Taussig, L.M., ed.) Thieme–Stralton, N.Y., N.Y., pp. 1–9 (1984).

Boat et al., Cystic Fibrosis in The Metabolic Basis of Inherited Disease, vol. II, (Scriver et al., eds.) McGraw–Hill Information Services Company, N.Y., N.Y., pp. 2649–2679 (1989).

Smith et al., Cystic Fibrosis: Diagnostic Testing and the Search for the Gene, *Clin. Chem.* 35/7(*B*):B17–B20 (1989).

Dodge, J.A., Implications of the New Genetics for Screening for Cystic Fibrosis, *The Lancet*:672–673 (1988).

Beaudet et al., Linkage Disequilibrium, Cystic Fibrosis and Genetic Counseling, *Am. J. Hum. Genet.* 44:319–326 (1989).

Beaudet et al., Prenatal Diagnosis of Cystic Fibrosis, *J. Ped.* 111:630–633 (1987).

Brock, D.J.H., Amniotic Fluid Alkaline Phosphatase Isoenzymes in Early Prenatal Diagnosis of Cystic Fibrosis, *The Lancet*, pp. 941–943 (1983).

Wilson et al., Correction of CD18–Deficient Lymphocytes by Retrovirus–Mediated Gene Transfer, *Science* 248:1413–1416 (1990).

Wilson et al., Expression of Human Adenosine Deaminase in Mice Reconstituted with Retrovirus–Transduced Hematopoietic Stem Cells, *Proc. Natl. Acad. Sci. USA* 87:439–443 (1990).

Korman et al., Expression of Human Class II Major Histocompatibility Complex Antigens Using Retrovirus Vectors, *Proc. Natl. Acad. Sci. USA* 84:2150–2154 (1987).

Wilson et al., Correction of the Genetic Defect in Hepatocytes from the Watanabe Heritable Hyperlipidemic Rabbit, *Proc. Natl. Acad. Sci. USA* 85:4421–4425 (1988).

Short et al., $\lambda$ ZAP: A Bacteriophage $\lambda$ Expression Vector with In Vivo Excision Properties, *Nucleic Acids Research* 16(*15*):7583–7600 (1988).

Slot et al., No Evidence for Expression of the Insulin–Regulatable Glucose Transporter in Endothelial Cells, *Nature* *346*:369–371 (1990).

Smith, M., In Vitro Mutagenesis, *Ann. Rev. Genet.* *19*:423–462 (1985).

Feinberg et al., A Technique for Radiolabeling DNA Restriction Enconuclease Fragments to High Specific Activity, *Analytical Biochemistry 132*:6–13 (1983).

Sanbrook et al., Oligonucleotide–Mediated Mutagenesis in Molecular Cloning, A Laboratory Manual, 2nd Ed., Cold Spring Harbor Press, Cold Spring Harbor, NY, pp. 15.51–15.80 (1989).

Meakin et al., γ–Crystallins of the Human Eye Lens: Expression Analysis of Five Members of the Gene Family, *Molecular and Cellular Biology 7(8)*:2671–2679 (1987).

* cited by examiner

```
          V  T  A  F  W  E  E G F  G  E  L  F  E  K  A  K  Q  N  N
1321 GTAACAGCCTTCTGGGAGGAGGATTGGGAATTATTTGAGAAGCAAAACAAAACAAT         416
                 o
          N  N  R  K  T  S  N  G  D  D  S  L  F  F  S  N  F  S  L  L
1381 AACAATAGAAAAACTTCTAATGGTGATGACAGCCTCTTCTTCAGTAATTTCTCACTTCTT      436

G  T  P  V  L  K  D  I  N  F  K  I  E  R  G  Q  L  L  A  V
1441 GGTACTCCTGTCCTGAAAGATATTAATTTCAAGATAGAAAGAGGACAGTTGTTGGCGGTT      456

A  G  S  T  G  A  G  K T  S  L  L  M  M  I  M  G  E  L  E
1501 GCTGGATCCACTGGAGCAGGCAAGACTTCACTTCTAATGATGATTATGGGAGAACTGGAG      476

P  S  E  G  K  I  K  S  G  R  I  S  F  C  S  Q  F  S  W
1561 CCTTCAGAGGGTAAAATTAAGCACAGTGGAAGAATTTCATTCTGTTCTCAGTTTCCTGG      496
                         •
          I  M  P  G  T  I  K  E  N  I  I △ F  G  V  S  Y  D  E  Y  R
1621 ATTATGCCTGGCACCATTAAAGAAAATATCATCTTTGGTGTTTCCTATGATGAATATAGA     516

Y  R  S  V  I  K  A  C  Q  L  E E D  I  S  K  F  A  E  K
1681 TACAGAAGCGTCATCAAAGCATGCCAACTAGAAGAGGACATCTCCAAGTTTGCAGAGAAA     536

D  N  I  Y  L  G  E  G  G  I  T  L  S  G  G  Q  R  A  R  I
1741 GACAATATATAGTTCTTGGAGAAGGTGGAATCACACTGAGTGGAGGTCAACGAGCAAGAATT   556

S  L  A  R  A  V  Y  K  D  A  D  L  Y  L  L  D  S  P  F  G
1801 TCTTTAGCAAGAGCAGTATACAAAGATGCTGATTTGTATTATTAGACTCCTTTGGA         576
                         •
          Y  L  D  V  L  T  E  K  E  I  F  E  S  C  V  C  K  L  M  A
1861 TACCTAGATGTTTTAACAGAAAAAGAAATATTTGAAAGCTGTGTCTGTAAACTGATGGCT     596
```

FIG. 1C

```
             N  K  T  R  I  L  V  T  S  K  M  E  H  L  K  K  A  D  K  I
1921  AACAAAACTAGGATTTGGTCACTTCTAAAATGGAACATTTAAAGAAAGCTGACAAAATA              616

L  I  L  H  E  G  S  S  Y  F  Y  G  T  F  S  E  L  Q  N  L
1981  TTAATTTGCATGAAGGTAGCAGCTATTTTTATGGGACATTTTCAGAACTCCAAAATCTA              636

Q  P  D  F  S  K  L  M  G  C  D  S  F  D  Q  F  S  A  E
2041  CAGCCAGACTTTAGCTCAAAACTCATGGGATGTGATTCTTTCGACCAATTTAGTGCAGAA             656

R  R  N  S  I  L  T  E  T  L  H  R  F  S  L  E  G  D  A  P
2101  AGAGCCAGAATTCAATCCTAACTGAGACCCTTCACCGTTTCTCATTAGAAGGAGATGCTCCT            676

V  S  W  T  E  T  K  K  Q  S  F  K  Q  T  G  E  F  G  E  K
2161  GTCCTGGACAGAAACAAAAAACAATCTTTAAACAGACTGGAGAGTTTGGGGAAAAA                  696

R  K  N  S  I  L  N  P  I  N  S  I  R  K  F  S  I  V  Q  K
2221  AGGAAGAATTCAATTCTATTCTCAATCAACTCTATACGAAAATTTCCATTGTGCAAAAG              716

T  P  L  Q  M  N  G  I  E  E  D  S  D  E  P  L  E  R  R  L
2281  ACTCCCTTACAAATGAATGGCATCGAAGAGGATTCTGATGAGCCTTTAGAGAGAAGGCTG             736

S  L  V  P  D  S  E  Q  G  E  A  I  L  P  R  I  S  V  I  S
2341  TCCTTAGTACCAGATTCTGAGCAGGGAGAGGCGATACTGCCTCGCATCAGCGTGATCAGC              756

T  G  P  T  L  Q  A  R  R  Q  S  V  L  N  L  M  H  S
2401  ACTGGCCCCACGCTTCAGGCACGAAGGCAGTCTGTCCTGAACCTGATGACACTCA                   776

V  N  Q  Q  N  I  H  R  K  T  A  S  T  R  K  V  S  L
2461  GTTAACCAAGTCAGAACATTCACCGAAAGACCATCCACACGAAAAGTGTCACTG                    796

A  P  Q  A  N  L  T  E  L  D  I  Y  S  R  R  L  S  Q  E  T
2521  GCCCCTCAGGCAAACTTGACTGAACTGGATATATATTCAAGAAGGTTATCTCAAGAAACT              816
```

FIG.1D

```
        G  L  E  I  S  E  E  I  N  E  E  D  L  K  E  C  F  F  D  D       836
2581  GGCTTGGAAATAAGTGAAGAAATTAACGAAGAAGAGTTAAAGGAGTGCTTTTTGATGAT

M  E  S  I  P  A  V  T  T  W  N  T  Y  L  R  Y  I  T  V  H       856
2641  ATGGAGAGCATACCAGCAGTGACTACATGGAACACATACCTTCGATATATTACTGTCCAC

K  S  L  F  Y  L  W  C  L  Y  I  F  L  A  E  V  A  A            876
2701  AAGAGCTTAATTTTTGTGCTTAGTAATTTGGTGCTTAGTAATTTCTGGCAGAGGTGCTGCT

S  L  V  L  N  G  M  T  P  L  Q  D  D  K  G  N  S  T            896
2761  TCTTTGGTTGTGCTGGCTCCTTGGCTAAATACTCCTCTTCAAGACAAAGGAATAGTACT

H  S  R  N  N  S  Y  A  V  I  I  T  S  T  S  S  Y  Y  V  F       916
2821  CATAGTAGAAATAACAGTTATGCAGTGATTATCACCAGTCGTCGTATTATGTGTTT

Y  I  Y  G  Y  A  D  T  L  A  M  G  F  F  R  G  L  P            936
2881  TACATTTACGTGGGAGTAGCCGACACTTTGCTTGCTATGGGATTCTTCAGAGGTCTACCA

L  V  H  T  L  T  T  V  S  K  I  L  H  K  M  L  H  S  V          956
2941  CTGGTTCATACACTCTAATCACAGTGTCGAAAATTTTACACCACAAAATGTTACATTCTGTT

L  Q  A  P  H  S  T  L  N  T  L  K  A  G  I  L  N  R  F          976
3001  CTTCAAGCACCTATGTCAACCCTCAACACGTTGAAGCAGTGGGATTCTTAATAGATTC

S  K  D  I  A  I  L  D  D  L  L  P  L  T  I  D  F  I  Q          996
3061  TCCAAAGATATAGCAATTTGGATGACCTTCTCGCCTCTACCATATTTGACTTCATCCAG

L  L  I  V  I  G  A  I  A  V  V  A  V  L  Q  P  Y  I  F        1016
3121  TTGTTATTAATTGTGATTGGAGCTATAGCAGTGTGCAGTTTACAACCCTACATCTTT

V  A  T  V  P  Y  V  A  F  I  M  L  R  A  Y  F  L  Q  T        1036
3181  GTTGCAACAGTGCCAGTAGTGGCTTTATTATGTTGAGAGCATATTTCCTCCAAACC
```

FIG. 1E

| Pos | Amino acid sequence | Nucleotide sequence | # |
|---|---|---|---|
| 3241 | S Q Q L K Q L E S E G R S P I F T H L V | TCACAGCAACTCAAACAACTGAAGTCAGGAGTCCAATTTCACTCATCTTGTT | 1056 |
| 3301 | T S L K G L H T L R A F G R Q P Y F E T | ACAAGCTTAAAAGGACTATGGACACTTCGTGCTTTTGGACGGCAGCCTTACTTTGAAACT | 1076 |
| 3361 | L F H K A L N L H T A N W F L Y L S T L | CTGTTCCACAAAGCTCTGAATTTACATACTGCCAACTGGTTCTTGTACCTGTCAACACTG | 1096 |
| 3421 | R N F Q M R I E M I F V I F F I A V T F | CGCTGGTTCCAAATGAGAATAGAAATGATTTTTGTCATCTTCTTCATTGCTGTTACCTTC | 1116 |
| 3481 | I S I L T T G E G E G R V G I L L T L A | ATTTCCATTTTAACAACAGGAGAAGGAGAAGGTAGAGTTGGTATTCTGACTTTAGCC | 1136 |
| 3541 | H N I M S T L Q H A Y N S S I D V D S L | ATGAATATCATGAGTACATTGCAGTGGGCTGTAAACTCCAGCATAGATGTGGATAGCTTG | 1156 |
| 3601 | M R S V S R V F K F I D H P T E G K P T | ATGCGATCTGTGAGCCGAGTCTTTAAGTTCATTGACCATCCAACAGAAGGTAAACCTACC | 1176 |
| 3661 | K S T K P Y K N G Q L S K V M I I E N S | AAGTCAACCAAACCATACAAGAATGGCCAACTCTCGAAAGTTATGATTATTGAGAATTCA | 1196 |
| 3721 | H V K K D D I W P S G G Q M T V K D L T | CACGTGAAGAAAGATGACATCTGGCCCTCAGGGGGCCAAATGACTGTCAAAGATCTCACA | 1216 |
| 3781 | A K Y T E G G N A I L E N I S F S I S P | GCAAAATACACAGAAGGTGGAAATGCCATATTAGAAAACATTTCCTTCTCAATAAGTCCT | 1236 |
| 3841 | G Q R V G L L G R T G S G K S T L L S A | GGCCAGAGGGTGGGCCTCTTGGGAAGAACTGGATCAGGAAGAGTACTTTGTTATCAGCT | 1256 |

FIG. 1F

```
       F  L  R  L  N  T  E  G  E  I  Q  I  D  G  V  S  W  D  S
3901   TTTTGAGACTACTGAACACTGAAGGAGAAATCCAGATCGATGGTGTCTTGGGATTCA    1276
       I  T  L  Q  Q  W  R  K  A  F  G  V  I  P  Q  K  V  F  I  E
3961   ATAACTTGCAACAGTGGAGGAAAGCCTTTGGAGTGATACCACAGAAAGTATTTATTTT    1296
       S  G  T  F  R  K  N  L  D  P  Y  E  Q  W  S  D  Q  E  I  W
4021   TCTGGAACATTTAGAAAAAACTTGGATCCCTATGAACAGTGGAGTGATCAAGAAATATGG    1316
       K  V  A  D  E  V  G  L  R  S  V  I  E  Q  F  P  G  K  L  D
4081   AAAGTGCAGATGAGGTTGGGCTTAGATCTGTGATAGAACAGTTTCCTGGAAGCTTGAC    1336
       F  V  L  V  D  G  G  C  V  L  S  H  G  H  K  Q  L  M  C  L
4141   TTTGTCCTTGTGGATGGGGGCTGTGTCCTAAGCCATGGCCACAAGCAGTTGATGTGCTTG    1356
       A  R  S  V  L  S  K  A  K  I  L  L  L  D  E  P  S  A  H  L
4201   GCTAGATCTGTTCTCAGTAAGGCGAAGATCTTGCTTGATGAACCCAGTGCTCATTTG    1376
       D  P  V  T  Y  Q  I  I  R  R  T  L  K  Q  A  F  A  D  C  T
4261   GATCCAGTTACATACCAAATTATTAGAAGAACTCTAAAACAAGCATTTGCTGATTGCACA    1396
       V  I  L  C  E  H  R  I  E  A  M  L  E  C  Q  Q  F  L  V  I
4321   GTAATTCTCTGTGAACACAGGATAGAAGCAATGCTGGAATGCCAACAATTTTTGTCATA    1416
       E  E  N  K  V  R  Q  Y  D  S  I  Q  K  L  L  N  E  R  S  L
4381   GAAGAGAACAAAGTGCGGCAGTACGATTCCATCCAGAAACTGCTGAACGAGAGGAGCCTC    1436
       F  R  Q  A  I  S  P  S  D  R  V  K  L  F  P  H  R  N  S  S
4441   TTCCGGCAAGCCATCAGCCCCTCCGACAGGGTGAAGCTCTTTCCCCACCGGAACTCAAGC    1456
       K  C  K  S  K  P  Q  I  A  A  L  K  E  E  T  E  E  E  V  Q
4501   AAGTGCAAGTCTAAGCCCCAGATTGCTGCTCTGAAAGAGGAGACAGAAGAAGAGGTGCAA    1476
```

FIG. 1G

```
      D    T    R    L   =                                                                          1480
4561  GATACAAGGCTTTAGAGAGCAGCAGCATAAATGTTGACATGGACATTTGCTCATGGAATTGG
4621  AGCTCGTGGGACAGTCACCTCATGGAATTGGGAGCTCGTGGAACAGTTACCTCTCGCCTCAG
4681  AAACAAGGATGAATTAAGTTTTTTTAAAAGAACATTTGGTAAGGGAATTGAGG
4741  ACACTGATATGGGTCTGAAGATTTACCACTTGTTTTGCAAGCCAGATGTCAAATGTGAAGGTAC
4801  TTCAAATCCTTGAAGTAATGGAAAGGCAGCTCAAATGTCAGCCTAGTTTTCCTGAAAACCCTT
4861  GCCATGCTGCTAGTAATGGAAAGGCAGCTCAAATGTCAGCCTAGTTGATCAGCTT
4921  ATTGTCTAGTGAAACTCGTTAATTTGTAGTGTTGGAGAAGAACTGAAATCATACTTCTTA
4981  GGGTATGATTAAGTAATGATAACTGGAAACTCAGCGGTTTATATAAGCTTGTATTCCT
5041  TTTTCTCCTCTCCCATGATGTTTAGAAACACACAATATATTGTTTGCTAAGCATTCCA
5101  ACTATCTCATTCCAAGCAAGTATTAGAATACCAACAAGAACACAAGACTGCACATCAAA
5161  ATATGCCCCATTCAACATCTAGTGAGCAGTCAGGAGTCCAGATCCTGAAAT
5221  CAGGGTAGTAGTGTCCAGTCTACCAAAATCTAATATTCAGATAATCACAATACAT
5281  CCCTTACCTGGAAAGCCTTTCTCCAACTCAACTCAGAAAGTGACAAGCTCACAGACCTTGATG
5341  AAGAAGTTGATATGCTTGAAAAGTAGTAGTGCAAATTGTCACAGGACAGCCCTTCTTTCCACA
5401  AGAGTTTAGCTGGAAAAGTATGTTAGTGCAAATTGTCACAGGACAGCCCTTCTTTCCACA
5461  GAAGCTCCAGTAGAGGGTGTGAAGTAGATATAGGTAAGTATAGGTTGATGGTATGTTTGGTA
5521  TGAAGTCCAAGCATTTAGATGCTACAACTAAGAATGAGACACACTGAAGCACCAATCATG
5581  TACTTCATGCTGTTTCTGTTTATAATTTTGTAAGCAAATTTTCTGTAGGAA
5641  AATTAGTTTATATGCTTCTGTTTCAACATATTTTTATATTGAAGCAAATTTTCTCTAGGAAA
5701  TATTTATTTAATAATGTTTCAACATATTTTTATATTGAACAAATTTTCTCTAGGAAA
5761  TGAATTACACATTTGAAATTATGTTAAACTGGGACAGGGGAGAACCTAGGTGATATTAACC
5821  TATTTTATGAAATATTATGTTAAACTGGGACAGGGGAGAACCTAGGTGATATTAACC
5881  AGGGCCATGAATCACCTTTGGTCTGGAGGGAAGCCTCTTAGATGCAGTTCAGTTCTGAAGATGGT
5941  CACAGCTGTATGATTCCCAGCACAGCCCTCTTAGATGCAGTTCTGAAGATGGT
6001  ACCACCAGTCGACTGTTTCCATCAAGGGTACAAGGGTACTGTAAGAAATATCACTTGTCAATAAATCCATA
6061  TAAGAAGACTGCATTATATTTATTACTGTAAGAAAATATCACTTGTCAATAAATCCATA
6121  CATTTGTGT(A)n    SEQ ID NO: 16
```

FIG. 1H

FIG. 3A  FIG. 3B  FIG. 3C  FIG. 3D

SalI  XhoI  SfiI  NaeI

FIG. 16A

| | | |
|---|---|---|
| CFTR (N) | GEGGITLSGGQRARISLARAVYKDADLYLLDSPFGYLDVLTEK | SEQ ID NO: 18 |
| CFTR (C) | VDGGCVLSHGHKQLMCLARSVLSKAKILLLDEPSAHLDPVTYQ | SEQ ID NO: 19 |
| hmdr1 (N) | GERGAQLSGGQKQRIAIARALVRQPHILLLDEATSALDTESEK | SEQ ID NO: 20 |
| hmdr1 (C) | GDKGTLLSGGQKQRIAIARALVRQPHILLLDEATSALDTESEK | SEQ ID NO: 21 |
| mmdr1 (N) | GERGAQLSGGQKQRIAIARALVRQPHILLLDEATSALDTESEA | SEQ ID NO: 22 |
| mmdr1 (C) | GDKGTQLSGGQKQRIAIARALVRQPHILLLDEATSALDTESEK | SEQ ID NO: 23 |
| mmdr2 (N) | GDRGAQLSGGQKQRIAIARALVRNPKILLLDEATSALDTESEA | SEQ ID NO: 24 |
| mmdr2 (C) | GDKGTQLSGGQKQRIAIARALIRQPRVLLDEATSALDTESEK | SEQ ID NO: 25 |
| pfmdr (N) | GSNASKLSGGQKQRISIARAIMRNPKILLLDEATSSLDSNSEK | SEQ ID NO: 26 |
| pfmdr (C) | PYGKS-LSGGQKQRIAIARALLREPKILLLDEATSSLDNKSEY | SEQ ID NO: 27 |
| STE6 (N) | GTGGVTLSGGQQQRVAIARAFIRDTPILFLDEAVSALDIVHRN | SEQ ID NO: 28 |
| STE6 (C) | RIDTTLLSGGQAQRLCIARALLRKSKILILDECTSALDSVSSS | SEQ ID NO: 29 |
| hlyB | GEQGAGLSGGQRQRIAIARALLRDTPPLLIFDEATSALDYASEH | SEQ ID NO: 30 |
| White | PGRVKGLSGGERKRLAFASEALTDPPLLICDEPTSGLDSFTAH | SEQ ID NO: 31 |
| MbpX | FEYPAQLSGGQKQRVALARSLAIQPDLL--DEPFGALDGELRR | SEQ ID NO: 32 |
| BtuD | GRSTNQLSGGEWQRVRLAAVVLQITLLLLDEPMNSLDVAQQSA | SEQ ID NO: 33 |
| PstB | HQSGYSLSGGQQQRLCIARGIAIRPEVLLLDEPCSALDPISTG | SEQ ID NO: 34 |
| hisP | GKYPVHLSGGQQQQRVSIARALAMEPDVLLFDEPTSALDPELVG | SEQ ID NO: 35 |
| malK | DRKPKALSGGQRQRVAIGRTLVAEPSVFLLDEPLSNLDAALRV | SEQ ID NO: 36 |
| oppD | KMYPHEFSGGMRQRVMIAMALLCRPKLIIADEPTTALDVTVQA | SEQ ID NO: 37 |
| oppF | NRYPHEFSGGCQRIGIARALILEPKLIICDDAVSALDVSIQA | SEQ ID NO: 38 |
| RbsA (N) | DKLVGDLSIGDQQMVEIAKVLSFESKVIIMDEPTCALIDTETE | SEQ ID NO: 39 |
| RbsA (C) | EQAIGLLSGGNQQKVAIARGLMTRPKVLILDEPTPGVDVGAKK | SEQ ID NO: 40 |
| UvrA | GQSATTLSGGEAQRVKLARELSKRGLYILDEPTTGLHFADIQQ | SEQ ID NO: 41 |
| NodI | NTRVADLSGGMKRPLTLAGALINDPQLLILDEPTTGLDPHARH | SEQ ID NO: 42 |
| FtsE | KNFPIQLSGGEQQRVGIARAVVNKPAVLLADEPTGNLDDALSE | SEQ ID NO: 43 |

FIG.16B

CYSTIC FIBROSIS GENE

CROSS REFERENCE TO RELATED APPLICATIONS

This application is a divisional application of U.S. application Ser. No. 08/123,864, filed on Sep. 20, 1993 now abandoned, which is a file wrapper continuation of U.S. patent application Ser. No. 07/401,609, filed on Aug. 31, 1989 (now abandoned), which was a continuation-in-part (CIP) of U.S. patent application Ser. No. 07/399,945, filed on Aug. 24, 1989 (now abandoned), which was a CIP of U.S. patent application Ser. No. 07/396,894, filed on Aug. 22, 1989 (now abandoned).

RIGHTS OF THE UNITED STATES GOVERNMENT IN THIS INVENTION

This invention was mad with government support under Grants R01 DK39690-02 and DK34944 awarded by the United States National Institutes of Health. The United States government has certain rights in the invention.

FIELD OF THE INVENTION

The present invention relates generally to the cystic fibrosis (CF) gene, and, more particularly to the identification, isolation and cloning of the DNA sequence corresponding to the normal and mutant CF genes, as well as their transcripts and gene products. The present invention also relates to methods of screening for and detection of CF carriers, CF diagnosis, prenatal CF screening and diagnosis, and gene therapy utilizing recombinant technologies and drug therapy using the information derived from the DNA, protein, and the metabolic function of the cystic fibrosis transmembrane inductance regulator protein (CFTR).

BACKGROUND OF THE INVENTION

CF is the most common severe autosomal recessive genetic disorder in the Caucasian population. It affects approximately 1 in 2000 live births in North America (Boat et al, *The Metabolic Basis of Inherited Disease*, 6th ed, pp 2649–2680, McGraw Hill, NY (1989)). Approximately 1 in 20 persons are carriers of the disease.

Although the disease was first described in the late 1930's, the basic defect remains unknown. The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient calls, it is not clear that the abnormal regulation of chloride channels represents the primary defect in the disease. Given the lack of understanding of the molecular mechanism of the disease, an alternative approach has therefore been taken in an attempt to understand the nature of the molecular defect through direct cloning of the responsible gene on the basis of its chromosomal location.

However, there is no clear phenotype that directs an approach to the exact nature of the genetic basis of the disease, or that allows for an identification of the cystic fibrosis gene. The nature of the CF defect in relation to the population genetics data has not been readily apparent. Both the prevalence of the disease and the clinical heterogeneity have been explained by several different mechanisms: high mutation rate, heterozygote advantage, genetic-drift, multiple loci, and reproductive compensation.

Many of the hypotheses can not be tested due to the lack of knowledge of the basic defect. Therefore, alternative approaches to the determination and characterization of the CF gene have focussed on an attempt to identify the location of the gene by genetic analysis.

Linkage analysis of the CF gene to antigenic and protein markers was attempted in the 1950's, but no positive results were obtained (Steinberg et al *Am. J. Hum. Genet.* 8: 162–176, (1956); Steinberg and Morton *Am. J. Hum. Genet* 8: 177–189 6956); Goodchild et al *J. Med. Genet.* 7: 417–419, (1976).

More recently, it has become possible to use RFLP's to facilitate linkage analysis. The first linkage of an RFLP marker to the CF gene was disclosed in 1985(Tsui et al. *Science* 230: 1054–1057, 1985) in which linkage was found between the CF gene and an uncharacterized marker DOCRI-917. The association was found in an analysis of 39 families with affected CF children. This showed that although th chromosomal location had not been established, the location of the disease gene had be n narrowed to about 1% of the human genome, or about 30 million-nucleotide base pairs.

The chromosomal location of the DOCRI-917 probe was established using rodent-human hybrid cell lines containing different human chromosome complements. It was shown that DOCRI-917 (and therefore the CF gene) maps to human chromosome 7.

Further physical and genetic linkage studies were pursued in an attempt to pinpoint the location of the CF gene. Zengerling et al (*Am. J. Hum. Genet.* 40: 228–236 (1987)) describe the use of human-mouse somatic cell hybrids to obtain a more detailed physical relationship between the CF gene and the markers known to be linked with it. This publication shows that the CF gene can be assigned to either the distal region or band q22 or the proximal region of band q31 on chromosome 7.

Rommens et al (*Am. J. Hum. Genet.* 43: 645–663, (1988)) give a detailed discussion of the isolation of many new 7q31 probes. The approach outlined led to the isolation of two new probes, D76122 and D7S340, which are close to each other. Pulsed field gel electrophoresis mapping indicates that these two RFLP markers are between two markers known to flank the CF gene, MET (White, R., Woodward S., Leppert M., et al. *Nature* 318: 382–384, (1985)) and D7S8 (Wainwright, B. J., Scambler, P. J., and J. Schmidtke, *Nature* 318: 384–385 (1985)), therefore in the CF gene region. The discovery of these markers provides a starting point for chromosome walking and jumping.

Estivill et al, (*Nature* 326: 840–845(1997)) disclose that a candidate cDNA gene was located and partially characterized. This however, does not teach the correct location of the CF gene. The reference discloses a candidate cDNA gene downstream of a CpG island, which are undermethylated GC nucl tide-rich regions upstream of many vertebrate genes. The chromosomal localization of the candidate locus is identified as the XV2C region. This region is d scribed in European Patent Application 88303645.1. However, that actual region does not include the CF gene.

A major difficulty in identifying the CF gene has been the lack of cytologically detectable chromosome rearrangements or deletions, which greatly facilitated all previous successes in the cloning of human disease genes by knowledge of map position.

Such rearrangements and deletions could be observed cytologically and as a result, a physical location on a particular chromosome could be correlated with the particular disease. Further, this cytological location could be correlated with a molecular location based on known relationship between publicly available DNA probes and cytologically visible alterations in the chromosomes. Knowledge of the molecular location of the gene for a particular disease would allow cloning and sequencing of-that gene by routine procedures, particularly when the gene product is known and cloning success can be confirmed by immunoassay of expression products of the cloned genes.

In contrast, neither the cytological location nor the gene product of the gene for cystic fibrosis was known in the prior art. With the recent identification of MET and D7S8, markers which flanked the CF gene but did not pinpoint its molecular location, the present inventors devised various novel gene cloning strategies to approach the CF gene in accordance with the present invention. The methods employed in these strategies include chromosome jumping from the flanking markers, cloning of DNA fragments from a defined physical region with the use of pulsed field gel electrophoresis, a combination of a matic cell hybrid and molecular cloning techniques designed to isolate DNA fragments from undermethylated CpG islands near CF, chromosome microdissection and cloning, and saturation cloning of a large number of DNA markers from the 7q31 region. By means of these novel strategies, the present inventors were able to identify the gene responsible for cystic fibrosis where the prior art was uncertain or, even in one case, wrong.

The application of these genetic and molecular cloning strategies has allowed the isolation and cDNA cloning of the cystic fibrosis gene on the basis of its chromosomal location, without the benefit of genomic rearrangements to point the way. The identification of the normal and mutant forms of the CF gene and gene products has allowed for the development of screening and diagnostic tests for CF utilizing nucleic acid probes and antibodies to the gone product. Through interaction with the defective gene product and the pathway in which this gene product is involved, therapy through normal gene product supplementation and gene manipulation and delivery are now made possible.

SUMMARY OF THE INVENTION

The gene involved in the cystic fibrosis disease process, hereinafter the "CF gene" and its functional equivalents, has been identified, isolated and cDNA cloned, and its transcripts and gene products identified and sequenced. A three base pair deletion leading to the omission of a phenylalanine residue in the gene product has been determined to correspond to the mutations of the CF gene in approximately 70% of the patients affected with CF, with different mutations involved in most if not all the remaining cases.

With the identification and sequencing of the gene and its gene product, nucleic acid probes and antibodies raised to the gene product can be used in a variety of hybridization and immunological assays to screen for and detect the presence of either a normal or a defective CF gene or gene product. Assay kits for such screening and diagnosis can also be provided.

Patient therapy through supplementation with th normal gene product, whose production can be amplified using genetic and recombinant techniques, or its functional equivalent, in now also possible. Correction or modification of the defective gene product through drug treatment means is now possible. In addition, cystic fibrosis can be cured or controlled through gene therapy by correcting the gene defect in situ or using recombinant or other vehicles to deliver a DNA sequence capable of expression of the normal gene product to the cells of the patient.

According to an aspect of the invention, a DNA molecule comprises a DNA sequence selected from the group consisting of:
(a) DNA sequences which correspond to the DNA sequence as set forth in the following FIGS. 1A–1H from amino acid residue position 1 to position 1480;
(b) DNA sequences encoding normal CFTR polypeptide having the sequence according to the following FIGS. 1A–1H for amino acid residue positions from 1 to 1480;
(c) DNA sequences which correspond to a fragment or the sequence of the following FIGS. 1A–1H including at least 16 sequential nucleotides between amino acid residue positions 1 and 1480;
(d) DNA sequences which comprise at least 16 nucleotides and encode a fragment of the amino acid sequence of the following FIGS. 1A–1H; and
(e) DNA sequences encoding an epitope encoded by at least 1B sequential nucleotides in the sequence of the following FIGS. 1A–1H between amino acid residue positions 1 and 1480.

According to another aspect of the invention, a purified mutant CF gene comprises a DNA sequence including an amino acid sequence for a protein where the protein, when expressed in calls of the human body, is associated with altered cell function which correlates with th genetic disease cystic fibrosis.

According to another aspect of the invention, a purified RNA molecule comprises an RNA sequence corresponding to the above DNA sequence.

According to another aspect of the invention, a DNA molecule comprises a cDNA molecule corresponding to the above DNA sequence.

According to another aspect of the invention, a purified nucleic acid probe comprises a DNA or RNA nucleotide sequence corresponding to the above noted selected DNA sequences of groups (a) to (e).

According to another aspect of the invention, a DNA molecule comprises a DNA sequence encoding mutant CFTR polypeptide having the sequence according to the following FIGS. 1A–1H for amino acid residue positions 1 to 1480. The sequence is further characterized by a three base pair mutation which results in the deletion of phenylalanine from amino acid residue position 508.

According to another aspect of the invention, a DNA molecule comprises a cDNA molecule corresponding to the above DNA sequence.

According to another aspect of the invention, the cDNA molecule comprises a DNA sequence selected from the group consisting of:
(a) DNA sequences which correspond to the mutant DNA sequence and which encode, on expression, for mutant CFTR polypeptide;
(b) DNA sequences which correspond to a fragment of the mutant DNA sequences, including at least twenty nucleotides;
(c) DNA sequences which comprise at least twenty nucleotides and encode a fragment of the mutant C M protein amino acid sequence; and
(d) DNA sequences encoding an epitope encoded by at least eighteen sequential nucleotides in the mutant DNA sequence.

According to another aspect of the invention, purified RNA molecule comprising RNA sequence corresponds to the mutant DNA sequence.

A purified nucleic acid probe comprising a DNA or RNA nucleotide sequence corresponding to the mutant sequences as recited above.

According to another aspect of the invention, a recombinant cloning vector comprising the DNA sequences of the normal or mutant DNA and fragments thereof is provided. The vector, according to an aspect of this invention, is operatively linked to an expression control sequence in the recombinant DNA molecule so that the normal CFTR protein can be expressed, or alternatively with the other selected mutant DNA sequence the mutant CFTR polypeptide can be expressed. The expression control sequence is selected from the group consisting of sequences that control the expression of genes of prokaryotic or eukaryotic cells and their viruses and combinations thereof.

According to another aspect of the invention, a method for producing normal CFTR polypeptide comprises the steps of:
  (a) culturing a host cell transfected with the recombinant vector for the normal DNA sequence in a medium and under conditions favorable for expression of the normal CFTR polypeptide; and
  (b) isolating the expressed normal CFTR polypeptide.

According to another aspect of the invention, a method for producing a mutant CFTR polypeptide comprises the steps of:
  (a) culturing a host cell transfected with the recombinant vector for the mutant DNA sequence in a medium and under conditions favorable for expression of th mutant CFTR polypeptide; and
  (b) isolating the expressed mutant CFTR polypeptide.

According to another aspect of the invention, a purified protein of human cell membrane origin comprises an amino sequence encoded by the mutant DNA sequence where the protein, when present in human cell membrane, is associated with cell function which causes the genetic disease cystic fibrosis.

According to another aspect of the invention, the CFTR polypeptide is characterized by a molecular weight of about 170,000 daltons and an epithelial cell transmembrane ion conductance affecting activity.

According to another aspect of the invention, a substantially pure CFTR protein normally expressed in human epithelial cells and characterized by being capable of participating in regulation and in control of ion transport through epithelial cells by binding to epithelial cell membrane to modulate ion movement through channels formed in the epithelial cell membrane.

According to another aspect of the invention, a process for isolating the CFTR protein comprises:
  (a) extracting peripheral proteins from membranes of epithelial cells to provide membrane material having integral proteins including said CFTR protein:
  (b) solubilizing said integral proteins of said membrane material to form a solution of said integral proteins;
  (c) separating said CFTR protein to remove any remaining other proteins of mammalian origin.

According to another aspect of the invention, a method is provided for screening a subject to determine if the subject is a CP carrier or a CF patient comprising the steps of providing a biological sample of the subject to be screened and providing an assay for detecting in the biological sample, the presence of at least a member from the group consisting of the normal CF gene, normal CF gen products, a mutant CF gene, mutant CF gene products and mixtures thereof.

According to another aspect of the invention, an immunologically active anti-CFTR polyclonal or monoclonal antibody specific for CFTR polypeptide is provided.

According to another aspect of the invention, a kit for assaying for the presence of a CF gone by immunoassay techniques comprises:

(a) an antibody which specifically binds to a gene product of the CF gene;
  (b) reagent means for detecting the binding of the antibody to the gene product; and
  (c) the antibody and reagent means each being present in amounts effective to perform the immunoassay.

According to another aspect of the invention, a kit for assaying for the presence of a CF gene by hybridization technique comprises:
  (a) an oligonucleotide probe which specifically binds to the CF gene;
  (b) reagent means for detecting the hybridization of the oligonucleotide probe to the CF gene; and
  (c) the probe and reagent means each being present in amounts effective to perform the hybridization assay.

According to another aspect of the invention, a method is provided for treatment for cystic fibrosis in a patient. The treatment comprises the step of administering to the patient a therapeutically effective amount of the normal CFTR protein.

According to another aspect of the invention, a method of gene therapy for cystic fibrosis comprises th step of delivery of a DNA molecule which includes a sequence corresponding to th normal DNA sequence encoding for normal CFTR protein.

According to another aspect of the invention, an animal comprises an heterologous cell system. The cell system includes a recombinant cloning vector which includes the recombinant DNA sequence corresponding to the mutant DNA sequence which induces cystic fibrosis symptoms in the animal.

According to another aspect of the invention, a transgenic mouse exhibits cystic fibrosis symptoms.

BRIEF DESCRIPTION OF THE DRAWINGS

Figure 1A:
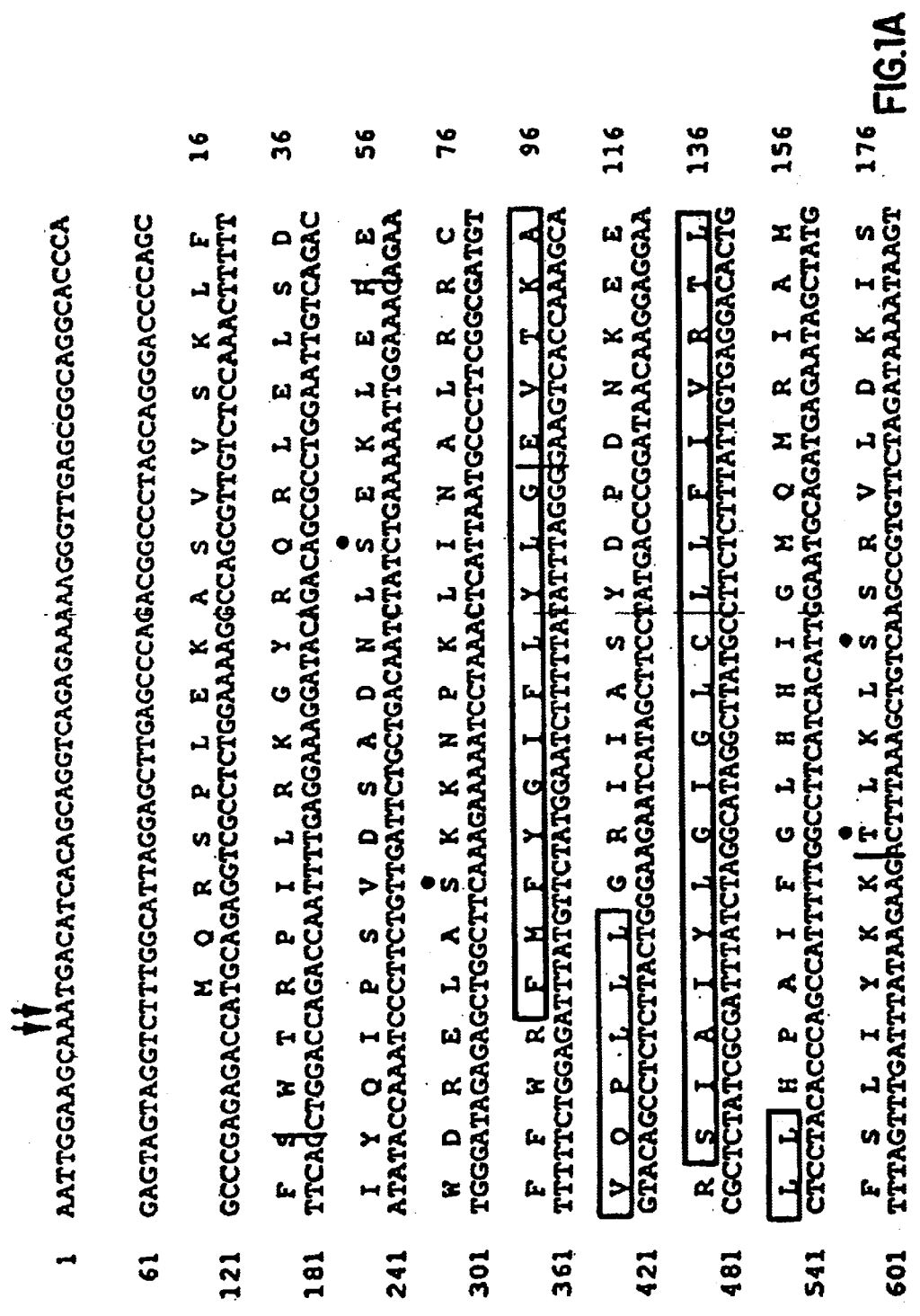
Figure 1B:
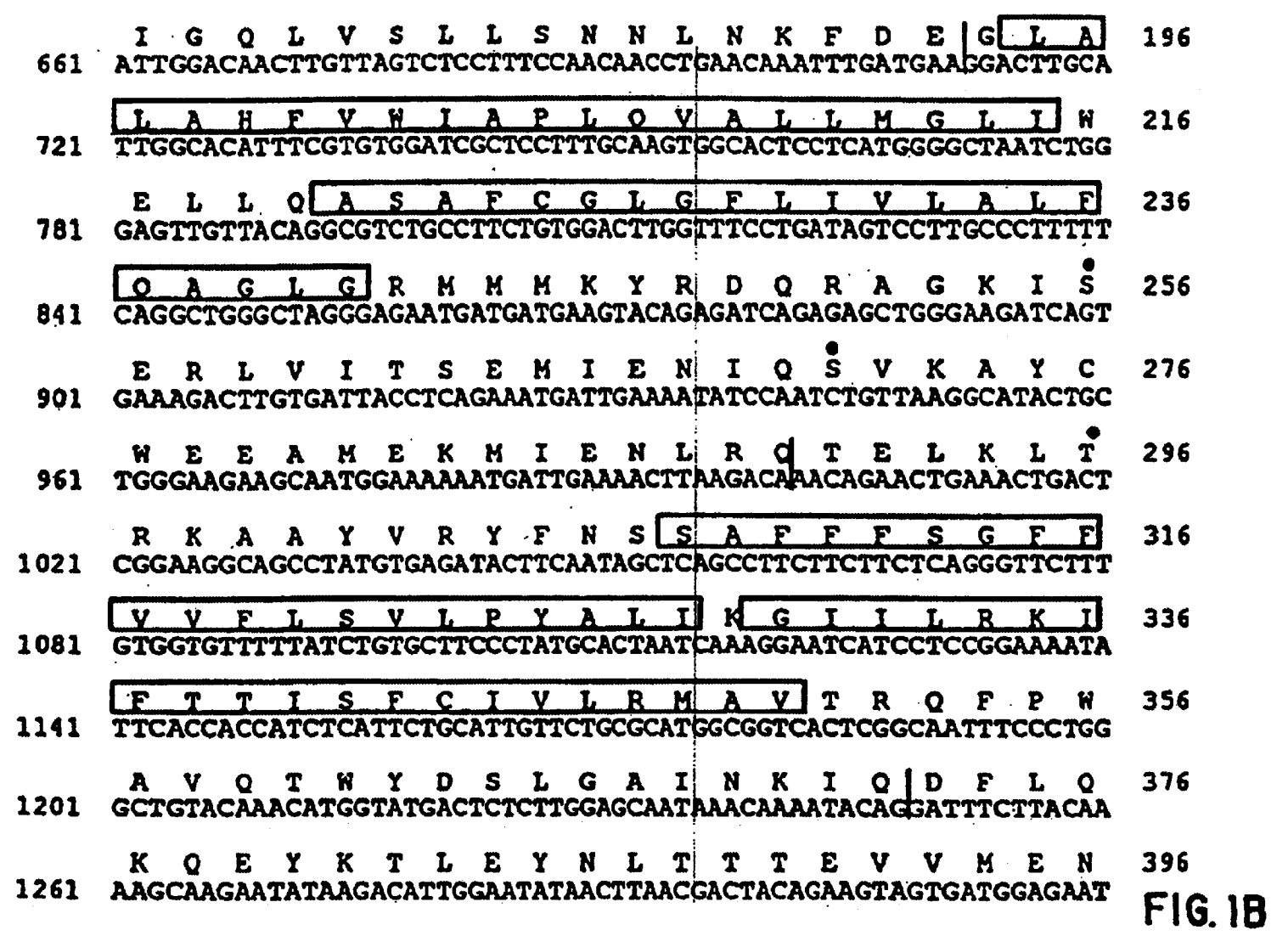

FIGS. 1A–1H are the nucleotide sequence of the CF gene and the amino acid sequence of the CFTR protein.

FIGS. 2A–2G are a restriction map of the CF gone and the schematic strategy used to chromosome walk and jump to the gene.

FIGS. 3A–3E are a pulsed-field-gel electrophoresis map of the region including and surrounding the CF gene.

FIGS. 16A–16B represent alignment of the most conserved segments of the extended nucleotides binding folds (NBFs) of CFTR with comparable regions of other proteins.

DETAILED DESCRIPTION OF THE PREFERRED EMBODIMENTS

1. Definitions

Figure 2A:
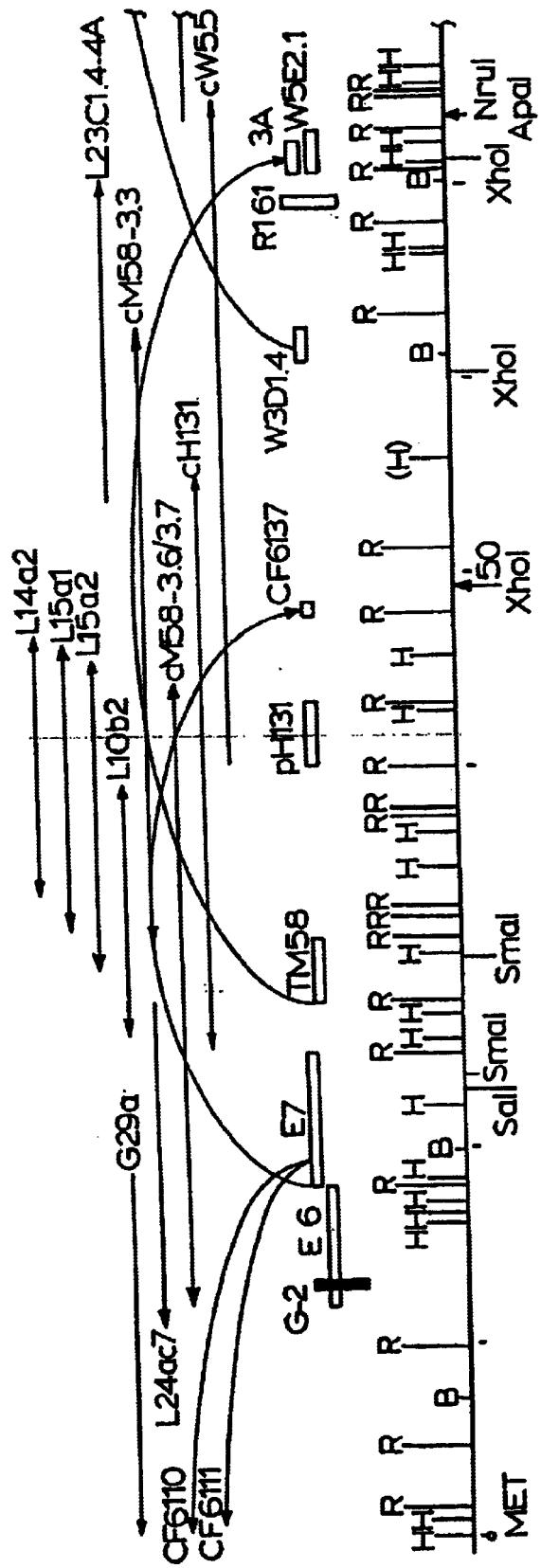
Figure 2B:
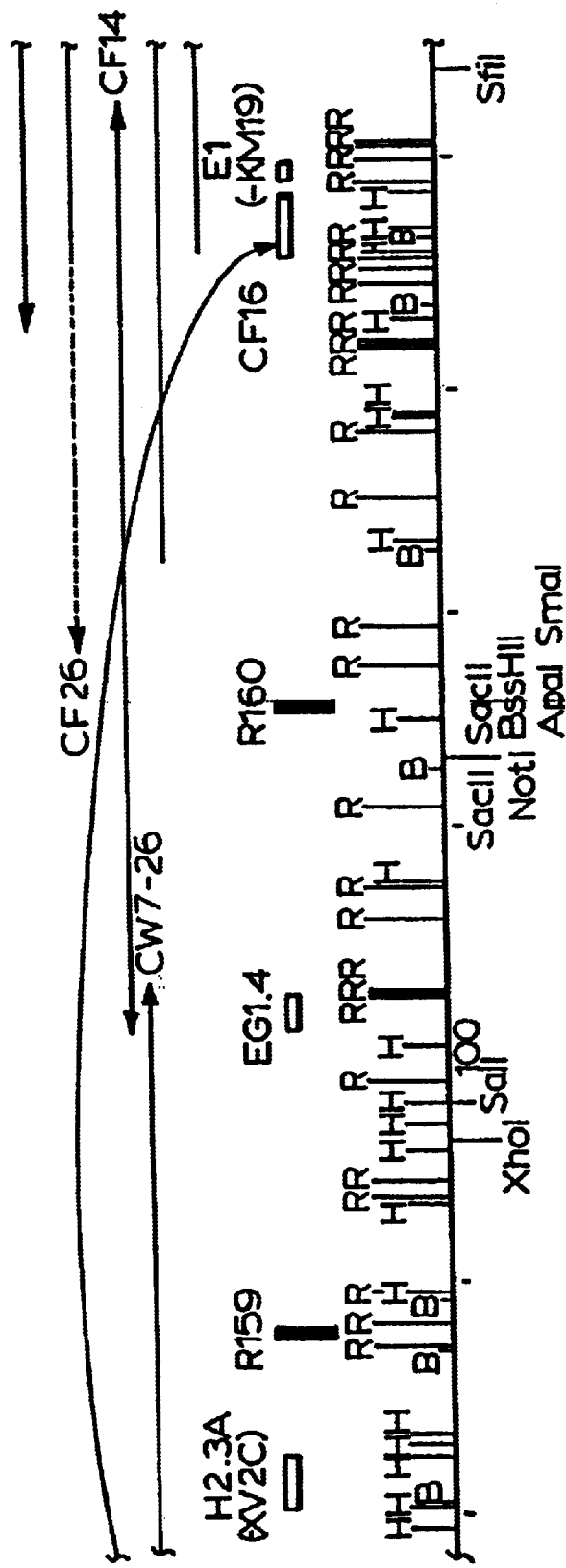
Figure 2C:
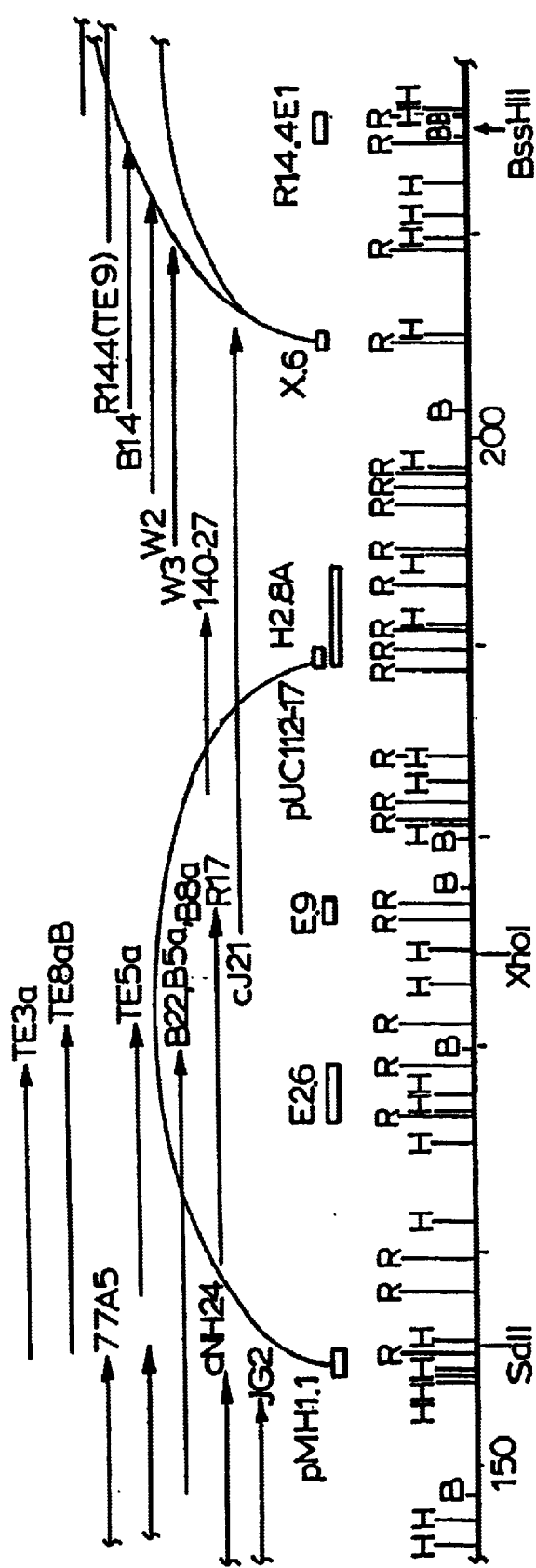
Figure 2D:
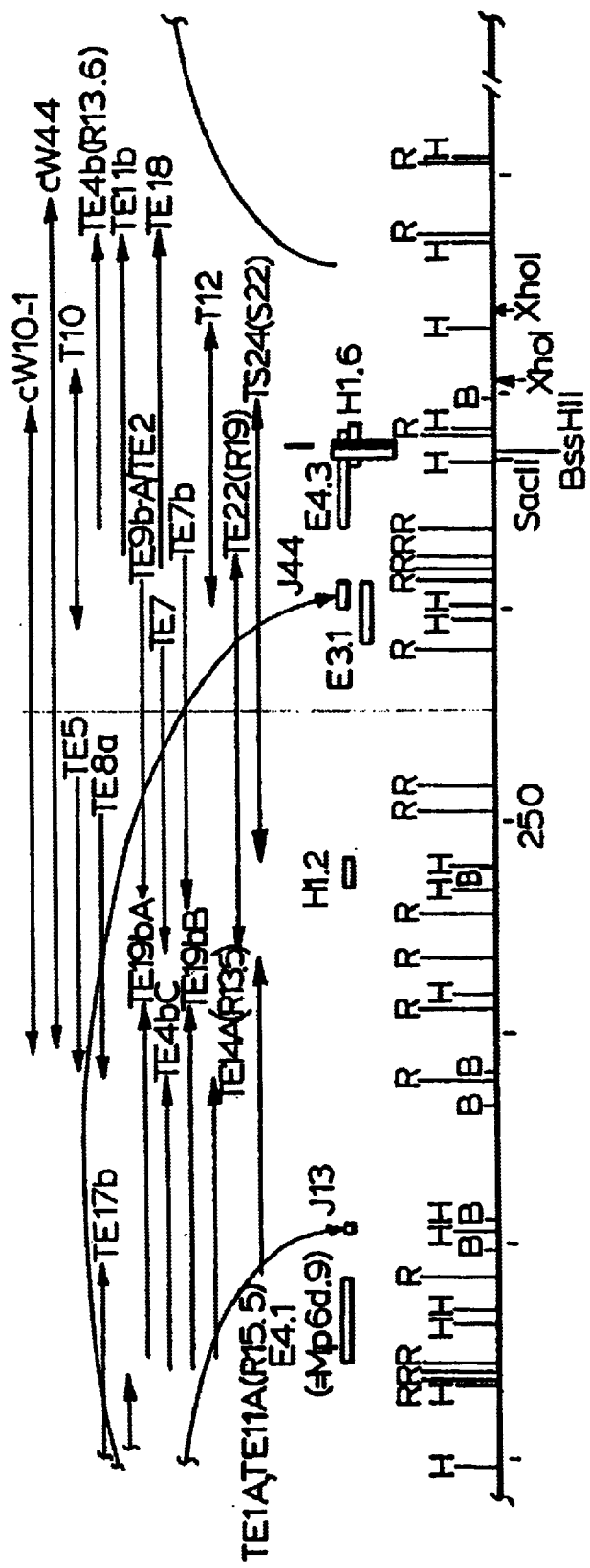
Figure 2E:
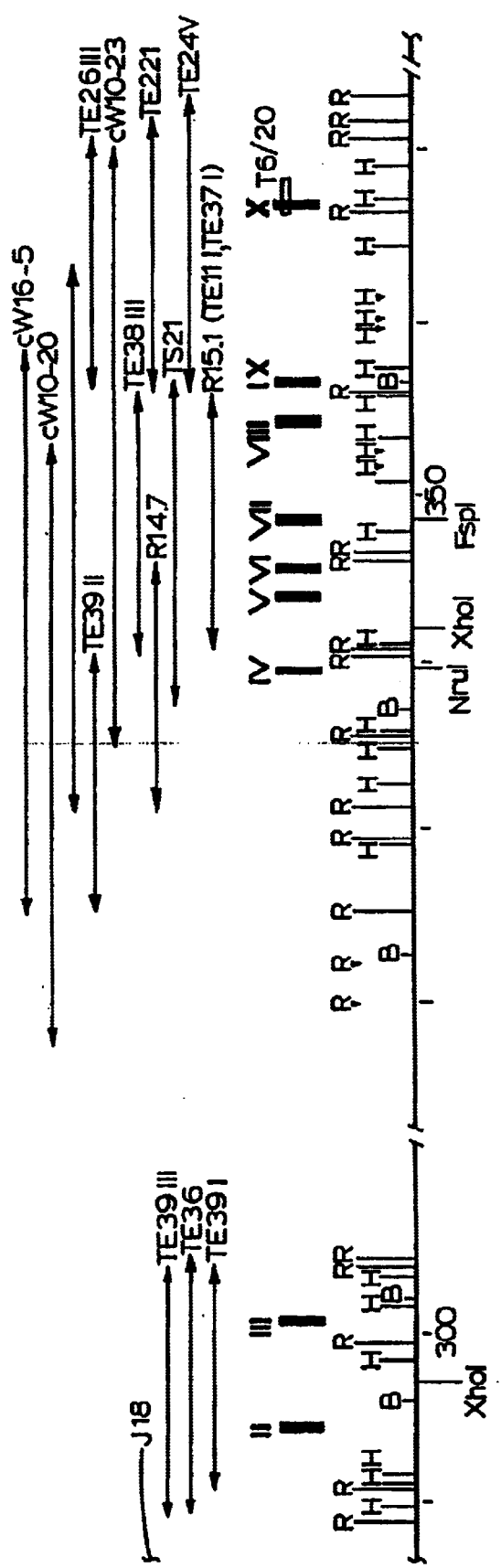
Figure 2F:
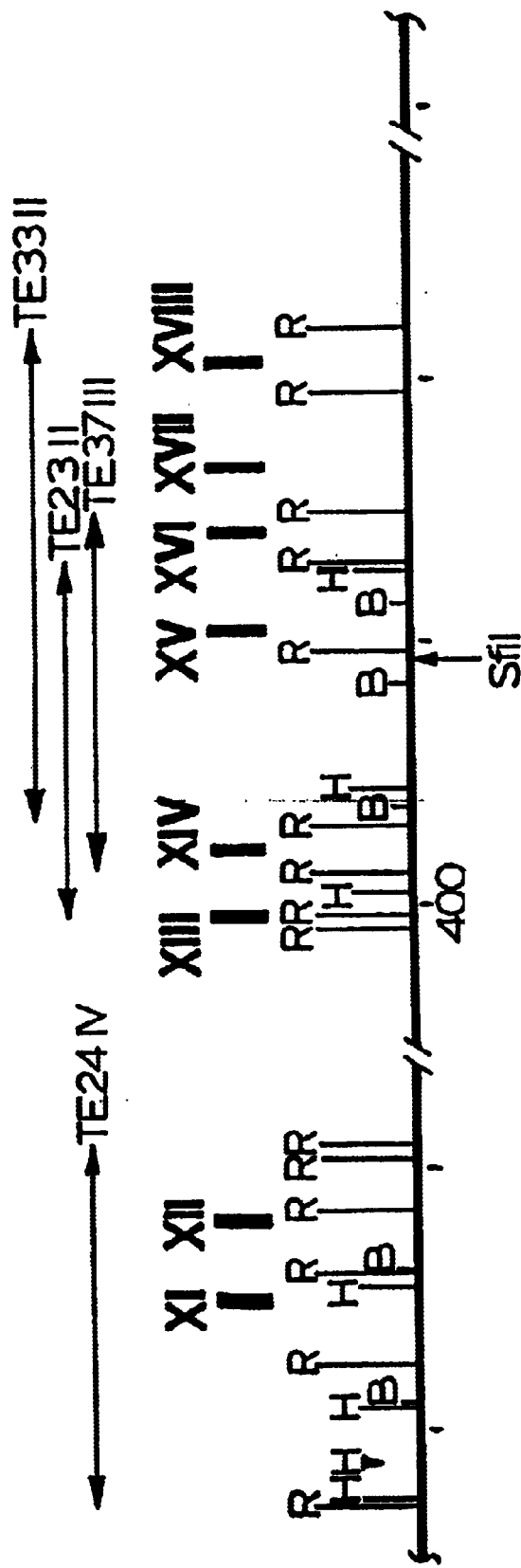

In order to facilitate review of th various embodiments of the invention and an understanding of various elements and constituents used in making the invention and using same, the following definition of terms used in the invention description is as follows:

CF-cystic fibrosis

CF carrier-a person in apparent health whose chromosomes contain a mutant CP gene that may be transmitted to that person's offspring.

CF patient-a person who carries a mutant CF gene on each chromosome, such that they exhibit the clinical symptoms of cystic fibrosis.

CF gene-the gene whose mutant forms are associated with the disease cystic fibrosis. This definition is understood to include the various sequence polymorphisms that exist, wherein nucleotide substitutions in the gene sequence do not affect the essential function of the gone product. This term primarily relates to an isolated coding sequence, but can also include some or all of the flanking regulatory elements and/or introns.

CF-PI-cystic fibrosis pancreatic insufficient, the major clinical subgroup of cystic fibrosis patients, characterized by insufficient pancreatic exocrine function.

CF-PS-cystic fibrosis pancreatic sufficient, a clinical subgroup of cystic fibrosis patients with sufficient pancreatic exocrine function for normal digestion of food.

CFTR-cystic fibrosis transmembrane conductance regulator protein, encoded by the CF gene. This definition includes the protein as isolated from human or animal sources, as produced by recombinant organisms, and as chemically or enzymatically synthesized. This definition is understood to include the various polymorphic forms of the protein wherein amino acid substitutions in th variable regions of the sequence does not affect the essential functioning of the protein, or its hydropathic profile or secondary or tertiary structure.

DNA-standard nomenclature is used to identify the bases.

Intronless DNA-a piece of DNA lacking internal noncoding segments, for example, cDNA.

IRP locus sequence-(protooncogene int-1 related), a gene located near the CF gene.

Mutant CFTR-a protein that is highly analagous to CFTR in terms of primary, secondary, and tertiary structure, but wherein a small number of amino acid substitutions and/or deletions and/or insertions result in impairment of its essential function, so that organisms whose epithelial cells express mutant CFTR rather than CFTR demonstrate the symptoms of cystic fibrosis.

mCF-a mouse gene orthologous to the human CF gone

NBFs-nucleotide (ATP) binding folds

ORF-open reading frame

PCR-polymerase chain reaction

Protein-standard single letter nomenclature is used to identify the amino acids

R-domain-a highly charged cytoplasmic domain of the CFTR protein

RSV-Rous Sarcoma Virus

SAP-surfactant protein

RFLP-restriction fragment length polymorphism

2. Isolating the CF Gene

Using chromosome walking, jumping, and cDNA hybridization, DNA sequences encompassing >500 kilobase pairs (kb) have been isolated from a region on the long arm of human chromosome 7 containing th cystic fibrosis (CF) gene. Several transcribed sequences and conserved segments have been identified in this region. On of th se corresponds to the CF gene and spans approximately 250 kb of genomic DNA. Overlapping complementary DNA (cDNA) clones have been isolated from epithelial cell libraries with a genomic DNA segment containing a portion of the cystic fibrosis gene. The nucleotide sequence of the isolated cDNA is shown in FIGS. 1A–1H. In each row of the respective sequences the lower row is a list by standard nomenclature of the nucleotide sequence. The upper row in each respective row of sequences is standard single letter nomenclature for the amino acid corresponding to the respective codon.

Accordingly, the invention provides a cDNA molecule comprising a DNA sequence selected from the group consisting of:

(a) DNA sequences which correspond to the DNA sequence of FIGS. 1A–1H from amino acid residue position 1 to position 1480:

(b) DNA sequences encoding normal CFTR polypeptide having the sequence according to FIGS. 1A–1H for amino acid residue positions from 1 to 1480;

(c) DNA sequences which correspond to a fragment of the sequence of FIGS. 1A–1H including at least id sequential nucleotides between amino acid residue positions 1 and 1480;

(d) DNA sequences which comprise at least 16 nucleotides and encode a fragment of the amino acid sequence of FIGS. 1A–1H; and (e) DNA sequences encoding an epitope encoded by at least 18 sequential nucleotides in the sequence of FIGS. 1A–1H between amino acid residue positions 1 and 1480.

The invention also provides a cDNA molecule comprising a DNA sequence selected from the group consisting of:

a) DNA sequences which correspond to th DNA sequence encoding mutant CFTR polypeptide characterized by cystic fibrosis-associated activity in human epithelial cells, or the DNA sequence of FIGS. 1A–1H for the amino acid residue positions 1 to 1480 yet further characterized by a three base pair mutation which results in the deletion of phenylalanine from amino acid residue position 508;

b) DNA sequences which correspond to fragments of the sequences of paragraph a) and which include at least sixteen nucleotides;

c) DNA sequences which comprise at least sixteen nucleotides and encode a fragment of the amino acid sequence encoded for by the DNA sequences of paragraph a); and d) DNA sequences encoding an epitope encoded by at least 18 sequential nucleotides in the sequence of the DNA of paragraph a).

Transcripts of approximately 6,500 nucleotides in size are detectable in tissues affected in patients with CF. Based upon the isolated nucleotide sequence, the predicted protein consists of two similar regions, each containing a first domain having properties consistent with membrane association and a second domain believed to be involved in ATP binding.

A 3 bp deletion which results in the omission of a phenylalanine residue at the center of the first predicted nucleotide binding domain (amino acid position 508 of the CF gene product) has been detected in CF patients. This mutation in the normal DNA sequence of FIGS. 1A–1H corresponds to approximately 70% of the mutations in cystic fibrosis patients. Extended haplotype data based on DNA markers closely link d to the putative disease gene suggest that th remainder of the CF mutant gene pool consists of multiple, different mutations. A small set of these latter mutant all lea (approximately 8%) may confer residual pancreatic exocrine function in a subgroup of patients who are pancreatic sufficient.

2.1 Chromosome Walking and Jumping

Large amounts of the DNA surrounding the D7S122 and D75340 linkage regions of Rommens et al supra were searched for candidate gene sequences. In addition to conventional chromosome walking methods, chromosome jumping techniques were employed to accelerate the search process. From each jump endpoint a new bidirectional walk could be initiated. Sequential walks halted by "unclonable" regions often encountered in the mammalian genome could be circumvented by chromosome jumping.

The chromosome jumping library used has been described previously (Collins et al, *Science* 235, 1046 (1987); Ianuzzi et al *Am. J. Rum. Genet.* 44, 695 (1989)). The original library was prepared from a preparative pulsed field gel, and was intended to contain partial EcoRI fragments of 70–130 kb; subsequent experience with this library indicates that smaller fragments were also represented, and jumpsizes of 25–110 kb have been found. The library was plated on sup⁻ host MC1061 and screened by standard techniques, (Maniatis et al). Positive clones were subcloned into pBRΔ23Ava and the beginning and end of the jump identified by EcoRI and Ava 1 digestion, as described in Collins, *Genome analysis: A practical approach* (IRL, London, 1988), pp. 73–94. For each clone, a fragment from the end of the jump was checked to confirm its location on chromosome 7. The contiguous chromosome region covered by chromosome walking and jumping was about 250 kb. Direction of the jumps was bias d by careful choice of probes, as described by Collins et al and Ianuzzi et al, supra. The entire region cloned, including the sequences isolated with the Use of the CF gene cDNA, is approximately 500 kb.

The schematic representation of the chromosome walking and jumping strategy is illustrated in FIGS. 2A–2G. CF gene exons are indicated by Roman numerals in these Figures. Horizontal lines above the map indicate walk steps whereas the arcs above the map indicate jump steps. The Figure proceeds from left to right in each of six tiers with the direction of ends toward 7cen and 7qter as indicated. The restriction map for the enzymes EcoRI, HindIII, and BamHI is shown above the solid line, spanning the entire cloned region. Restriction sites indicated with arrows rather than vertical lines indicate sites which have not been unequivocally positioned. Additional restriction sites for other enzymes are shown below the line. Gaps in the cloned region are indicated by ||. These occur only in the portion detected by cDNA clones of the CF transcript. These gaps are unlikely to be large based on pulsed field mapping of the region. The walking clones, as indicated by horizontal arrows above the map, have the direction of the arrow indicating the walking progress obtained with each clone. Cosmid clones begin with the letter c; all other clones are phage. Cosmid CF26 proved to be a chimera; the dashed portion is derived from a different genomic fragment on another chromosome. Roman numerals I through XXIV indicate the location of exons of the CF gene. The horizontal boxes shown above the line are probes used during the experiments. Three of the probes represent independent subcloning of fragments previously identified to detect polymorphisms in this region: H2.3A corresponds to probe XV2C (X. Estivill et al, *Nature,* 326: 840 (1987)), probe E1 corresponds to KM19 (Estivill, supra), and probe E4.1 corresponds to Mp6d.9 (X. Estivill et al. *Am. J. Hum. Genet.* 44, 704 (1989)). G-2 is a subfragment of E6 which detects a transcribed sequence. R161, R159, and R160 are synthetic oligonucleotides constructed from parts of the IRP locus sequence (B. J. Wainwright at al, *EMBO J.,* 7: 1743 (1988)), indicating the location of this transcript on the genomic map.

As the two independently isolated DNA markers, D7S122 (pH131) and D7S340 (TM58), were only approximately 10 kb apart (FIGS. 2A–2G), the walks and jumps were essentially initiated from a single point. The direction of walking and jumping with respect to MET and D7S8 was then established with the crossing of several rare-cutting restriction endonuclease recognition sites (such as those for Xho I, Nru I and Not I, see FIGS. 2A–2G) and with reference to the long range physical map of J. M. Rommens et al. *Am. J. Hum. Genet.,* in press; A. M. Poustka, et al, *Genomics* 2, 337 (1988)1 M. L. Drumm et al. *Genomics* 2, 346 (1988). The pulsed field mapping data also revealed that the Not I site identified by the inventors of the present invention (see FIG. 2B, position 113 kb) corresponded to the one previously found associated with the IRP locus (Estivill et al 1987, supra). Since subsequent genetic studies showed that CF was most likely located between IRP and D7S8(M. Farrall et al, *Am. J. Hum. Genet.* 43, 471 (1988), B.-S. Kerem et al. *Am, J. Hum. Genet.* 44, 827 (1989)), the walking and jumping effort was continued exclusively towards cloning of this interval. It is appreciated, however, that other coding regions, as identified in FIGS. 2A–2G, for example, G-2, CF14 and CF16, were located and extensively investigated. Such extensive investigations of theme other regions revealed that they were not the CF gene based on genetic data and sequence analysis. Given the lack of knowledge of the location of the CF gene and its characteristics, the extensive and time consuming examination of the nearby presumptive coding regions did not advance the direction of search for the CF gene. However, these investigations were necessary in order to rule out the possibility of the CF gene being in those regions.

Three regions in the 280 kb segment were found not to be readily recoverable in the amplified genomic libraries initially used. These less clonable regions were located near the DNA segments H2.3A and X.6, and just beyond cosmid cW44, at positions 75–100 kb, 205–2.25 kb, and 275–285 kb in FIGS. 2A–2G, respectively. The recombinant clones near H2.3A were found to be very unstable with dramatic rearrangements after only a few passages of bacterial culture. To fill in the resulting gaps, primary walking libraries were constructed using special host-vector systems which have been reported to allow propagation of unstable sequences (A. R. Wyman, L. B. Wolfe, 6. Botatein, *Proc. Nat. Acad. Sci. U.S.A* 82, 2880 (1985); X. F. Wertman, A. R. Wyman, D. Botstein, *Gene* 49, 253 (1986); A. R. Wyman, K. F. Wertman, D. Barker, C. Helms, W. H. Petri, *Gene,* 49, 263 (1986)). Although the region near cosmid cW44 remains to be recovered, the region near X.6 was successfully rescued with these libraries.

2. Construction of Genomic Libraries

Genomic libraries wars constructed after procedures described in Maniatis, et al, *Molecular Cloning: A Laboratory Manual* (Cold Spring Harbor Laboratory, Cold Spring Harbor, N.Y. 1982) and are listed in Table 1. This includes eight phage libraries, one of which was provided by T. Maniatis (Fritsch et al, *Cell,* 19:959 (1980)); the rest were constructed as part of this work according to procedures described in Maniatis at al, supra. Four phage libraries were cloned in λDASH (commercially available from Stratagene) and there in λFIX (commercially available from Stratagene), with vector arms provided by the manufacturer. One λDASH library was constructed from Sau 3A-partially digested DNA from a human-hamster hybrid containing human chromosome 7 (4AF/102/K015) (Rommens et al *Am. J. Hum. Genet* 43, 4 (1988)), and other libraries from partial Sau3A, total BamHI, or total EcoRI digestion of human peripheral blood or lymphoblastoid DNA. To avoid loss of unstable sequences, five of the phage libraries were propagated on the recombination-deficient hosts DB1316 (recD⁻), CES 200 (recBC⁻)(Wyman et al, supra, (Wertman et al supra, Wyman et al supra); TAP90(Patterson et al *Nucleic Acids Res.* 15:6298 (1987)). Three cosmid libraries were then constructed. In one the vector pCV108 (Lau at al *Proc. Natl. Acad. Sci USA* 80:5225 (1983)) was used to clone partially digested (Sau 3A) DNA from 4AF/102/K015 (Rommens et al *Am. J. Hum. Genet.* 43:4 (1988)). A second cosmid library was prepared by cloning partially digested (Mbo I) human lymphoblastoid DNA into the vector pWE-IL2R, prepared by inserting the RSV (Rous Sarcoma Virus) promoter-driven cDNA for the interleukin-2 receptor α-chain (supplied by M. Fordis and B. Howard) in place of the neo-resistance gene of pWE15(Wahl et al *Proc. Natl. Acad. Sci. USA* 84:2160 (1987)). An additional partial Mbo I cosmid library was prepared in the vector pWE-IL2-Sal, created by inserting a Sal I linker into the Bam HI cloning site of pWE-EL2R (M. Drumm, unpublished data); this allows the use of the partial fill-in technique to ligate Sal I and Mbo I ends, preventing tandem insertions (Zabarovsky et al *Gene* 42:19 (1986)). Cosmid libraries were propagated in *E. coli* host strains DH1 or 490A (M. Steinmetz, A. Winoto, K. Minard, L. Hood, *Cell* 28, 489(1982)).

TABLE 1

GENOMIC LIBRARIES

| Vector | Source of human DNA | Host | Complexity | Ref |
|---|---|---|---|---|
| λ Charon 4A | HaeII/AluI-partially digested total human liver DNA | LE392 | $1 \times 10^6$ (amplified) | Lawn et al 1980 |
| pCV108 | Sau3a-partially digested DNA from 4AF/KO15 | DK1 | $3 \times 10^6$ (amplified) | |
| λdash | Sau3A-partially digested DNA from 4AF/KO15 | LE392 | $1 \times 10^6$ (amplified) | |
| λdash | Sau3A-partially digested total human peripheral blood DNA | DB1316 | $1.5 \times 10^6$ | |
| λdash | BamHI-digested total human peripheral blood DNA | DB1316 | $1.5 \times 10^6$ | |
| λdash | EcoRI-partially digested total human peripheral blood DNA | DB1316 | $8 \times 10^6$ | |
| λFIX | MboI-partially digested human lymphoblastoid DNA | IE392 | $1.5 \times 10^6$ | |
| λFIX | MboI-partially digested human lymphoblastoid DNA | CE200 | $1.2 \times 10^6$ | |
| λFIX | MboI-partially digested human lymphoblastoid DNA | TAP90 | $1.3 \times 10^6$ | |
| pWE-IL2R | MboI-partially digested human lymphoblastoid DNA | 490A | $5 \times 10^5$ | |
| pWE-IL2R-Sal | MboI-partially digested human lymphoblastoid DNA | 490A | $1.2 \times 10^6$ | |
| λCh3A Δlac (jumping) | EcoRI-partially digested (24–110 kb) human lymphoblastoid DNA | MC1061 | $3 \times 10^6$ | Collins et al supra and Iannuzzi et al, supra |

Three of the phage libraries were propagated and amplified in *E. coli* bacterial strain LE392. Four subsequent libraries were plated on th recombination-deficient hosts DB1316 (recD⁻) or CES200 (rec BC⁻) (Wyman 1985, supra; Wertman 1986, supra; and Wyman 1986, supra] or in one case TAP90(T. A. Patterson and M. Dean, *Nucleic Acids Research* 15, 6298 (1987)).

Single copy DNA segments (free of repetitive elements) near the ends of each phage or cosmid insert were purified and used as probes for library screening to isolate overlapping DNA fragments by standard procedures. (Maniatis, et al, supra).

1–2×10⁶ phage clones were plated on 25–30 150 mm petri dishes with the appropriate indicator bacterial host and incubated at 37° C. for 10–16 hr. Duplicate "lifts" were prepared for each plate with nitrocellulose or nylon membranes, prehybridized and hybridized under conditions described (Rommens et al, 1988, supra). Probes were labelled with $^{32}$P to a specific activity of >5×10⁸ cpm/μg using the random priming procedure (A. P. Feinberg and B. Vogelstein, *Anal. Biochem.* 132, 6 (1983)). The cosmid library was spread on ampicillin-containing plates and screened in a similar manner.

DNA probes which gave high background signals could often be used more successfully by preannealing the boiled probe with 250 µg/ml sheared denatured placental DNA for 60 minutes prior to adding the probe to the hybridization bag.

For each walk step, the identity of the cloned DNA fragment was determined by hybridization with a somatic cell hybrid panel to confirm its chromosomal location, and by restriction mapping and Southern blot analysis to confirm its colinearity with the genome.

The total combined cloned region of the genomic DNA sequences was isolated and the overlapping cDNA clones extended >500 kb. To ensure that the DNA segments isolated by the chromosome walking and jumping procedures were colinear with the genomic sequence, each segment was examined by:

(a) hybridization analysis with human-rodent somatic hybrid cell lines to confirm chromosome 7 localization, (b) pulsed field gel electrophoresis, and (c) comparison of the restriction map of the cloned DNA to that of the genomic DNA.

Accordingly, single copy human DNA sequences were isolated from each recombinant phage and cosmid clone and used as probes in each of these hybridization analyses as performed by the procedure of Maniatis, at al supra.

While the majority of phage and cosmid isolates represented correct walk and jump clones, a few resulted from cloning artifacts or cross-hybridizing sequences from other regions in the human genome, or from the hamster genome in cases where the libraries were derived from a human-hamster hybrid cell line. Confirmation of correct localization was particularly important for clones isolated by chromosome jumping. Many jump clones were considered and resulted in non-conclusive information leading the direction of investigation away from the gene.

2.3 CONFIRMATION OF THE RESTRICTION MAP

Further confirmation of the overall physical map of the overlapping clones was obtained by long range restriction mapping analysis with the use of pulsed field gel electrophoresis (J. M. Rommens, et al. *Am. J. Hum, Genet*, in press, A. M. Poustka et al, 1988, supra M. L. Drum=et al, 1988 supra).

Figures 3A, 3B, 3C, 3D:
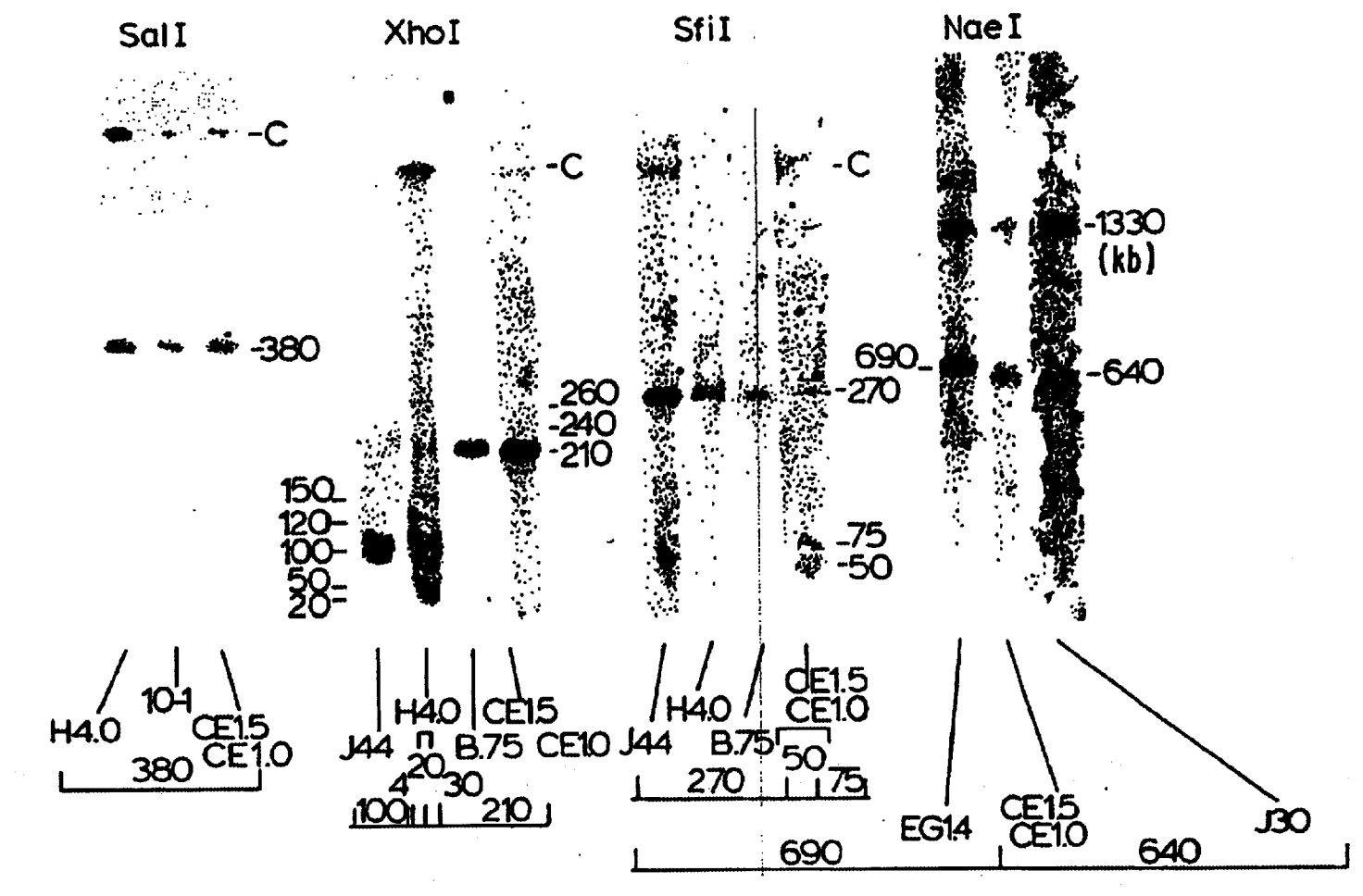
Figure 3E:
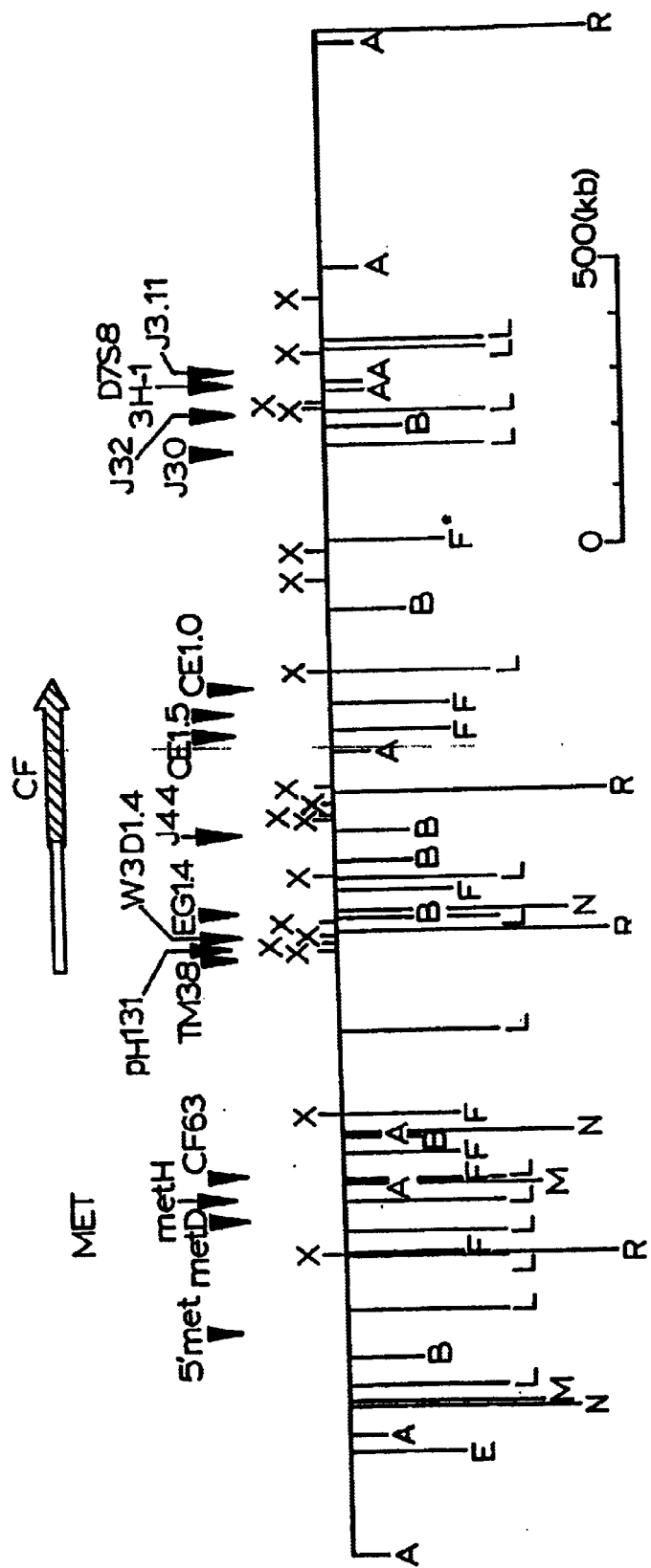

FIGS. 3A–3E illustrates the findings of the long rang restriction mapping study, where a schematic representation of the region is given in FIG. 3E. DNA from the human-hamster cell line 4AF/102/K015 was digested with the enzymes (A) Sal I, (B) Xho I, (C) Sfi I and (D) Na I, separated by pulsed field gel electrophoresis, and transferred to Zetaprobe (BioRad). For each enzyme a single blot was sequentially hybridized with the probes indicated below each of the panels of FIGS. 3A–3D, with stripping of the blot between hybridizations. The symbols for each enzyme of FIG. 3E are: A, Nae I; B, Bss HII; F. Sfi I; L, Sal I; M, M1u I; N, Not I; R, Nru I; and X, Xho 1. C corresponds to the compression zone region of the gel. DNA preparations, restriction digestion, and crossed field gel electrophoresis methods have been described (Rommens et al, in press, supra). The gels in FIGS. 3A–3D were run in 0.5X TBE at 7 volts/cm for 20 hours with switching linearly ramped from 10–40 seconds for FIGS. 3A–3C, and at 8 volts/cm for 20 hours with switching ramped linearly from 50–150 seconds for FIG. 3D. Schematic interpretations of the hybridization pattern are given below each panel. Fragment lengths are in kilobases and were sized by comparison to oligomerized bacteriophage λDNA and *Saccharomyces cerevisiae* chromosomes.

H4.0, J44, EG1.4 are genomic probes generated from the walking and jumping experiments (see FIGS. 2A–2G). J30 has been isolated by four consecutive jumps from D7S8 (Collins et al, 1987, supra; Ianuzzi et al, 1989, supra; M. Dean, et al, submitted for publication). 10–1, B.75, and CE1.5/1.0 are cDNA probes which cover different regions of the CF transcript: 10–1 contains exons I–VI, B.75 contains exons V–XII, and CE1.5/1.0 contains exons XII–XXIV. Shown in FIG. 3E is a composite map of the entire MET-D7S8 interval. The boxed region indicates the segment cloned by walking and jumping, and the slashed portion indicates the region covered by the CF transcript. The CpG-rich region associated with the D7S23 locus (Estivill et al, 1987, supra) is at the Not I sit shown in parentheses. This and other sites shown in parentheses or square brackets do not cut in 4AF/102/K015, but have been observed in human lymphoblast cell lines.

2.4 Identification of CF Gene

Based on the findings of long range restriction mapping detailed above it was determined that the entire CF gene is contained on a 380 kb Sal I fragment. Alignment of the restriction sites derived from pulsed field gel analysis to those identified in the partially overlapping genomic DNA clones revealed that the size of the CF gene was approximately 250 kb.

The most informative restriction enzyme that served to align the map of the cloned DNA fragments and the long range restriction map was Xho I; all of the 9 Xho 1 sites identified with the recombinant DNA clones appeared to be susceptible to at least partial cleavage in genomic DNA (compare maps in FIGS. 1A–2H and 2A–2G). Furthermore, hybridization analysis with probes derived from the 3' end of the CF gene identified 2 SfiI sites and confirmed the position of an anticipated Nae I site.

These findings further supported the conclusion that the DNA segments isolated by the chromosome walking and jumping procedures were colinear with the genuine sequence.

2.5 CRITERIA FOR IDENTIFICATION

A positive result based-on one or =re of the following criteria suggested that a cloned DNA segment may contain candidate gene sequences:

(a) detection of cross-hybridizing sequences in other species (as many genes show evolutionary conservation), (b) identification of CPG islands, which often mark the 5' end of vertebrate genes (A. P. Bird, *Nature*, 321, 209 (1986); M. Gardiner-Garden and M. Frommer, *J. Mol. Biol*, 196, 261 (1987)), (c) examination of possible mRNA transcripts in tissues affected in CF patients, (d) isolation of corresponding cDNA sequences, (e) identification of open reading frames by direct sequencing of cloned DNA segments.

Figure 4A:
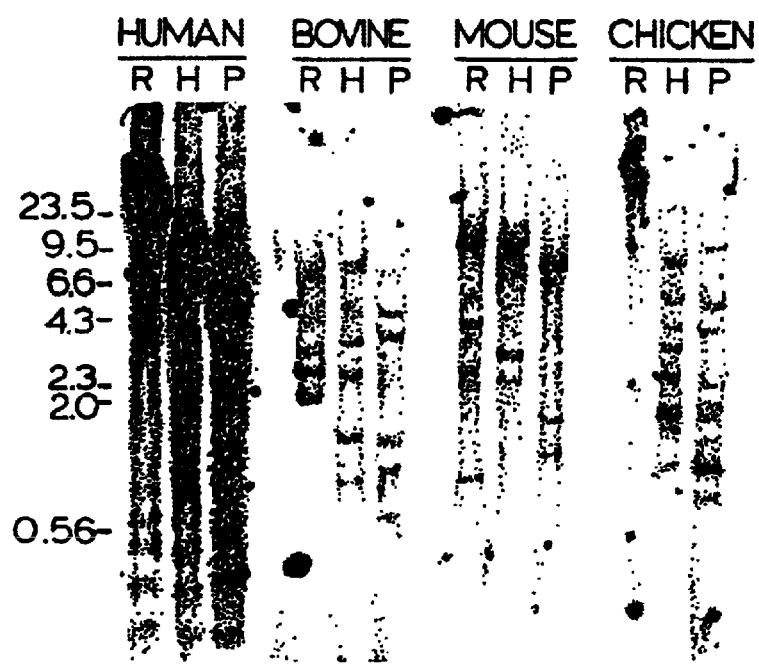
FIGS. 4A, 4B and 4C show the detection of conserved nucleotide sequences by cross-species hybridization.
Figure 4B:
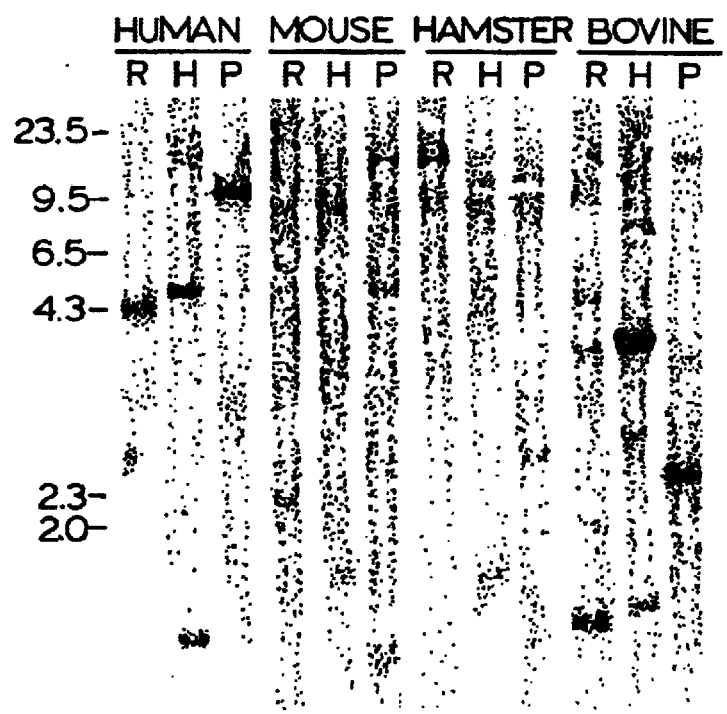
Figure 4C:
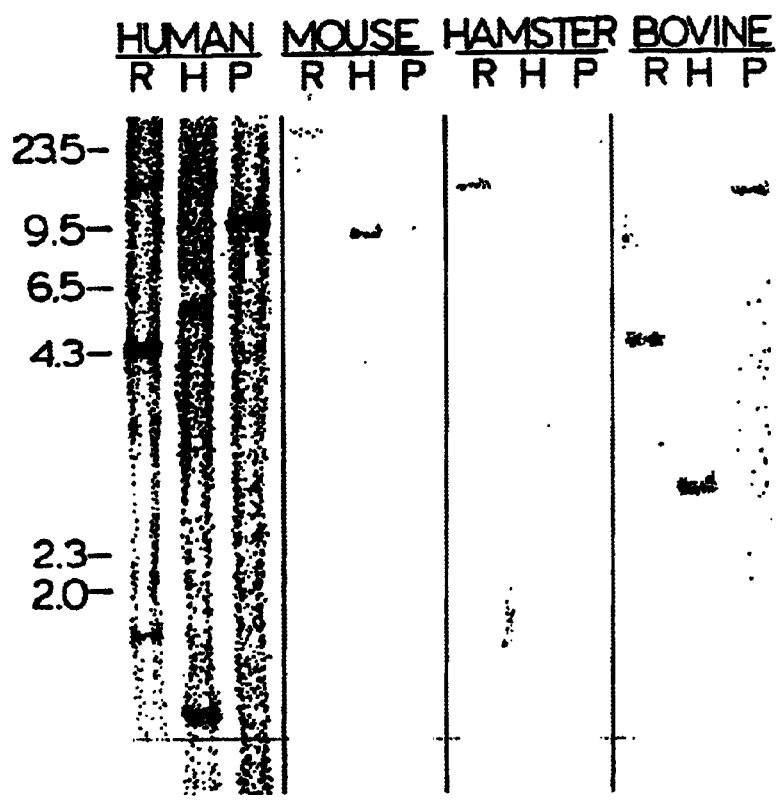

Cross-species hybridization showed strong sequence conservation between human and bovine DNA when CF14, E4.3 and H1.6 were used as probes, the results of which are shown in FIGS. 4A, 4B and 4C.

Figure 4D:
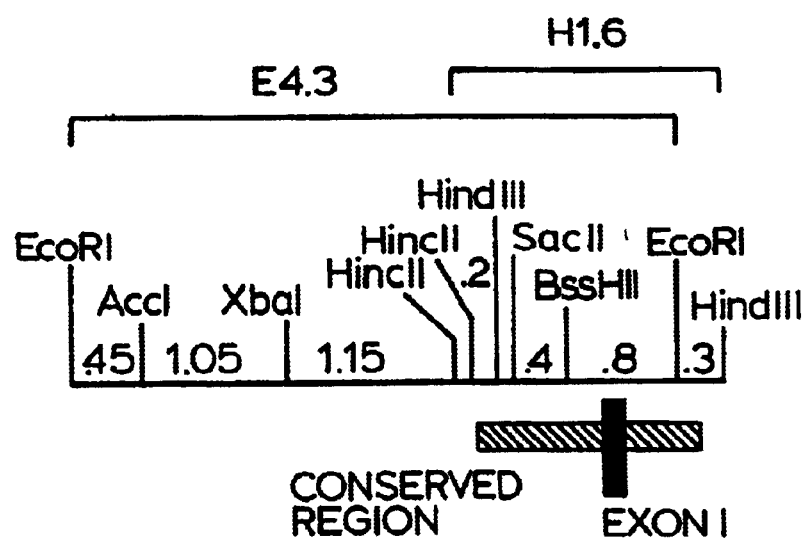
FIG. 4D is a restriction map of overlapping segments of probes E4.3 and H1.6.
Figure 5:
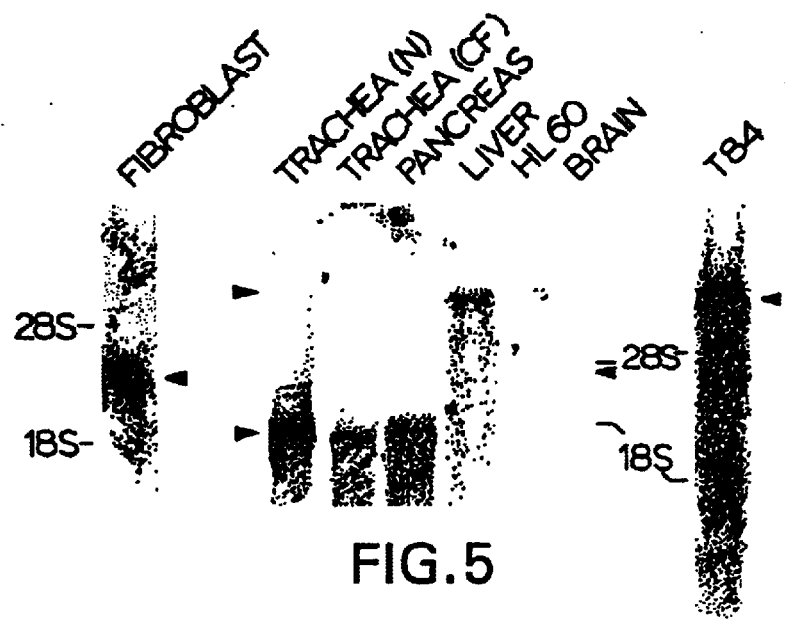
FIG. 5 is an RNA blot hybridization analysis, using genomic and cDNA probes. Hybridization to fibroblast, trachea (normal and CF), pancreas, liver, HL60, T84, and brain RNA is shown.

Human, bovine, mouse, hamster, and chicken genomic DNAs were digested with Eco RI (R), Hind III (H), and Pst I (P), electrophoresed, and blotted to ZETABIND™ (BioRad). The hybridization procedures of Rommens et al, 1988, supra, were used with the most stringent wash at 55° C., 0.2×SSC, and 0.1% SDS. The probes Used for hybridization, in FIGS. 4A–4C, included: (A) entire cosmid CF14, (B) E4.3, (C) H1.6. In the schematic of FIG. 4D, the shaded region indicates the area of cross-species conservation.

The fact that different subsets of bands were detected in bovine DNA with these two overlapping DNA segments (H1.6 and E4.3) suggested that the conserved sequences were located at the boundaries of the overlapped region (FIG. 4D). When these DNA segments were used to detect RNA transcripts from a variety of tissues, no hybridization signal was detected. In an attempt to understand the cross-hybridizing region and to identify possible open reading frames, the DNA sequences of the entire H1.6 and part of the E4.3 fragment were determined. The results showed that, except for a long stretch of CG-rich sequence containing the recognition sites for two restriction enzymes (Bss HII and Sac II), often found associated with undermethylated CpG islands, there were only short open reading frames which could not easily explain the strong cross-species hybridization signals.

Figure 6:
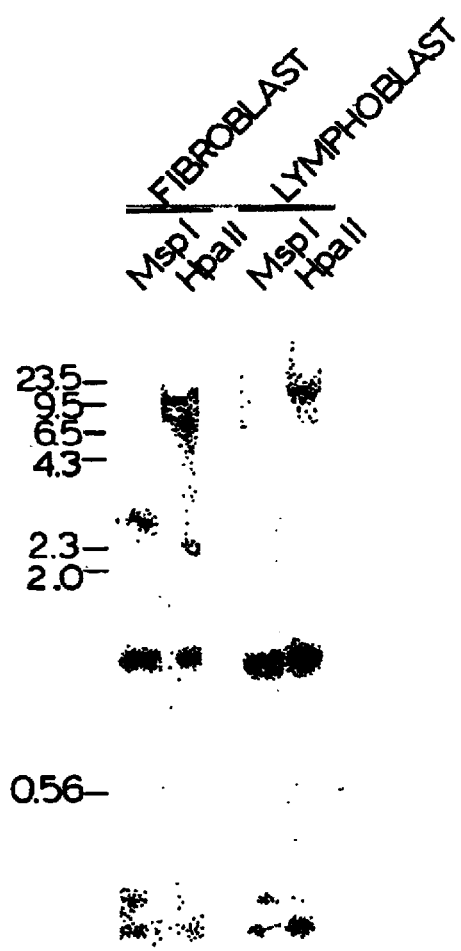
FIG. 6 is the methylation status of the E4.3 cloned region at the 5' end of the CF gene.

To examine the methylation status of this highly CpG-rich region revealed by sequencing, genomic DNA samples prepared from fibroblasts and lymphoblasts were digested with the restriction enzymes Hpa II and Map I and analyzed by gel blot hybridization. The enzyme Hpa II cuts the DNA sequence 5'-CCGG-3' only when the second cytosine is unmethylated, whereas Msp I cuts this sequence regardless of the state of methylation. Small DNA fragments were generated by both enzymes, indicating that this CpG-rich region is indeed undermothylated in genomic DNA. The gel-blot hybridization with the E4.3 segment (FIG. 6) reveals very small hybridizing fragments with both enzymes, indicating the presence of a hypomethylated CpG island.

The above results strongly suggest the presence of a coding region at this locus. Two DNA segments (E4.3 and H1.6) which detected cross-species hybridization signals from this area were used as probes to screen cDNA libraries made from several tissues and cell types.

cDNA libraries from cultured epithelial calls were prepared an follows. Sweat gland calls derived from a non-CF individual and from a CF patient were grown to first passage an described (G. Collie et al, *In Vitro Cell. Dev. Biol.* 21, 592,1985). The presence of outwardly rectifying channels was confirmed in these cells (J. A. Tabcharani, T. J. Jensen, J. R. Riordan, J. W. Hanrahan, *J. Hemb. Biol.*, in press) but the CF cells were insensitive to activation by cyclic AMP (T. J. Jensen, J. W. Hanrahan, J. A. Tabcharani, M. Buchwald and J. R. Riordan, a *Pediatric Pulmonology*, Supplement 2, 100, 1988). RNA was isolated from then by the method of J. M. Chirgwin et al (*Biochemistry* 18, 5294, 1979). Poly A+RNA was selected (H. Aviv and P. Leder, *Proc. Natl. Acad. Sci. USA* 69, 1408, 1972) and used as template for the synthesis of cDNA with oligo (dT) 12–18 as a primer. The second strand was synthesized according to Gubler and Hoffman (*Gene* 25, 263, 1983). This was methylated with Eco RI methylase and ends were made flush with T4 DNA polymerase. Phosphorylated Eco RI linkers were ligated to the cDNA and restricted with Eco RI. Removal of excess linkers and partial size fractionation was achieved by Biogel A-50 chromatography. The cDNAs were then ligated into the Eco RI Site of the commercially available LAMDA ZAP. Recombinants were packaged and propagated in *E. coli* BB4. Portions of the packaging mixes were amplified and the remainder retained for screening prior to amplification. The same procedures were used to construct a library from RNA isolated from preconfluent cultures of the T-84 colonic carcinoma call line (Dharmsathaphorn, K. at al. *Am. J. Physiol.* 246, G204,1984). The numbers of independent recombinants in the three libraries were: $2 \times 10^6$ for the non-CF sweat gland cells, $4.5 \times 10^6$ for the CF sweat gland cells and $3.2 \times 10^6$ from T-84 calls. These phages were plated at 50,000 per 15 c plate and plaque lifts made using nylon membranes (Biodyne) and probed with DNA fragments labelled with $^{32}P$ using DNA polymerase I and a random mixture of oligonucleotides as primer. Hybridization conditions were according to G. M. Wahl and S. L. Berger (Meth. Enzymol. 152,415, 1987) BLUESCRIPT™ plasmids were rescued from plaque purified clones by excision with M13 helper phage. The lung and pancreas libraries were purchased from Clontech lab Inc. with reported sizes of $1.4 \times 10^6$ and $1.7 \times 10^6$ independent clones.

After screening 7 different libraries each containing $1 \times 10^5 - 5 \times 10^6$ independent clones, 1 single clone (identified as 10-1) was isolated with H1.6 from a cDNA library mad from the cultured sweat gland epithelial cells of an unaffected (non-CF) individual.

DNA sequencing analysis showed that 10-1 contain d an insert of 920 bp in size and one potential, long open reading frame (ORF). Since one end of the sequence shared perfect sequence identity with H1.6, it was concluded that the cDNA clone was probably derived from this region. The DNA sequence in common was, however, only 113 bp long (see FIGS. 1A–1H and 7A–7B). As detailed below, this sequence in fact corresponded to the 5'-most exon of the putative CF gene. The abort sequence overlap thus explained the weak hybridization signals in library screening and inability to detect transcripts in RNA gal-blot analysis. In addition, the orientation of the transcription unit was tentatively established on the basis of alignment of the genomic DNA sequence with the presumptive ORF of 10-1.

Since the corresponding transcript was estimated to be approximately 6500 nucleotides in length by RNA gel-blot hybridization experiments, further cDNA library screening was required in order to clone the remainder of the coding-region. As a result of several successive screenings with cDNA libraries generated from the colonic carcinoma cell line T84, normal and CF sweat gland cells, pancreas and adult lungs, 18 additional clones were isolated (FIGS. 7A–7B, an subsequently discussed in greater detail). DNA sequence analysis revealed that none of these cDNA clones corresponded to the length of the observed transcript, but it was possible to derive a consensus sequent based on overlapping regions. Additional cNA clones corresponding to the 5' and 3' ends of the transcript were derived from 5' and 2' primer-extension experiments. Together, these clones span a total of about 6.1 kb and contain an ORF capable of encoding a polypeptide of 1480 amino acid residues (FIGS. 1A–1H).

Figure 7A:
FIGS. 7A–7B are a restriction map of the CFTR cDNA showing alignment of the cDNA to the genomic DNA fragments.
Figure 7B:
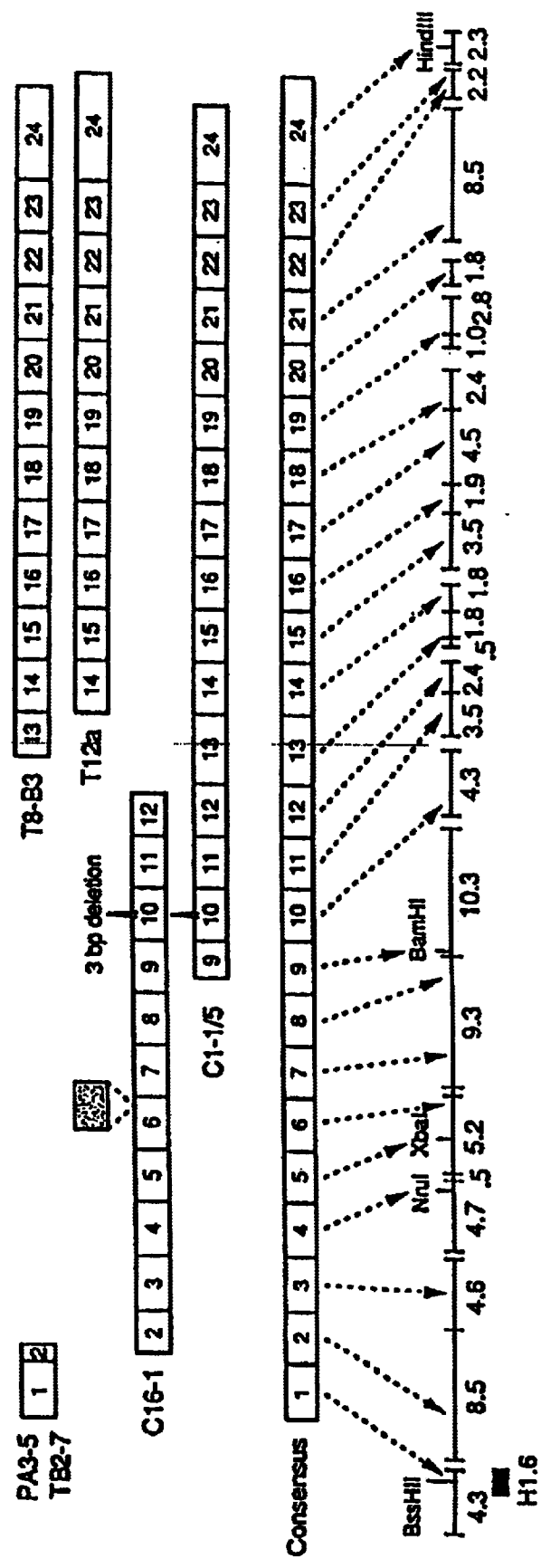

It was unusual to observe that most of the cDNA clones isolated hers contained sequence insertions at various locations of the restriction map of FIGS. 7A–7B. The map details the genomic structure of the CF gene. Exon/intron boundaries are given where all cDNA clones isolated are schematically represented on the upper half of the figure. Many of these extra sequences clearly corresponded to intron regions reversely transcribed during the construction of the cDNA, as revealed upon alignment with genomic DNA sequences.

Since the number or recombinant cDNA clones for the CF gene detected in the library screening was much less than would have been expected from the abundance of transcript estimated from RNA hybridization experiments, it seemed probable that the clones that contained aberrant structures were preferentially retained while the proper clones were lost during propagation. Consistent with this interpretation, poor growth was observed for the majority of the recombinant clones isolated in this study, regardless of the vector used.

The procedures used to obtain the 5' and 3' ends of the cDNA wore similar to those described (M. Frohman at al, *Proc. Nat. Acad. Sci*, USA, 85, 8998–9002, 1988). For the 5' end clones, total pancreas and T84 poly A+ RNA samples were reverse transcribed using a primer, (10b), which is specific to axon 2 similarly as has been described for the primer extension reaction except that radioactive tracer was included in the reaction. The fractions collected from an agarose bead column of the first strand synthesis were assayed by polymerase chain reaction (PCR) of eluted fractions. The oligonucleotides used were within the 10-1 sequence (145 nucleotides apart) just 5' of the extension primer. The earliest fractions yielding PCR product were pooled and concentrated by evaporation and subsequently tailed with terminal deoxynucleotidyl transferase (BRL Labs.) and dATP as recommended by the supplier (BRL Labs). A second strand synthesis was then carried out with Taq Polymerase (Cetus, AmpliTaq) using an oligonucleotide containing a tailed linker sequence 5'CGGAATTCTCGAGATC$(T)_{12}$3'. (SEQ ID NO:1)

Amplification by an anchored (PCR) experiment using the linker sequence and a primer just internal to the extension primer which possessed the Eco RI restriction site at its 5' and was then carried out. Following restriction with the enzymes Eco RI and Bgl II and agarose gel purification size selected products were cloned into the plasmid) BLUESCRIPT KS available from Stratagene by standard procedures (Maniatis et al, supra). Essentially all of the recovered clones contained inserts of less than 350 nucleotides. To obtain the 3' end clones, first strand cDNA was prepared with reverse transcription of 2 µg T84 poly A+ RNA using the tailed linker oligonucleotide previously described with conditions similar to those of the primer extension. Amplification by PCR was then carried out with the linker oligonucleotide and three different oligonucleotides corresponding to known sequences of clone T16-4.5. A preparative scale reaction (2×100 ul) was carried out with one of these oligonucleotides with the sequence 5'ATGAAGTCCAAGGATTTAG3'. (SEQ ID NO. 2).

This oligonucleotide is approximately 70 nucleotides upstream of a Hind III site within the known sequence of T16-4.5. Restriction of the PCR product with Hind III and Xho 1 was followed by agarose gel purification to size select a band at 1.0 product was then cloned into the plasmid BLUESCRIPT KS available from Stratagene. Approximately 20% of the obtained clones hybridized to the 3' and portion of T16-4.5. 10/10 of plasmids isolated from these clones had identical restriction maps with insert sizes of approx. 1.2 kb. All of the PCR reactions were carried out for 30 cycles in buffer suggested by an enzyme supplier.

An extension primer positioned 157 nt from the 5'end of 10-1 clone was used to identify the start point of th putative CF transcript. The primer was end labeled with (32P)ATP at 5000 curies/mmole and T4 polynucleotide kinase and purified by spun column gel filtration. The radiolabeled primer was then annealed with 4-5 ug poly A+ RNA prepared from T-84 colonic carcinoma cells in 2×reverse transcriptase buffer for 2 hrs. at 60° C. Following dilution and addition of AMV reverse transcriptase (Life sciences, Inc.) incubation at 41° C. proceeded for 1 hour. The sample was then adjusted to 0.4M NaOH and 20 mM EDTA, and finally neutralized, with $NH_4OAc$, pH 4.6, phenol extracted, ethanol precipitated, redissolved in buffer with formamide, and analyzed on a polyacrylamide sequencing gel. Details of these methods have been described (*Meth. Enzymol.* 152, 1987, Ed. S. L. Berger, A. R. Kimmel, Academic Press, N.Y.).

Figure 10A:
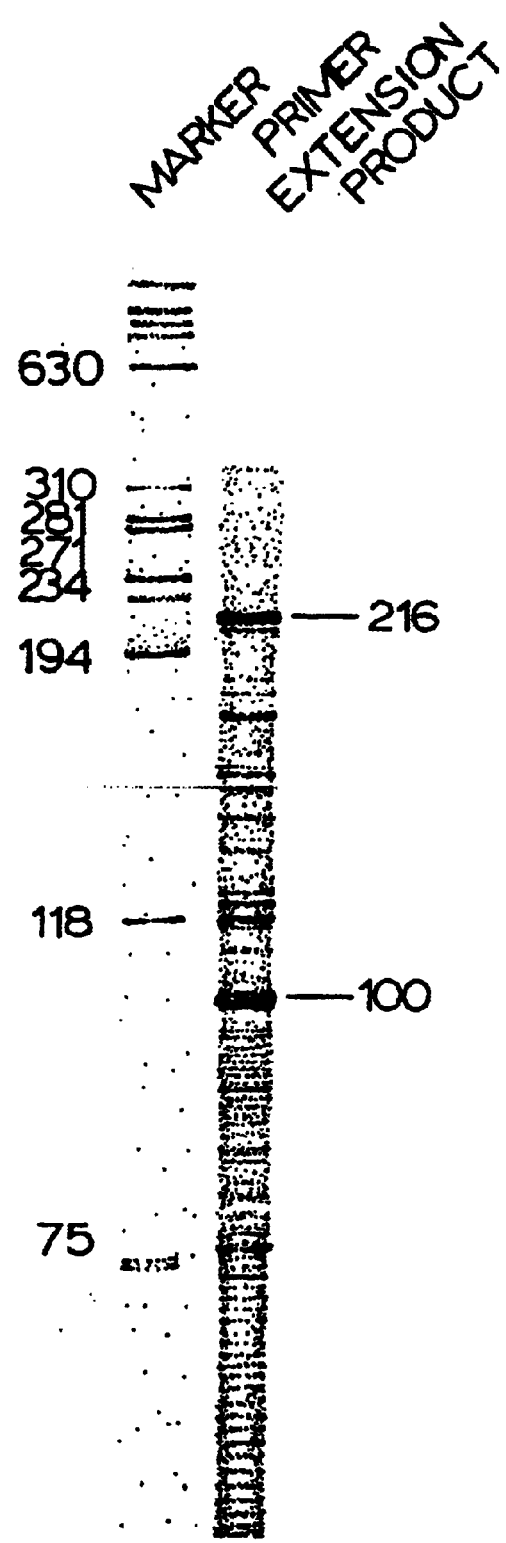
FIGS. 10A–10C are a primer extension experiment characterizing the 5' and 3' ends of the CFTR cDNA.
Figure 10B:
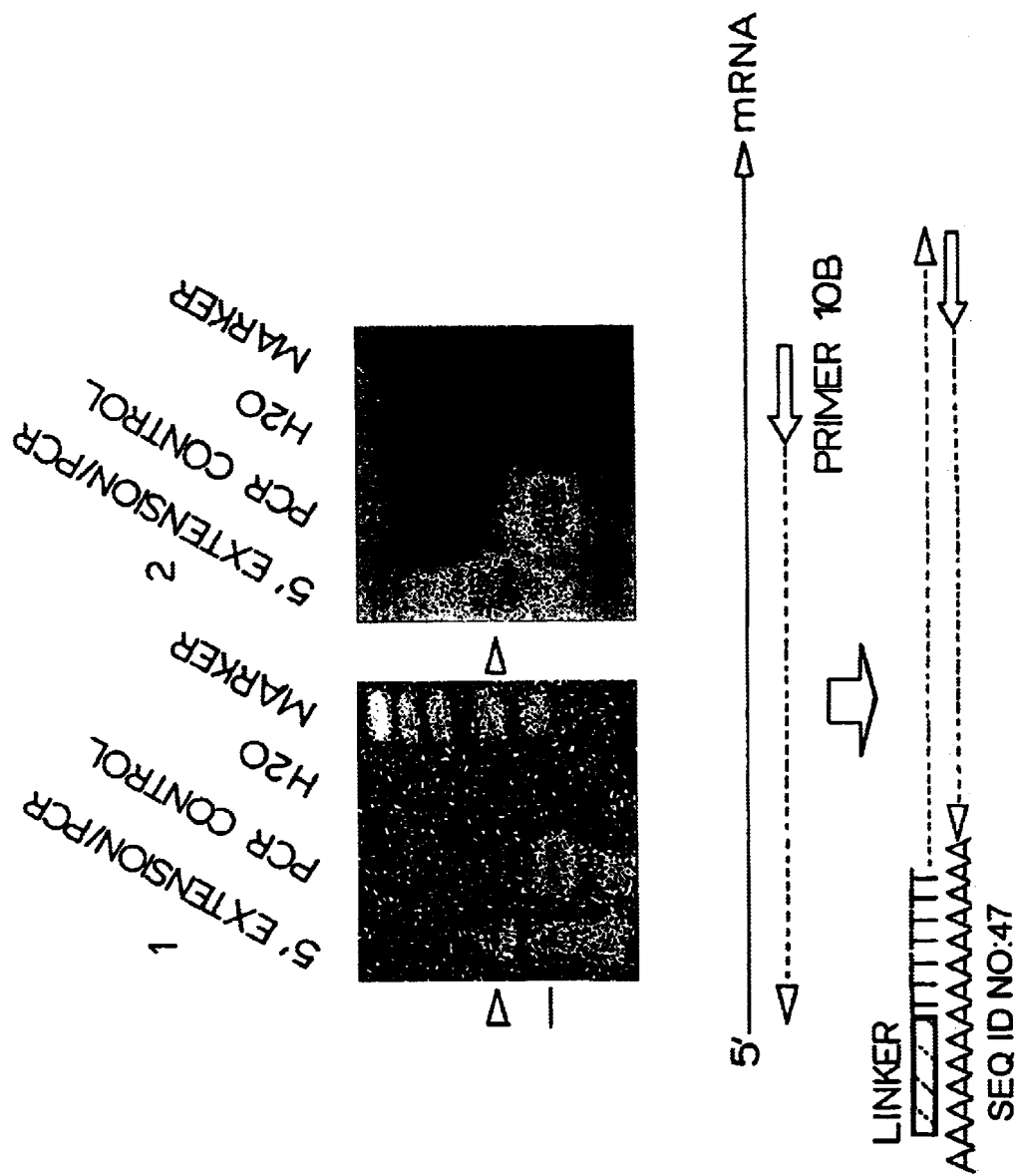

Results of the primer extension experiment using an extension oligonucleotide primer starting 157 nucleotides from the 5' end of 10-1 is shown in FIG. 10A. End labeled øX174 bacteriophage digested with Hae III (BRL Labs) is used as size marker. Two major products are observed at 216 and 100 nucleotides. The sequence corresponding to 100 nucleotides in 10-1 corresponds to a very GC rich sequence (11/12) suggesting that this could be a reverse transcriptase pause site. The 5' anchored PCR results are shown in FIGS. 10B. The 1.4% agarose gel shown on the left was blotted and transferred to ZETAPROBE™ membrane (Bio-Rad Lab). DNA gel blot hybridization with radiolabeled 10-1 is shown on the right. The 5' extension products are seen to vary in size from 170–280 nt with the major product at about 200 nucleotides. The PCR control lane shows a fragment of 145 nucleotides. It was obtained by using the test oligomers within the 10-1 sequence. The size markers shown correspond to sizes of 154, 220/210, 298, 344, 394 nucleotides (1 kb ladder purchased from BRL Lab).

Figure 10C:
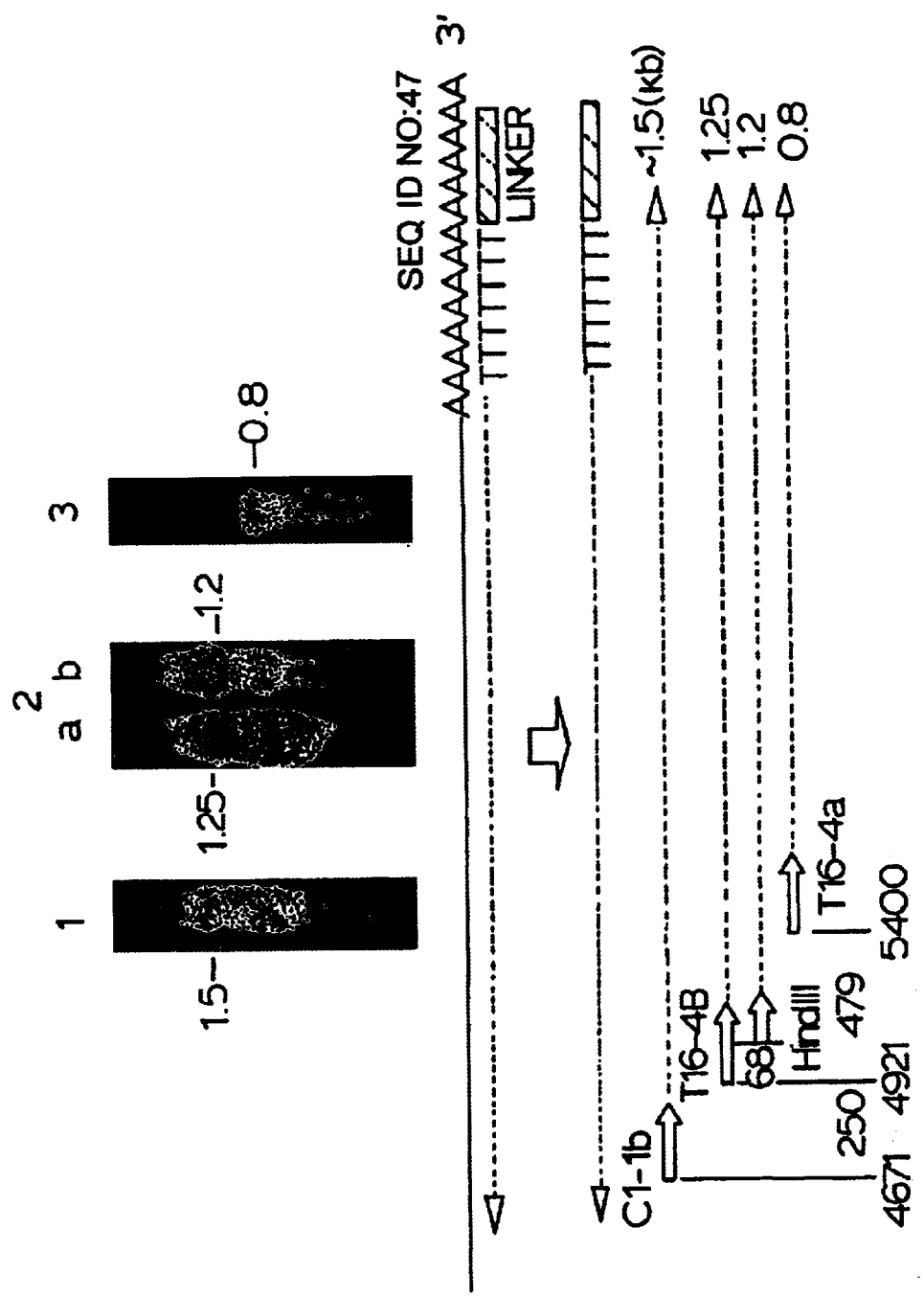

The schematic shown FIG. 10B outlines the procedure to obtain double stranded cDNA used for the amplification and cloning to generate the clones PA3-5 and TB2-7 shown in FIGS. 7A–7B. The anchored PCR experiments to characterize the 3'end are shown in FIG. 10C. As depicted in FIG. 10C, three primers whose relative position to each other were known were used for amplification with reversed transcribed T84 RNA as described. These products were separated on a 1% agarose gel and blotted onto nylon membrane as described above. DNA-blot hybridization with the 3' portion of the T16-4.5 clone yielded bands of sizes that corresponded to the distance between the specific oligomer used and the 3' end of the transcript. These bands in lanes 1, 2a and 3 are shown schematically below in FIG. 10C. The band in lane 3 is weak as only 60 nucleotides of this segment overlaps with the probe used. Also indicated in the schematic and as shown in the lane 2b is the product generated by restriction of the anchored PCR product to facilitate cloning to generate the THZ-4 clone shown in FIGS. 7A–7B.

DNA-blot hybridization analysis of genomic DNA digested with EcoRI and HindIII enzymes probed with portions of cDNAs spanning the entire transcript suggest that the gene contains at least 24 exons numbered as Roman numerals I through XXIV (see FIGS. 9A–9D). These correspond to the numbers 1 through 24 shown in FIGS. 7A–7B. The size of each band is given in kb.

In FIGS. 7A–7B, open boxes indicate approximate positions of the 24 exons which have been identified by the isolation of >22 clones from the screening of cDNA libraries and from anchored PCR experiments d sign d to clone the 5' and 3' ends. The lengths in kb of the Eco RI genomic fragments detected by each exon is also indicated. The hatched boxes in FIGS. 7A–7B indicate the presence of intron sequences and th stippled boxes indicate other sequences. Depicted in the lower left by the closed box is the relative position of the clone H1.6 used to detect the first cDNA clone 10-1 from among $10^6$ phage of the normal sweat gland library. As shown in FIGS. 4D and 7A–7B, the genomic clone H1.6 partially overlaps with an EcoRI fragment of 4.3 kb. All of the cDNA clones shown were hybridized to genomic DNA and/or were fine restriction mapped. Examples of the restriction sites occurring within the cDNAs and in the corresponding genomic fragments are indicated.

Figures 9A, 9B, 9C, 9D:
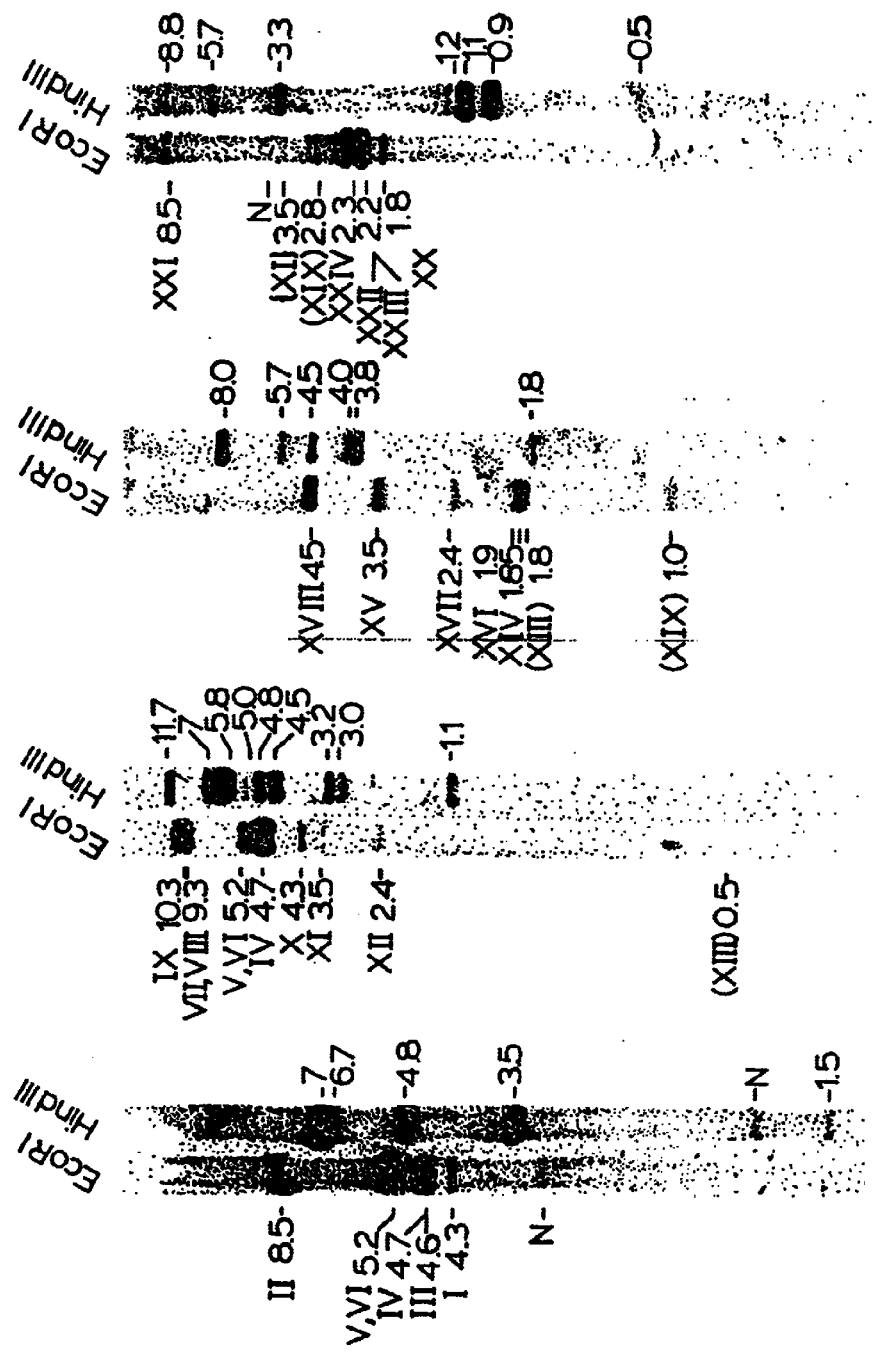
FIGS. 9A–9D are a DNA blot hybridization analysis depicting hybridization by the CFTR cDNA clones to genomic DNA digested with EcoRI and Hind III.

With reference to FIGS. 9A–9D, the hybridization analysis includes probes; i.e., cDNA clones 10-1 for FIG. 9A, T16-1 (3' portion) for FIG. 9B, T16-4.5 (central portion) for FIG. 9C and T16-4.5 (3' end portion) for FIG. 9D. In FIG. 9A, the cDNA probe 10-1 detects the genomic bands for exons I through VI. The 3' portion of T16-1 generated by NruI restriction detects exons IV through XIII as shown in FIG. 9B. This probe partially overlaps with 10-1. FIGS. 9C–9D, respectively, show genomic bands detected by the central and 3' end EcoRI fragments of the clone T16-4.5. Two EcoRI sites occur within the cDNA sequence and split exons XIII and XIX. As indicated by the exons in parentheses, two genomic EcoRI bands correspond to each of these exons. Cross hybridization to other genomic fragments was observed. These bands, indicated by N, are not of chromosome 7 origin as they did not appear in human-hamster hybrids containing human chromosome 7. The faint band in FIG. 9D indicated by XI in brackets is believed to be caused by the cross-hybridization of sequences due to internal homology with th cDNA.

Since 10-1 detected a strong band on gel blot hybridization of RNA from the T-84 colonic carcinoma cell line, this cDNA was used to screen the library constructed from that source. Fifteen positives were obtained from which clones T6, T6/20, T11, T16-1 and T13-1 were purified and sequenced. Rescreening of the same library with a 0.75 kb Bam HI-Eco RI fragment from the 3' end of T16-l yielded T16-4.5. A 1.8 kb EcoRI fragment from the 3 end of T16-4.5 yielded T8-B3 and T12a, the latter of which contained a polyadenylation signal and tail. Simultaneously a human lung cDNA library was screened; many clones were isolated including those shown here with the prefix 'CDL'. A pancreas library was also screened, yielding clone CDPJ5.

To obtain copies of this transcript from a CF patient, a cDNA library from RNA of sweat gland epithelial cells from a patient was screened with the 0.75 kb Bam HI-Eco RI fragment from the 3' end of T16-1 and clones C16-1 and C1-1/5, which covered all but exon 1, were isolated. Theme two clones both exhibit a 3 bp deletion in exon 10 which is not present in any other clone containing that axon. Several clones, including CDLS26-1 from the lung library and T6/20 and T13-1 isolated from T84 were derived from partially processed transcripts. This was confirmed by genomic hybridization and by sequencing across the exon-intron boundaries for each clone. T11 also contained additional sequence at each end. T16-4.5 contained a small insertion near the boundary between exons 10 and 11 that did not correspond to intron sequence. Clones CDLS16A, 11a and 13a from the lung library also contained extraneous sequences of unknown origin. The clone C16-1 also contained a short insertion corresponding to a portion of the γ-transposon of *E. coli*; this element was not detected in the other clones. The 5' clones PA3-5, generated from pancreas RNA and TB2-7 generated from T84 RNA using the anchored PCR technique have identical sequences except for a single nucleotide difference in length at the 5' end as shown in FIGS. 1A–1H. The 3' clone, THZ-4 obtained from T84 RNA contains the 3' sequence of the transcript in concordance with the genomic sequence of this region.

A combined sequence representing the presumptive coding region of the CF gene was generated from overlapping cDNA clones. Since most of the cDNA clones were apparently derived from unprocessed transcripts, further studies were performed to ensure the authenticity of the combined sequence. Each cDNA clone was first tested for localization to chromosome 7 by hybridization analysis with a human-hamster somatic call hybrid containing a single human chromosome 7 and pulsed field gel electrophoresis. Fine restriction enzyme mapping was also performed for each clone. While overlapping regions were clearly identifiable for most of the clones, many contained regions of unique restriction patterns.

To further characterize these cDNA clones, they were used as probes in gel hybridization experiments with EcoRI- or HindIII-digested human genomic DNA. As shown in FIGS. 9A–9D, five to six different restriction fragments could be detected with the 10-1 cDNA and a similar number of fragments with other cDNA clones, suggesting the presence of multiple exons for the putative CF gene. The hybridization studies also identified those cDNA clones with unprocessed intron sequences as they showed preferential hybridization to a subset of genomic DNA fragments. For the confirmed cDNA clones, their corresponding genomic DNA segments were isolated and the exons and exon/intron boundaries sequenced. As indicated in FIGS. 7A–7B, a total of 24 exons were identified. Based on this information and the results of physical mapping experiments, the gene locus was estimated to span 250 kb on chromosome 7.

2.6 The Sequence

Figure 11:
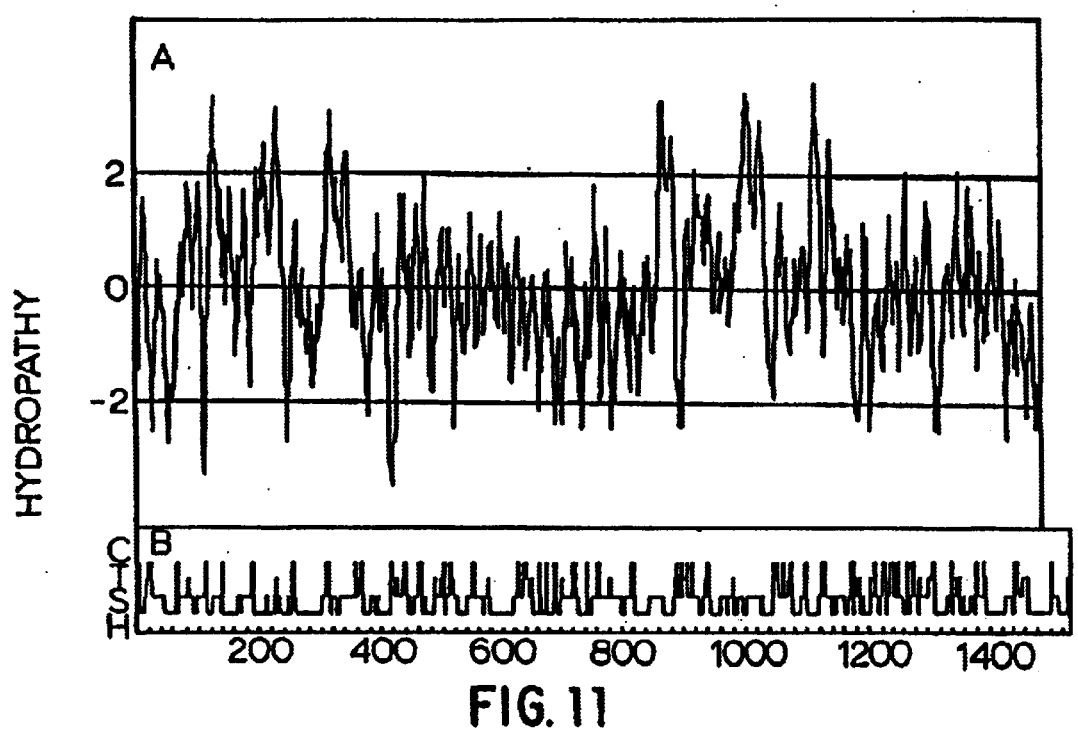
FIG. 11 is a hydropathy profile and shows predicted secondary structures of CFTR.

FIGS. 1A–1H show the nucleotide sequence of the cloned cDNA encoding CFTR together with the deduced amino acid sequence. The first base position corresponds to the first nucleotide in the 5' extension clone PA3-5 which is one nucleotide longer than TB2-7. Arrows indicate position of transcription initiation site by primer extension analysis. Nucleotide 6129 is followed by a poly(dA) tract. Positions of exon junctions are indicated by vertical lined. Potential membrane-spanning segments were ascertained using the algorithm of Eisenberg et al *J. Mol. Biol.* 179:125 (1984). Potential membrane-spanning segments an analyzed and shown in FIG. 11 are enclosed in boxes of FIGS. 1A–1H. In FIG. 11, the mean hydropathy index (Kyte and Doolittle, *J. Molec. Biol.* 157; 105, (1982)) of 9 residue peptides is plotted against the amino acid number. The corresponding positions of features of secondary structure predicted according to Garnier et al, (*J. Molec, Biol,* 157, 165 (1982)) are indicated in the lower panel. Amino acids comprising putative ATP-binding folds are underlined in FIGS. 1A–1H. Possible sites of phosphorylation by protein kinases A (PKA) or C (PKCi) are indicated by open and closed circles, respectively. The open triangle is over the 3 bp (CTT) which are deleted in CF (see discussion below). The cDNA clones in FIGS. 1A–1H were sequenced by the dideoxy chain termination method employing $^{35}$S labelled nucleotides by the DUPONT GENESIS 2000™ automatic DNA sequencer.

The combined cDNA sequence spans 6129 base pairs excluding the poly(A) tail at the and of the 3' untranslated region and it contains an ORF capable of encoding a polypeptide of 1480 amino acids (FIGS. 1A–1H). An ATG (AUG) triplet is present at the beginning of this ORF (base position 133–135). Since the nucleotide sequence surrounding this codon (5'-AGACCAUGCA-3') has the proposed features of the consensus sequence (CC) A/GCCAUG(G) of an eukaryotic translation initiation site with a highly conserved A at the −3 position, it is highly probable that this AUG corresponds to the first methionine codon for the putative polypeptide.

To obtain the sequence corresponding to the 5' end of the transcript, a primer-extension experiment was performed, as described earlier. As shown in FIG. 10A, a primer extension product of approximately 216 nucleotides could be observed suggesting that the 5' end of the transcript initiated approximately 60 nucleotides upstream of the end of cDNA clone 10-1. A modified polymerase chain reaction (anchored PCR) was then used to facilitate cloning of the 5'end sequences (FIG. 10B). Two independent 5' extension clones, one from pancreas and the other from T84 RNA, were characterized by DNA sequencing and were found to differ by only 1 base in length, indicating the most probable initiation site for the transcript as shown in FIGS. 1A–1H.

Since most of the initial cDNA clones did not contain a polyA tail indicative of the end of a mRNA, anchored PCR was also applied to the 3' end of the transcript (Frohman et al, 1988, supra) Three 3'-extension oligonucleotides were made to the terminal portion of the cDNA clone T-16–4.5. As shown in FIG. 10C, 3 PCR products of different sizes were obtained. All were consistent with the interpretation that the end of the transcript was approximately 1.2 kb downstream of the HindIII site at nucleotide position 5027 (see FIGS. 1A–1H). The DNA sequence derived from representative clones was in agreement with that of the T84 cDNA clone T12a (see FIGS. 1A–1H and 7A–7B) and the sequence of the corresponding 2.3 kb EcoRI genomic fragment.

3.0 Molecular Genetics of CF 3.1 Sites of Expression

Figure 8:
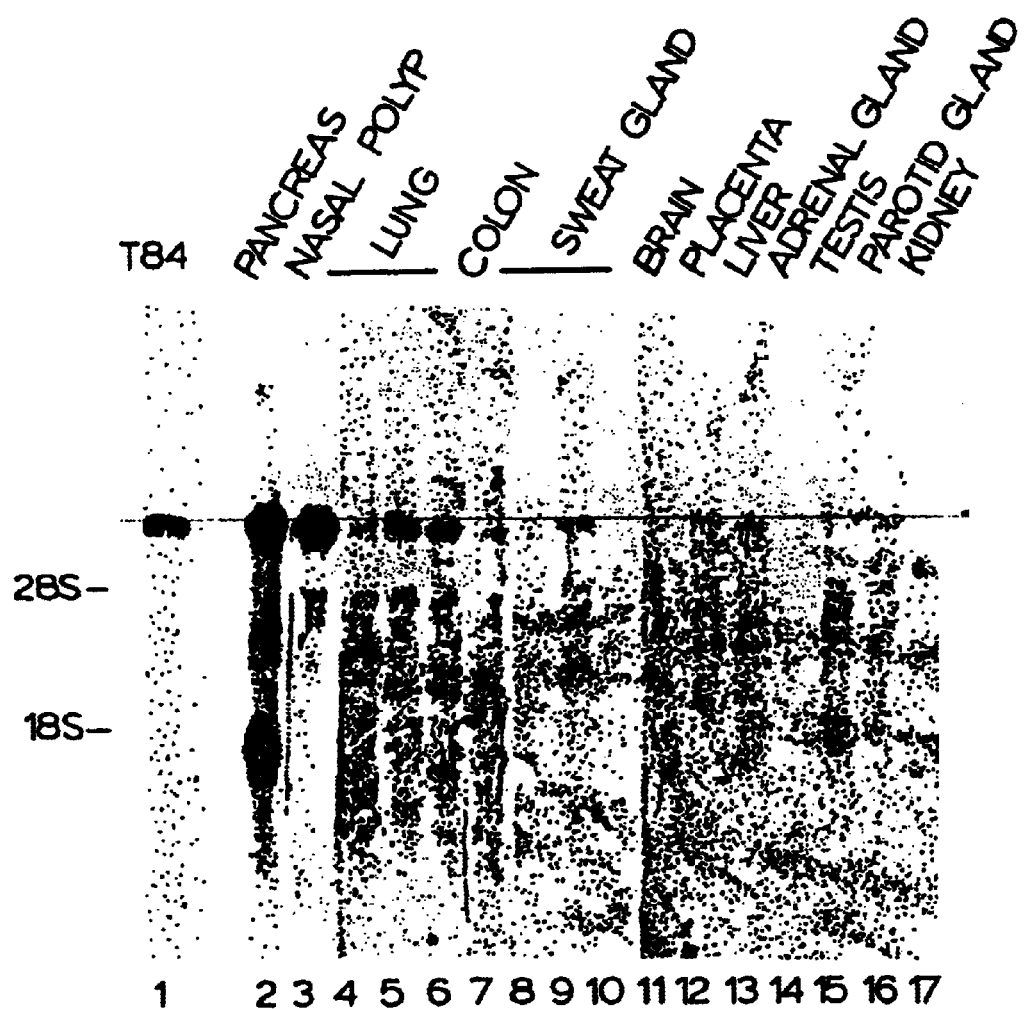
FIG. 8 is an RNA gel blot analysis depicting hybridization by a portion of the CFTR cDNA (clone 10-1) to a 6.5 kb mRNA transcript in various human tissues.

To visualize th transcript for the putative CF gene, RNA gel blot hybridization experiments were performed with the 10-1 cDNA as probe. The RNA hybridization results are shown in FIG. 8.

RNA samples were prepared from tissue samples obtained from surgical pathology or at autopsy according to methods previously described (A. M. Kimmel, S. L. Berger, eds. Meth. Enzymol. 152, 1987). Formaldehyde gels were transferred onto nylon membranes (ZETAPROBE™; BioRad Lab). The membranes were then hybridized with DNA probes labeled to high specific activity by the random priming method (A. P. Feinberg and B. Vogelstein, *Anal. Biochem.* 132, 6, 1983) according to previously published procedures (J. Rommens et al, *Am. J. H. Genet.* 43, 645–663, 1988). FIG. 8 shows hybridization by the cDNA clone 10-1 to a 6.5 kb transcript in the tissues indicated. Total RNA (10 µg) of each tissue, and Poly A+ RNA (1 µg) of the T84 colonic carcinoma cell line were separated on a 1% formaldehyde gel. The positions of the 28S and 18S rRNA bands are indicated. Arrows indicate the position of transcripts. Sizing was established by comparison to standard RNA markers (BRL Labs). HL60 is a human promyelocytic leukemia cell line, and T84 is a human colon cancer cell line.

Analysis reveals a prominent band of approximately 6.5 kb in Size in T84 cells. Similar, strong hybridization signals were also detected in pancreas and primary cultures of cells from nasal polyps, suggesting that the mature mRNA of the putative CF gene is approximately 6.5 kb. Minor hybridization signals, probably representing degradation products, were detected at the lower size ranges but they varied between the different experiments. Identical results were obtained with other cDNA clone as probes. Based on the hybridization band intensity and comparison with those detected for other transcripts under identical experimental conditions, it was estimated that the putative CF transcripts constituted approximately 0.01% of total mRNA in T84 cells.

A number of other tissues were also surveyed by RNA gel blot hybridization analysis in an attempt to correlate the expression pattern of the 10-1 gene and the pathology of CF. As shown in FIG. 8, transcripts, all of identical size, were found in lung, colon, sweat glands (cultured epithelial cells), placenta, liver, and parotid gland but the signal intensities in these tissues varied among different preparations and were generally weaker than that detected in the pancreas and nasal polyps. Intensity varied among different preparations, for example, hybridization in kidney was not detected in the preparation shown in FIG. 8, but can be discerned in subsequent repeated assays. No hybridization signals could be discerned in the brain or adrenal gland (FIG. 8), nor in skin fibroblast and lymphoblast cell lines.

In summary, expression of the CF gene appeared to occur in many or the tissues examined, with higher levels in those tissues severely affected in CF. While this epithelial tissue-specific expression pattern is in good agreement with the disease pathology, no significant difference has been detected in the amount or size of transcripts from CF and control tissues, consistent with the assumption that CF mutations are subtle changes at the nucleotide level.

3.2 The Manor of Mutation

Figure 17A:
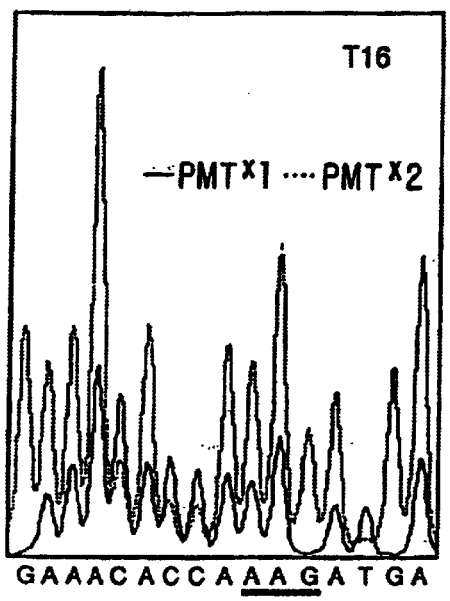
FIGS. 17A–17B are the DNA sequence around the F508 deletion.
Figure 17B:
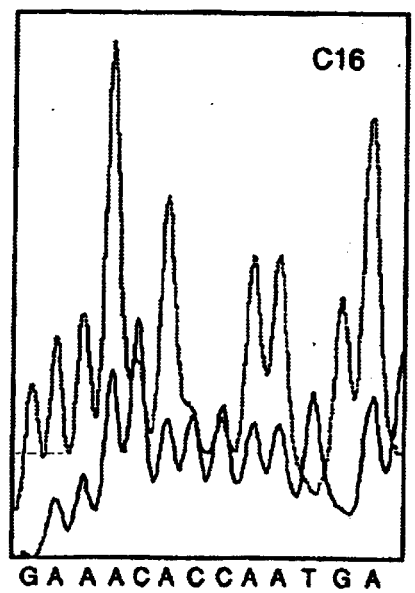
Figure 18A:
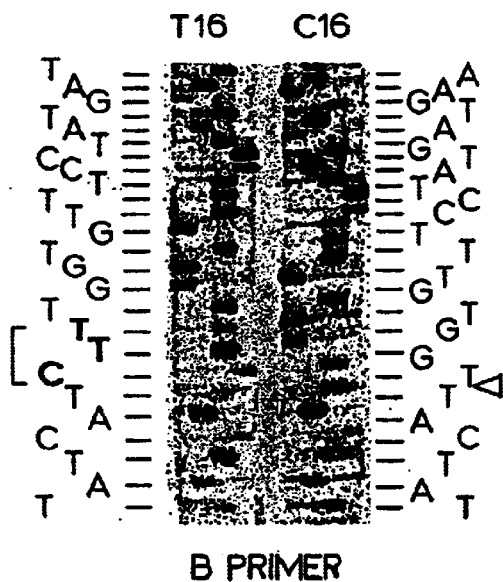
FIGS. 18A–18B are a representation of the nucleotide sequencing gel showing the DNA sequence at the F508 deletion.
Figure 18B:
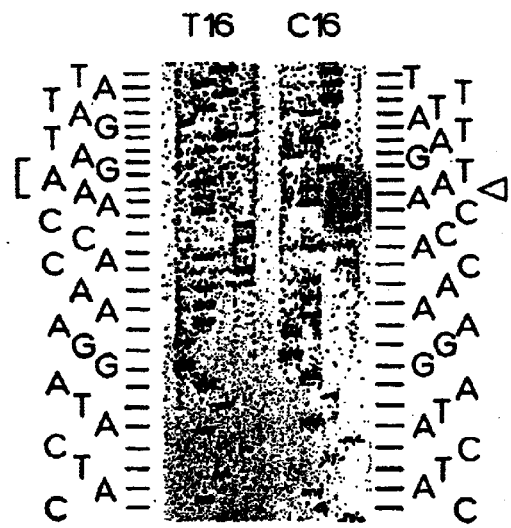

FIGS. 17A–17B shows the DNA sequence at the F508 deletion. On the left, the reverse complement of the sequence from base position 1649-1664 of the normal sequence (as derived from the cDNA clone T16). The nucleotide sequence is displayed as the output (in arbitrary fluorescence intensity units, y-axis) plotted against time x-axis) for each of the 2 photomultiplier tubes (PMT#1 and #2) of a DUPONT Genesis 2000™ DNA analysis system. The corresponding nucleotide sequence is shown underneath. On the right is the same region from a mutant sequence (as derived from the cDNA clone C16). Double-stranded plasmid DNA templates were prepared by the alkaline lysis procedure. Five µg of plasmid DNA and 75 ng of oligonucleotide primer were used in each sequencing reaction according to the protocol recommended by Dupont except that the annealing was done at 45° C. for 30 min and that the elongation/termination step was for 10 min at 42° C. The unincorporated fluorescent nucleotides were removed by precipitation of the DNA sequencing reaction product with ethanol in the presence of 2.5 M ammonium acetate at pH 7.0 and rinsed one time with 70% ethanol. The primer used for the T16-1 sequencing was a specific oligonucleotide 5'GTTGGCATGCTTTGATGACGCTTC3' spanning base position 1708-1731 and that for C16-1 was the universal primer SK for the BLUESCRIPT vector (Stratagene). FIGS. 18A–18B also show the DNA sequence around the F508 deletion, as determined by manual sequencing. The normal sequence from base position 1726-1651 (from cDNA T16-1) is shown beside the CF sequence (from cDNA C16-1). The left panel shows the sequences from the coding strands obtained with the B primer (5'GTTTTCCTGGAT-TATGCCTGGGCAC3') and the right panel those from the opposite strand with the D primer (5'GTTOCCATOCTTTGATGACGCTTC3[1]). The brakets indicate the three nucleotides in the normal that are absent in CF (arrowheads). Sequencing was performed as described in F. Sanger, S. Nicklen, A. R. Coulsen, *Proc. Nat. Acad. Sci. U.S.A.* 74: 5463 (1977).

To investigate the proportion of CF patients carrying this deletion (F508), genomic DNA samples from patients and their parents were each amplified with oligonucleotide primers flanking the mutation in a polymerase chain reaction and hybridized to $^{32}$P-labeled oligonucleotides specific for the normal and the putative mutant sequences (see FIGS. 2A–2G). The results of this analysis are shown in Table 2.

TABLE 2

DISTRIBUTION OF CF AND NON-CF(N) CHROMOSOMES WITH AND WITHOUT THE 3 bp DELETION a.

|  | CF chromosomes | N chromosomes |
|---|---|---|
| without the deletion | 69 | 198 |
| with the deletion | 145 | 0 |
| Total | 214 | 198 | b.

| | CF chromosomes | |
|---|---|---|
|  | with the 3 bp deletion | without the deletion |
| CF-PI | 62 | 24 |
| CF-PS | 5 | 9 |
| Unclassified | 78 | 36 |
| Total | 145 (68%) | 69 (32%) |

The data for the CF-PI (pancreatic insufficient) and CF-PS (pancreatic sufficient) chromosomes were derived from the CF families used in our linkage analysis. These families were originally selected without knowledge regarding PI or PS; the 15 CF-PS families subsequently identified were not included as part of this calculation. The unclassified CF chromosomes were obtained from the DNA Diagnosis Laboratory at the Hospital for sick Children in Toronto and for which pancreatic function data were not available.

It can be seen that 68% (145/214) of CF chromosomes in the general patient population had the F508 deletion (Table 2). In contrast none (0/198) of the N chromosomes had the deletion (Table 2; $x^2=207$, $p<10^{-57.5}$), suggesting that this sequence alteration is specific to CF and that it is the major mutation causing the disease. No recombination has been detected between the FS08 deletion and CF.

Other sequence differences were noted between the normal (T16-4.5) and CF (C1-1/5) cDNA clones. At base position 2629, T16-4.5 showed a C and C1-1/5 had a T, resulting in a Leu to Phe change at the amino acid level. At position 4555, the base was G in T16-4.5 but A in C1-1/5 (Val to Met). These findings are believed to represent sequence polymorphism. Specific oligonucleotide hybridization analysis of patient/family DNA will identify these as other possible mutations. Additional nucleotide differences were observed in the 3' untranslated regions between different cDNA clones and the genomic DNA sequence. Such differences in the sequences and as is appreciated, other sequence modifications are possible; for example, which differences are due to normal sequence polymorphisms and cloning artefacts, all of such differences being essentially equivalent to the sequence as described in FIGS. 1A–1H in terms of its function and its commercial applications.

The extensive genetic and physical mapping data have directed molecular cloning studies to focus on a small segment of DNA on chromosome 7. Because of the lack of chromosome deletions and rearrangements in CF and the lack of a well-developed functional assay for the CF gene product, the identification of the CF gene required a detailed characterization of the locus itself and comparison between the CF and normal (N) alleles. Random, phenotypically normal, individuals could not be included as controls in the comparison due to the high frequency of symptomless carriers in the population. As a result, only parents of CF patients, each of whom by definition carries an N and a CF chromosome, were suitable for the analysis. Moreover, because of the strong allelic association observed between CF and some of the closely linked DNA markers, it was necessary to exclude the possibility that sequence differences detected between N and CF were polymorphisms associated with the disease locus.

3.3. Identification of RFLPs and Family Studies

Figure 14:
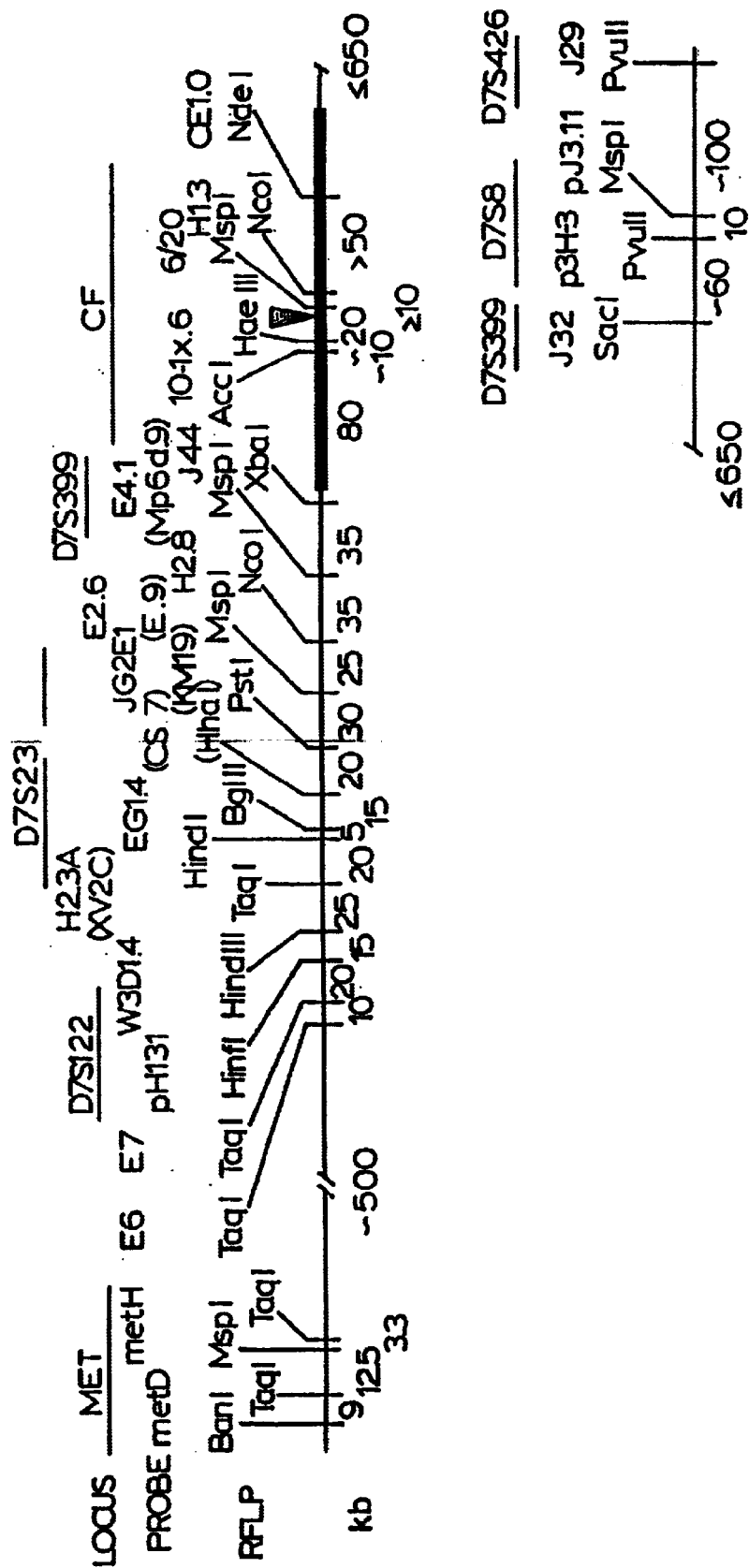
FIG. 14 is a schematic diagram of the restriction fragment length polymorphisms (RFLP's) closely linked to the CF gene where the inverted triangle indicates the location of the F508 3 base pair deletion.

To determine the relationship of each of the DNA segments isolated from th chromosome walking and jumping experiments to CF, restriction fragment length polymorphisms (RFLPs) were identified and used to study families where crossover events had previously been detected between CF and other flanking DNA markers. As shown in FIG. 14, a total of 18 RFLPs were detected in the 500 kb region; 17 of them (from E6 to CE1.0) listed in Table 3; come of them correspond to markers previously reported.

Five of the RFLPs, namely 10-1X.6, T6/20, H1.3 and CE1.0, were identified with cDNA and genomic DNA probes derived from the putative C? gene. The RFLP data are presented in Table 3, with markers in the MET and D7S8 regions included for comparison. The physical distances between these markers as well as their relationship to the MET and D7S8 regions are shown in FIG. 14.

TABLE 3

RFLPs ASSOCIATED WITH THE CF GENE

| Probe name | Enzyme | Frag-length | N[a] | CF-PI[a] | A[b] | *[c] | Reference |
|---|---|---|---|---|---|---|---|
| metD | BanI | 7.6 (kb) | 28 | 48 | 0.60 | 0.10 | J. E. Spence et al, Am. J. Hum. Genet 39:729 (1986) |
|  |  | 6.8 | 59 | 25 |  |  |  |
| metD | TaqI | 6.2 | 74 | 75 | 0.66 | 0.06 | R. White et al, Nature 318:382 (1985) |
|  |  | 4.8 | 19 | 4 |  |  |  |
| metH | TaqI | 7.5 | 45 | 49 | 0.35 | 0.05 | White et al, supra |
|  |  | 4.0 | 38 | 20 |  |  |  |
| E6 | TaqI | 4.4 | 58 | 62 | 0.45 | 0.06 | B. Keren et al, Am. J. Hum. Genet. 44: 827 (1989) |
|  |  | 3.6 | 42 | 17 |  |  |  |
| E7 | TaqI | 3.9 | 40 | 16 | 0.47 | 0.07 |  |
|  |  | 3 + 0.9 | 51 | 57 |  |  |  |

TABLE 3-continued

RFLPs ASSOCIATED WITH THE CF GENE

| Probe name | Enzyme | Frag-length | N[a] | CF-PI[a] | A[b] | *[c] | Reference |
|---|---|---|---|---|---|---|---|
| pH131 | HinfI | 0.4 | 81 | 33 | 0.73 | 0.15 | J. M. Rommens et. al, Am. J. Hum. Genet. 43:645 (1988) |
|  |  | 0.3 | 18 | 47 |  |  |  |
| W3D1.4 | HindIII | 20 | 82 | 33 | 0.68 | 0.13 | B. Kerem et al, supra |
|  |  | 10 | 22 | 47 |  |  |  |
| H2.3A | TaqI | 2.1 | 39 | 53 | 0.64 | 0.09 | X. Estivill et al, Nature 326:840 (1987); X. Estivill et al, Genomics 1:257 (1987) |
| (XV2C) |  | 1.4 | 37 | 11 |  |  |  |
| EG1.4 | HincII | 3.8 | 31 | 69 | 0.89 | 0.17 |  |
|  |  | 2.8 | 56 | 7 |  |  |  |
| BG1.4 | BgII | 20 | 27 | 69 | 0.89 | 0.18 |  |
|  |  | 15 | 62 | 9 |  |  |  |
| JG2E1 | PstI | 7.8 | 69 | 10 | 0.88 | 0.18 | X. Estivill et al supra and B. Kerem et al supra |
| (KM19) |  | 6.6 | 30 | 70 |  |  |  |
| E2.6/E.9 | MspI | 13 | 34 | 6 | 0.85 | 0.14 |  |
|  |  | 8.5 | 26 | 55 |  |  |  |
| H2.8A | NcoI | 25 | 22 | 55 | 0.87 | 0.18 |  |
|  |  | 8 | 52 | 9 |  |  |  |
| E4.1 | MspI | 12 | 37 | 8 | 0.77 | 0.11 | G. Romeo, personal communication |
| (Mp6d9) |  | 8.5 + 3.5 | 38 | 64 |  |  |  |
| J44 | XbaI | 15.3 | 40 | 70 | 0.86 | 0.13 |  |
|  |  | 15 + .3 | 44 | 6 |  |  |  |
| 10-1X.6 | AccI | 6.5 | 67 | 15 | 0.90 | 0.24 |  |
|  |  | 3.5 + 3 | 14 | 60 |  |  |  |
| 10-1X.6 | HaeIII | 1.2 | 14 | 61 | 0.91 | 0.25 |  |
|  |  | .6 | 72 | 15 |  |  |  |
| T6/20 | MspI | 8 | 56 | 66 | 0.51 | 0.54 |  |
|  |  | 4.3 | 21 | 8 |  |  |  |
| H1.3 | NcoI | 2.4 | 53 | 7 | 0.87 | 0.15 |  |
|  |  | 1 + 1.4 | 35 | 69 |  |  |  |
| CE1.0 | NdeI | 5.5 | 81 | 73 | 0.41 | 0.03 |  |
|  |  | 4.7 + 0.8 | 8 | 3 |  |  |  |
| J32 | SacI | 15 | 21 | 24 | 0.17 | 0.02 | M. C. Iannuzi et al Am. J. Genet. 44: 695 (1989) |
|  |  | 6 | 47 | 38 |  |  |  |
| J3.11 | MspI | 4.2 | 36 | 38 | 0.29 | 0.04 | B. J. Wainright et al, Nature 318:384 (1985) |
|  |  | 1.8 | 62 | 36 |  |  |  |
| J29 | PvuII | 9 | 26 | 36 | 0.36 | 0.06 | M. C. Iannuzi et al, supra |
|  |  | 6 | 55 | 36 |  |  |  |

NOTES FOR TABLE 3
(a) The number of N and CF-PT (CF with pancreatic insufficiency) chromosomes were derived from the parents in the families used in linkage analysis (Tsui et al, *Cold Spring Harbor Symp. Quant. Biol.* 51:325 (1986)).
(b) Standardized association (A), which is less influenced by the fluctuation of DNA marker allele distribution among the N chromosomes, is used here for the comparison Yule's association coefficient $A=(ad-bc)/(ad+bc)$, where a, b, c, and d are the number of N chromosomes with DNA marker allele 1, CF with 1, N with 2, and CF with 2 respectively, Relative risk can be calculated using the relationship $RR=(1+A)/(1-A)$ or its reverse.
(c) Allelic association (*), calculated according to A. Chakravarti et al, *Am. T. Hum, Genet.* 36:1239, (1984) assuming the frequency of 0.02 for CF chromosomes in the population is included for comparison.

Because of the small number of recombinant families available for the analysis, as was expected from the close distance between the markers studied and CF, and the possibility of misdiagnosis, alternative approaches were necessary in further fine mapping of the CF gone.

3.4 Allelic Association

Allelic association (linkage disequilibrium) has been detected for many closely linked DNA markers. While the utility of using allelic association for measuring genetic distance in uncertain, an overall correlation has been observed between CF and the flanking DNA markers. A strong association with CF was noted for the closer DNA markers, D7S23 and D7S122, whereas little or no association was detected for the more distant markers MET, D7S8 or D7S424 (see FIGS. 1A–1H).

As shown in Table 3, the degree of association between DNA markers and CF (as measured by the Yule's association coefficient) increased from 0.35 for math and 0.17 for J32 to 0.91 for 10-1X.6 (only CF-PI patient families were used in the analysis as they appeared to be genetically more homogeneous than CF-PS). The association coefficients appeared to be rather constant over the 300 kb from EG1.4 to H1.3; the fluctuation detected at several locations, most notably at H2.3A, E4.1 and T6/20, were probably due to the variation in the allelic distribution among the N chromosomes (see Table 2). These data are therefore consistent with the result from the study of recombinant families (see FIG. 14). A similar conclusion could also be made by inspection of the extended DNA marker haplotypes associated with the CF chromosomes (see below). However, the strong allelic association detected over the large physical distance between EG1.4 and H1.3 did not allow further refined mapping of the CF gene. Since J44 was the last genomic DNA clone isolated by chromosome walking and jumping before a cDNA clone was identified, the strong allelic association detected for the JG2E1-J44 interval prompted us to search for candidate gene sequences over this entire interval. It is of interest to note that the highest degree of allelic association was, in fact, detected between CF and the 2 RFLPs detected by 10-1X.6, a region near the major CF mutation.

Table 4 shows pairwise allelic association between DNA markers closely linked to CF. The average number of chromosomes used in these calculations was 75–80 and only chromosomes from CF-PI families were used in scoring CF chromosomes. Similar results were obtained when Yul's standardized association (A) was used).

TABLE 4

| | N chromosomes | | | | | | | | | | |
|---|---|---|---|---|---|---|---|---|---|---|---|
| | metH | metD | E6 | E7 | pH131 | W3D1.4 | H2.3A | EG1.4 | | JG2E1 | E2.6 |
| CF chromosomes | BanI | TaqI | TaqI | TaqI | TaqI | HindI | HdIII | TaqI | HcII | BgII | PstI | MspI |
| metD BanI | — | 0.35 | 0.49 | 0.04 | 0.04 | 0.05 | 0.07 | 0.27 | 0.06 | 0.06 | 0.07 | 0.14 |
| metD TaqI | 0.21 | — | 0.41 | 0.13 | 0.15 | 0.02 | 0.01 | 0.02 | 0.09 | 0.15 | 0.11 | 0.07 |
| metH TaqI | 0.81 | 0.14 | — | 0.01 | 0.05 | 0.06 | 0.06 | 0.24 | 0.05 | 0.06 | 0.07 | 0.13 |
| E6 TaqI | 0.11 | 0.30 | 0.00 | — | 0.03 | 0.07 | 0.06 | 0.04 | 0.02 | 0.03 | 0.00 | 0.19 |
| E7 TaqI | 0.16 | 0.31 | 0.02 | 1.00 | — | 0.11 | 0.09 | 0.03 | 0.03 | 0.04 | 0.01 | 0.11 |
| pH131 HindI | 0.45 | 0.28 | 0.23 | 0.36 | 0.40 | — | 0.91 | 0.12 | 0.04 | 0.00 | 0.05 | 0.06 |
| W3D1.4 HindIII | 0.45 | 0.28 | 0.23 | 0.05 | 0.47 | 0.95 | — | 0.21 | 0.02 | 0.03 | 0.01 | 0.06 |
| H2.3A TaqI | 0.20 | 0.11 | 0.15 | 0.08 | 0.11 | 0.36 | 0.47 | — | 0.05 | 0.11 | 0.07 | 0.42 |
| EG1.4 HincII | 0.11 | 0.08 | 0.07 | 0.08 | 0.07 | 0.20 | 0.20 | 0.24 | — | 0.95 | 0.87 | 0.76 |
| EG1.4 BgII | 0.03 | 0.08 | 0.07 | 0.08 | 0.07 | 0.27 | 0.27 | 0.40 | 1.00 | — | 0.92 | 0.77 |
| JG2E1 PstI | 0.07 | 0.08 | 0.03 | 0.09 | 0.08 | 0.30 | 0.30 | 0.45 | 0.93 | 0.94 | — | 0.84 |
| E2.6/E.9 MspI | 0.22 | 0.08 | 0.07 | 0.02 | 0.03 | 0.20 | 0.20 | 0.34 | 0.81 | 0.82 | 0.92 | — |
| H2.8 NcoI | 0.05 | 0.07 | 0.01 | 0.08 | 0.06 | 0.31 | 0.31 | 0.45 | 0.92 | 0.83 | 1.00 | 0.92 |
| E4.1 MspI | 0.12 | 0.06 | 0.07 | 0.05 | 0.03 | 0.25 | 0.25 | 0.46 | 0.82 | 0.86 | 0.94 | 1.00 |
| J44 XbaI | 0.18 | 0.05 | 0.06 | 0.01 | 0.01 | 0.26 | 0.26 | 0.43 | 0.71 | 0.89 | 0.80 | 0.90 |
| 10-1X.6 AccI | 0.18 | 0.10 | 0.24 | 0.10 | 0.11 | 0.42 | 0.42 | 0.54 | 0.54 | 0.58 | 0.64 | 0.70 |
| 10-1X.6 HaeIII | 0.18 | 0.10 | 0.25 | 0.08 | 0.11 | 0.41 | 0.41 | 0.65 | 0.54 | 0.58 | 0.64 | 0.70 |
| T6/20 MspI | 0.27 | 0.07 | 0.36 | 0.13 | 0.13 | 0.23 | 0.23 | 0.29 | 0.05 | 0.00 | 0.01 | 0.07 |
| H1.3 NcoI | 0.08 | 0.06 | 0.06 | 0.03 | 0.01 | 0.30 | 0.30 | 0.55 | 0.71 | 0.78 | 0.87 | 0.90 |
| CE1.0 NdeI | 0.00 | 0.04 | 0.02 | 0.11 | 0.11 | 0.25 | 0.25 | 0.08 | 0.68 | 0.58 | 0.55 | 0.43 |
| J32 SacI | 0.03 | 0.13 | 0.07 | 0.17 | 0.13 | 0.17 | 0.24 | 0.07 | 0.21 | 0.21 | 0.24 | 0.22 |
| J3.11 MspI | 0.14 | 0.11 | 0.15 | 0.07 | 0.06 | 0.05 | 0.05 | 0.12 | 0.11 | 0.10 | 0.13 | 0.18 |
| J29 PvuII | 0.11 | 0.12 | 0.09 | 0.10 | 0.10 | 0.00 | 0.00 | 0.09 | 0.10 | 0.10 | 0.14 | 0.17 |

| | N chromosomes | | | | | | | | | |
|---|---|---|---|---|---|---|---|---|---|---|
| | H2.8 | E4.1 | J44 | 10-1X.6 | | T6/20 | H1.3 | CE1.0 | J32 | J3.11 | J29 |
| CF chromosomes | NcoI | MspI | XbaI | AccI | HaeIII | MspI | NcoI | NdeI | SacI | MspI | PvuII |
| metD BanI | 0.07 | 0.09 | 0.03 | 0.06 | 0.10 | 0.03 | 0.16 | 0.05 | 0.07 | 0.11 | 0.02 |
| metD TaqI | 0.24 | 0.03 | 0.11 | 0.06 | 0.02 | 0.06 | 0.13 | 0.15 | 0.09 | 0.09 | 0.05 |
| metH TaqI | 0.15 | 0.07 | 0.04 | 0.02 | 0.02 | 0.07 | 0.02 | 0.03 | 0.21 | 0.04 | 0.18 |
| E6 TaqI | 0.02 | 0.09 | 0.19 | 0.09 | 0.11 | 0.09 | 0.15 | 0.07 | 0.11 | 0.20 | 0.00 |
| E7 TaqI | 0.00 | 0.07 | 0.22 | 0.01 | 0.02 | 0.09 | 0.13 | 0.06 | 0.06 | 0.16 | 0.04 |
| pH131 HindI | 0.03 | 0.03 | 0.06 | 0.16 | 0.15 | 0.20 | 0.04 | 0.03 | 0.06 | 0.08 | 0.06 |
| W3D1.4 HindIII | 0.03 | 0.03 | 0.10 | 0.12 | 0.10 | 0.23 | 0.10 | 0.05 | 0.05 | 0.10 | 0.06 |
| H2.3A TaqI | 0.14 | 0.29 | 0.07 | 0.27 | 0.22 | 0.20 | 0.09 | 0.23 | 0.04 | 0.08 | 0.12 |
| EG1.4 HincII | 0.86 | 0.81 | 0.60 | 0.07 | 0.13 | 0.61 | 0.56 | 0.04 | 0.24 | 0.14 | 0.15 |
| EG1.4 BgII | 0.93 | 0.71 | 0.55 | 0.08 | 0.07 | 0.58 | 0.55 | 0.12 | 0.28 | 0.24 | 0.20 |
| JG2E1 PstI | 1.00 | 0.76 | 0.64 | 0.11 | 0.11 | 0.61 | 0.57 | 0.13 | 0.31 | 0.26 | 0.22 |
| E2.6/E.9 MspI | 0.83 | 0.97 | 0.76 | 0.56 | 0.52 | 0.47 | 0.70 | 0.32 | 0.31 | 0.25 | 0.22 |
| H2.8 NcoI | — | 0.74 | 0.65 | 0.13 | 0.18 | 0.60 | 0.59 | 0.10 | 0.28 | 0.28 | 0.18 |
| E4.1 MspI | 0.93 | — | 0.71 | 0.49 | 0.49 | 0.49 | 0.68 | 0.35 | 0.27 | 0.25 | 0.21 |
| J44 XbaI | 0.60 | 0.85 | — | 0.33 | 0.40 | 0.65 | 0.64 | 0.32 | 0.24 | 0.22 | 0.23 |
| 10-1X.6 AccI | 0.69 | 0.69 | 0.59 | — | 0.91 | 0.19 | 0.36 | 0.56 | 0.00 | 0.02 | 0.03 |
| 10-1X.6 HaeIII | 0.69 | 0.69 | 0.59 | 1.00 | — | 0.18 | 0.43 | 0.62 | 0.02 | 0.02 | 0.08 |
| T6/20 MspI | 0.02 | 0.01 | 0.11 | 0.69 | 0.69 | — | 0.56 | 0.03 | 0.21 | 0.16 | 0.25 |
| H1.3 NcoI | 0.87 | 0.93 | 0.92 | 0.64 | 0.64 | 0.12 | — | 0.40 | 0.19 | 0.13 | 0.20 |
| CE1.0 NdeI | 0.55 | 0.37 | 0.44 | 0.24 | 0.24 | 0.07 | 0.40 | — | 0.19 | 0.20 | 0.14 |
| J32 SacI | 0.24 | 0.21 | 0.21 | 0.27 | 0.26 | 0.13 | 0.21 | 0.18 | — | 0.84 | 0.97 |
| J3.11 MspI | 0.19 | 0.15 | 0.20 | 0.28 | 0.29 | 0.24 | 0.14 | 0.07 | 0.81 | — | 0.71 |
| J29 PvuII | 0.20 | 0.16 | 0.16 | 0.29 | 0.29 | 0.23 | 0.16 | 0.06 | 0.65 | 0.97 | — |

Strong allelic association was also detected among subgroups of RFLPs on both the CF and N chromosomes. As shown in Table 4, the DNA markers that are physically close to each other generally appeared to have strong association with each other. For example, strong (in some cases almost complete) allelic association was detected between adjacent markers E6 and E7, between pH131 and W3D1.4 between the AccI and HaeIII polymorphic sites detected by 10-1X.6 and amongst EG1.4, JG2E1, E2.6(E.9), E2.8 and E4.1. The two groups of distal markers in the MET and D7S8 region also showed some degree of linkage disequilibrium among themselves but they showed little association with markers from E6 to CE1.0, consistent with the distant locations for MET and D7S8. On the other hand, the lack of association between DNA markers that are physically close may indicate the presence of recombination hot spots. Examples of these potential hot spots are the region between E7 and pH131, around H2.3A, between J44 and the regions covered by the probes 10-1X.6 and T6/20 (see FIG. 14). These regions, containing frequent recombination breakpoints, ware useful in the subsequent analysis of extended haplotype data for the CF region.

3.5 Haplotype Analysis

Extended haplotypes based on 23 DNA markers were generated for the CF and N chromosomes in the collection of families previously used for linkage analysis. Assuming recombination between chromosomes of different haplotype, it was possible to construct several lineages of the observed CF chromosomes and, also, to predict the location of the disease locus.

To obtain further information useful for understanding the nature of different CF mutations, the F508 deletion data were correlated with the extended DNA marker haplotypes. As shown in Table 5, five major groups of N and CF haplotypes could be defined by the RFLPs within or immediately adjacent to th putative CF gene regions (6-8).

TABLE 5

DNA marker haplotypes spanning the CF locus.

| | | HAPLOTYPES[a] | | | | | | | | | CF[b] | | | |
|---|---|---|---|---|---|---|---|---|---|---|---|---|---|---|
| | | | | | | | | | | | PI | PS | PI | PS | |
| | | 1 | 2 | 3 | 4 | 5 | 6 | 7 | 8 | 9 | (F508YF508) | others | others | N |
| I. (a) | | A | A | A | A | A | A | A | A | A | 10 | 1 | * | * | * |
| | | A | A | A | A | A | A | * | A | A | 3 | * | * | * | * |
| | | A | A | A | A | * | A | * | * | A | 1 | * | * | * | * |
| | | A | A | A | A | * | * | A | * | A | * | * | * | * | 1 |
| | | A | A | A | A | A | A | A | A | B | 10 | * | * | * | 1 |
| | | A | A | * | A | A | A | A | A | B | 4 | * | * | * | * |
| | | A | A | A | A | * | A | A | A | B | 1 | * | * | * | * |
| | | A | A | * | A | A | A | A | A | C | 1 | * | * | * | * |
| | | B | A | A | A | A | A | A | A | A | 4 | * | * | * | * |
| | | B | A | * | A | A | A | A | A | A | 1 | * | * | * | * |
| | | B | A | A | A | * | A | A | A | A | * | 1 | * | * | * |
| | | B | A | A | A | A | A | A | A | * | 1 | * | * | * | — |
| | | B | A | A | * | * | A | * | A | A | 1 | * | * | * | — |
| | | A | B | A | A | A | A | A | A | A | 1 | * | * | * | — |
| | | A | D | A | A | A | A | A | A | A | 1 | * | * | * | — |
| | | A | C | A | A | A | A | A | A | A | 1 | * | * | * | — |
| | | B | B | A | A | A | A | A | A | A | 1 | * | * | * | — |
| | | B | C | A | A | A | A | A | A | A | 2 | * | * | * | — |
| | | E | B | A | A | * | * | A | * | A | 1 | * | * | * | — |
| | | D | B | A | A | * | A | * | A | A | 1 | * | * | * | — |
| | | D | B | B | A | A | A | A | A | A | 1 | * | * | * | — |
| | | B | A | * | A | A | A | A | A | B | 1 | * | * | * | * |
| | | C | A | * | A | A | A | A | A | B | 1 | * | * | * | * |
| | | A | D | A | A | A | A | A | A | B | 1 | * | * | * | * |
| | | D | C | A | A | A | A | A | A | B | * | 1 | * | * | * |
| | | A | D | A | A | * | A | A | A | B | 1 | * | * | * | * |
| | | D | D | * | A | A | A | A | A | B | * | * | * | * | 1 |
| | | E | B | * | A | A | A | * | A | B | 1 | * | * | * | * |
| | | A | B | A | A | A | A | A | A | E | 2 | * | * | * | * |
| | | A | B | * | A | A | A | A | A | E | 1 | 1 | * | * | * |
| | | A | E | B | A | A | A | A | A | E | 1 | * | * | * | * |
| | | A | C | A | A | A | A | A | A | B | 1 | * | * | * | * |
| | | A | C | * | C | * | A | A | A | B | * | 1 | * | * | * |
| | | A | B | A | B | A | A | A | * | A | * | * | * | * | 1 |
| | | B | C | B | A | * | A | A | A/D | B | 1 | * | * | * | * |
| (b) | | A | C | * | A | A | A | A | A | A | * | * | * | 1 | * |
| | | A | C | A | A | A | A | A | A | * | * | * | 1 | * | * |
| | | D | C | * | A | A | A | A | A | B | * | * | 1 | * | * |
| | | D | C | A | A | A | A | A | A | D | * | * | * | * | 1 |
| | | F | C | * | A | A | A | A | A | B | * | * | 1 | * | * |
| | | B | C | A | A | A | A | A | A | B | * | * | 3 | * | * |
| (c) | | B | C | A | B | C | A | A | D | A | * | * | * | * | 1 |
| | | B | C | A | B | C | A | A | D | B | * | * | 1 | * | * |
| | | F | C | A | B | C | A | A | D | B | * | * | * | * | 1 |
| | | F | A | A | B | C | A | A | D | B | * | * | * | * | 1 |
| | | A | B | A | B | C | A | A | D | B | * | * | * | * | 1 |
| | | B | B | A | B | C | A | A | D | B | * | * | * | * | 1 |

TABLE 5-continued

DNA marker haplotypes spanning the CF locus.

|     |     |   |   |   |   |   |   |   |   |   |   |   |   |    |
|-----|-----|---|---|---|---|---|---|---|---|---|---|---|---|----|
|     |     | B | D | A | B | C | A | * | D | C | * | * | * | * | 1 |
|     |     | A | B | A | B | A | A | * | D | A | * | * | * | * | 1 |
|     | (d) | D | B | A | A | A | A | * | C | A | * | * | * | * | 1 |
|     |     | E | C | B | C | A | A | A | C | B | * | * | * | * | 1 |
|     |     |   |   |   |   |   |   |   |   |   | 57 | 5 | 7 | 1 | 14 |
| II. | (a) | B | A | * | B | B | B | A | C | B | * | * | 1 | * | * |
|     |     | * | B/C | B | B | B | B | A | C | B | * | * | 1 | * | * |
|     |     | B | A | * | B | * | B | A | A/C | B | * | * | * | 1 | * |
|     |     | A | B | B | B | B | B | A | C | B | * | * | 1 | * | * |
|     |     | B | B | B | B | B | B | A | C | A | * | * | * | * | 3 |
|     |     | A | C | B | B | B | B | A | C | A | * | * | * | * | 1 |
|     |     | A | C | B | B | B | B | * | C | A | * | * | * | * | 1 |
|     |     | F | C | B | B | B | B | A | C | A | * | * | * | * | 1 |
|     |     | A | C | B | B | B | B | A | C | B | * | * | * | * | 1 |
|     |     | A | C | * | E | B | B | * | C | C | * | * | * | * | 1 |
|     |     | B | C | B | B | * | B | A | C | C | * | * | * | 1 | * |
|     |     | B | C | B | B | B | B | A | C | B | * | * | * | * | 1 |
|     |     | B | C | B | B | B | B | A | C | A | * | * | * | * | 1 |
|     |     | B | C | B | B | B | B | A | C | D | * | * | * | * | 1 |
|     |     | B | C | * | B | B | B | A | C | B | * | * | * | * | 1 |
|     |     | B | C | B | B | B | * | * | C | B | * | * | * | * | 1 |
|     |     | D | C | B | B | B | B | A | C | B | * | * | * | * | 2 |
|     |     | D | * | B | B | * | B | A | C | B | * | * | * | * | 1 |
|     |     | F | C | B | B | B | B | A | C | B | * | * | * | * | 1 |
|     |     | C | C | * | B | B | B | A | C | B | * | * | * | * | 1 |
|     |     | A | A | A | B | B | B | A | C | B | * | * | * | * | 1 |
|     |     | E | G | A | B | B | B | A | C | B | * | * | * | * | 1 |
|     |     | F | A | * | B | B | B | A | C | B | * | * | * | * | 1 |
|     |     | B | H | * | B | B | B | A | C | B | * | * | * | * | 1 |
|     |     | B | B | * | B | B | B | A | C | B | * | * | * | * | 1 |
|     |     | A | B | A | B | B | B | A | C | B | * | * | * | * | 1 |
|     |     | F | D | A | B | B | B | A | C | B | * | * | * | * | 1 |
|     |     | C | D | A | B | B | B | A | C | A | * | * | * | * | 1 |
|     |     | B | D | A | B | B | B | A | C | A | * | * | * | * | 1 |
|     |     | E | C | A | B | B | B | A | C | A | * | * | * | * | 2 |
|     |     | A | C | A | B | B | B | A | C | B | * | * | * | * | 1 |
|     |     | A | C | A | B | B | B | * | C | B | * | * | * | * | 1 |
|     |     | A | C | A | B | B | B | A | C | C | * | * | * | * | 1 |
|     |     | B | C | A | B | B | B | A | C | B | * | * | * | * | 1 |
|     |     | D | B/C | * | B | B | B | A | C | A | * | * | * | * | 2 |
|     |     | C | C | A | B | B | B | A | C | A | * | * | * | 1 | * |
|     |     | D | B | * | B | B | B | A | A/C | B | * | * | * | * | 1 |
|     |     | D | B | A | B | * | B | A | C | B | * | * | * | * | 1 |
|     |     | A | G | A | B | B | B | A | C | A | * | * | * | * | 1 |
|     |     | B | C | * | B | B | B | A | A/C | A | * | * | * | * | 1 |
|     |     | A | C | B | D | B | B | A | C | B | * | * | 1 | * | * |
|     |     | A | C | * | D | * | B | A | C | B | * | * | * | * | 1 |
|     |     | B | B | B | B | B | B | A | C | C | * | * | * | * | 1 |
|     |     | F | D | A | B | B | B | A | C | C | * | * | * | 1 | * |
|     |     | A | A | A | A | A | B | A | C | D | * | * | * | * | 1 |
|     |     | * | B/C | A | B | C | B | A | C | E | * | * | * | * | 1 |
|     |     | A | B | A | B | B | B/C | A | C | A | * | * | * | * | 1 |
|     | (b) | A | C | A | B | B | B | A | B | E | * | * | 1 | * | * |
|     |     | A | C | * | B | B | B | A | B | B | * | * | 1 | * | * |
|     | (c) | B | D | * | B | * | B | A | A | A | * | * | * | * | 1 |
|     |     |   |   |   |   |   |   |   |   |   | 0 | 0 | 6 | 4 | 45 |
| III. | (a) | B | C | B | A | A | C | B | A | B | 1 | * | * | * | * |
|     | (b) | B | A | B | A | A | C | B | A | B | * | * | 1 | * | * |
|     |     | B | C | B | A | A | C | B | A | A | * | * | 1 | * | * |
|     |     | B | C | B | A | A | C | B | A | B | * | * | * | * | 1 |
|     |     | B | C | * | A | A | C | B | A | B | * | * | * | * | 2 |
|     |     | A | B | * | A | A | C | B | A | B | * | * | * | * | 1 |
|     |     | A | B | * | A | A | C | B | A | C | * | * | * | * | 1 |
|     |     | B | B | B | A | A | C | B | A | B | * | * | * | * | 2 |
|     |     | D | C | B | A | A | C | B | A | A | * | * | * | 1 | * |
|     |     | A | B | B | C | A | C | B | A | B | * | * | * | * | 1 |
|     |     | B | B | A | A | A | C | B | A | B | * | * | 2 | * | 1 |
|     |     | B | B | * | A | A | C | B | A | B | * | * | 1 | * | 1 |
|     |     | B | B | A | A | A | C | B | A | A | * | * | * | 1 | * |
|     |     | D | A | A | A | A | C | B | A | B | * | * | * | * | 1 |
|     |     | D | C | A | A | A | C | B | A | B | * | * | * | * | 2 |
|     |     | A | C | * | A | A | C | B | A | B | * | * | 1 | * | 1 |
|     |     | D | B | A | A | A | C | * | A | C | * | * | * | * | 1 |
|     | (c) | A | A | A | B | B | C | B | A | * | * | * | 1 | * | * |
|     |     | F | B | B | B | B | C | B | A | E | * | * | * | * | 1 |

TABLE 5-continued

DNA marker haplotypes spanning the CF locus.

|       |     | D | B | B | B | B | C | B | A | A | * | * | * | * | 1 |
|-------|-----|---|---|---|---|---|---|---|---|---|---|---|---|---|---|
|       |     |   |   |   |   |   |   |   |   |   | 1 | 0 | 7 | 2 | 17 |
| IV.   |     | F | C | B | A | A | C | B | C | A | * | * | * | 1 | * |
|       |     | B | C | A | A | A | C | B | C | * | * | * | * | * | 1 |
|       |     | A | B | A | A | A | C | * | C | B | * | * | * | * | 1 |
|       |     | A | H | B | A | * | C | * | C | B | * | * | * | * | 1 |
|       |     | D | B | B | B | B | C | B | C | B | * | * | * | * | 1 |
|       |     |   |   |   |   |   |   |   |   |   | 0 | 0 | 0 | 1 | 4 |
| V.    | (a) | B | C | B | B | B | C | A | C | A | * | * | 1 | * | * |
|       |     | A | C | B | B | * | * | A | * | A | * | * | 1 | * | * |
|       |     | B | B | B | B | B | C | A | C | B | * | * | * | * | 1 |
|       |     | B | C | B | B | B | C | A | C | B | * | * | * | * | 1 |
|       |     | B | C | * | B | B | C | A | C | B | * | * | * | * | 1 |
|       |     | D | * | A | B | B | C | * | C | B | * | * | * | * | 1 |
|       | (b) | B | C | A | B | C | C | A | C | A | * | * | * | 1 | * |
|       |     | B | C | * | B | C | C | * | C | D | * | * | * | * | 1 |
|       |     |   |   |   |   |   |   |   |   |   | 0 | 0 | 2 | 1 | 5 |
| Other: |    | B | C | B | A | A | B | B | A | B | * | * | * | * | 1 |
|       |     | B | C | B | A | A | D | B | A | B | * | * | * | * | 1 |
|       |     | B | C | B | E | B | A | B | D | A | * | * | * | * | 1 |
|       |     | B | C | A | B | B | E | * | C | * | * | * | * | * | 1 |
|       |     | B | D | B | B | B | F | A | C | B | * | * | * | * | 1 |
|       |     | A | C | * | A | A | C | E | D | A | * | * | * | * | 1 |
|       |     | G | B | B | A | A | B/C | A | A/D | B | * | * | * | * | 1 |
|       |     |   |   |   |   |   |   |   |   |   | 0 | 0 | 0 | 0 | 7 |
| Unclassified: | | * | * | * | * | * | * | * | * | * | 4 | 10 | 2 | 18 | 6 |
| Total: |    |   |   |   |   |   |   |   |   |   | 62 | 15 | 24 | 27 | 98 |

[a]The extended haplotype data are derived from the CF families used in previous linkage studies (see footnote (a) of Table 3) with additional CF-PS families collected subsequently (Kerem et al, Am. J. Genet. 44:827 (1989)). The data are shown in groups (regions) to reduce space. The regions are assigned primarily according to pairwise assocation data shown in Table 4 with regions 6–8 spanning the putative CF locus (the F508 deletion is between regions 6 and 7). A dash (—) is shown at the region where the haplotype has not been determined due to incomplete data or inability to establish phase. Alternative haplotype assignments are also given where data are incomplete. Unclassified includes those chromosomes with more than 3 unknown assignments. The haplotype definitions for each of the 9 regions are:

Region 1 =

|       | metD<br>BanI | metD<br>TaqI | metH<br>TaqI |
|-------|------|------|------|
| A =   | 1    | 1    | 1    |
| B =   | 2    | 1    | 2    |
| C =   | 1    | 1    | 2    |
| D =   | 2    | 2    | 1    |
| E =   | 1    | 2    | *    |
| F =   | 2    | 1    | 1    |
| G =   | 2    | 2    | 2    |

Region 2 =

|       | E6<br>TaqI | E7<br>TaqI | pH131<br>HinfI | W3D1.4<br>HindIII |
|-------|------|------|------|------|
| A =   | 1    | 2    | 2    | 2    |
| B =   | 2    | 1    | 1    | 1    |
| C =   | 1    | 2    | 1    | 1    |
| D =   | 2    | 1    | 2    | 2    |
| E =   | 2    | 2    | 2    | 1    |
| F =   | 2    | 2    | 1    | 1    |
| G =   | 1    | 2    | 1    | 2    |
| H =   | 1    | 1    | 2    | 2    |

Region 3 =

|       | H2.3A<br>TaqI |
|-------|------|
| A =   | 1    |
| B =   | 2    |

TABLE 5-continued

DNA marker haplotypes spanning the CF locus.

Region 4 =

| | EG1.4<br>HincII | EG1.4<br>BgII | JG2E1<br>PstI |
|---|---|---|---|
| A = | 1 | 1 | 2 |
| B | | | |
| C = | 2 | 2 | 2 |
| D = | 1 | 1 | 1 |
| E = | 1 | 2 | 1 |

Region 5 =

| | E2.6<br>MspI | E2.8<br>NcoI | E4.1<br>MspI |
|---|---|---|---|
| A = | 2 | 1 | 2 |
| B = | 1 | 2 | 1 |
| C = | 2 | 2 | 2 |

Region 6 =

| | J44<br>XbaI | 10-1X.6<br>AccI | 10-1X.6<br>HaeIII |
|---|---|---|---|
| A = | 1 | 2 | 1 |
| B = | 2 | 1 | 2 |
| C = | 1 | 1 | 2 |
| D = | 1 | 2 | 2 |
| E = | 2 | 2 | 2 |
| F = | 2 | 2 | 1 |

Region 7 =

| | T6/20<br>MspI |
|---|---|
| A = | 1 |
| B = | 2 |

Region 8 =

| | H1.3<br>NcoI | CE1.0<br>NdaI |
|---|---|---|
| A = | 2 | 1 |
| B = | 1 | 2 |
| C = | 1 | 1 |
| D = | 2 | 2 |

Region 9 =

| | J32<br>SacI | J3.11<br>MspI | J29<br>PvuII |
|---|---|---|---|
| A = | 1 | 1 | 1 |
| B = | 2 | 2 | 2 |
| C = | 2 | 1 | 2 |
| D = | 2 | 2 | 1 |
| E = | 2 | 1 | 1 |

[b]Number of chromosomes scored in each class:
CF-PI(F) = CF chromosomes from CF-PI patients with the F508 deletions;
CF-PS(F) = CF chromosomes from CF-PS patients with the F508 deletions;
CF-PI = Other CF chromosomes from CF-PI patients;
CF-PS = Other CF chromosomes from CF-PS patients;
N = Normal chromosomes derived from earlier patients.

It was apparent that most recombinations between haplotypes occurred between regions 1 and 2 and between regions 8 and 9, again in good agreement with the relatively long physical distance between these regions. Other, less frequent, breakpoints were noted between short distance intervals and they generally corresponded to the hot spots identified by pairwise allelic association studies as shown above. The striking result was that the F508 deletion associated almost exclusively with Group I, the most frequent CF haplotype, supporting the position that this deletion constitutes the major mutation in CF. More important, while the F508 deletion was detected in 89% (62/70) of the CF chromosomes with the AA haplotype (corresponding to the two regions, 6 and 7) flanking the deletion, none was found in the 14 N chromosomes within the same group ($x^2$=47.3, $p<10^{-4}$). The F508 deletion was therefore not a common sequence polymorphism associated with the core of the Group I haplotype (see Table 5).

One of the CF chromosomes, detected by the specific oligonucleotide probe for the F508 deletion, was found to belong to a different haplotype group (Group III). None of the 9 other CF chromosomes nor 17 N chromosomes with the sane group hybridized to the probe. This specific hybridization result suggests that the mutation harbored on this chromosome is similar to F508. Although recombination or gene conversion are possible mechanisms to explain the presence of this deletion on a non-Group I haplotype, it is more likely that these 2 Group III chromosomes represent a recurrent mutation event, a situation similar to the $\beta^S$ and $\beta^E$ mutations at the $\beta$ globin locus.

Together, the results of the oligonucleotide hybridization study and the haplotype analysis support the tact that th gene locus described here in the CF gene and that the 3 bp (F508) deletion is the most common mutation in CP.

3.6 Other CF Mutations

The association of the F508 deletion with 1 common and 1 rare CF haplotype provided further insight into the number of mutational events that could contribute to the present patient population. Based on the extensive haplotype data, the 2 original chromosomes in which the F508 deletion occurred are likely to carry the haplotype -AAAAAAA- (Group Ia) and -CBAACBA- (Group IIIa), as defined in Table 5. The other Group I CF chromosomes carrying the deletion are probably recombination products derived from the original chromosome. If the CF chromosomes in each haplotype group are considered to be derived from the same origin, only 3-4 additional mutational events would be predicted (see Table 5). However, since many of the CF chromosomes in the same group are markedly different from each other, further subdivision within each group is possible. As a result, a higher number of independent mutational events could be considered and the data suggest that at least 7 additional, putative mutations also contribute to the CF-PI phenotype (see Table 4). The mutations leading to the CF—PS subgroup are probably more heterogeneous.

The 7 additional CF-PI mutations are represented by the haplotypes: -CAAAAAA- (Group Ib), -CABCAAD- (Group Ic), ---BBBAC- (Group IIa), -CABBBAB- (Group Va). Although the molecular defect in each of these mutations has yet to be defined, it is clear that none of these mutations severely affect the region corresponding to the oligonucleotide binding sites used in the PCR/hybridization experiment.

3.7 Pancreatic Sufficiency

CF-PS is defined clinically as sufficient pancreatic exocrine function for digestion of food; however, the level of residual pancreatic enzyme activity in the digestive system varies from patient to patient. Previous haplotype data suggested that the CF-PI and CF-PS patients are due to different mutant alleles. Although the basic biochemical defect in CF has yet to be defined, it is possible that the residual pancreatic enzyme activity in CF-PS patients is a direct reflection of the activity of the mutant CF gene product. Thus, the residual exocrine function conferred by a mild (CF—PS) allele, although much lower than that of the normal gene product, would constitute a dominant phenotype over that of more severe (CF-PI) mutations with little or no function. It follows that only patients carrying 2 copies of severe alleles would be CF-PT and that patients carrying 1 or 2 mild alleles would be CF—PS.

To test the above hypothesis, the information on the proportion of CF patients carrying the F508 deletion could be utilized. Assuming that a severe mutation is recessive to a mild mutation and a distribution of CF alleles among the patient population according to the Hardy-Weinberg law, the frequency of severe alleles could be estimated to be 0.92 and that for the mild alleles (M), 0.08 (see Table 6).

TABLE 6

POPULATION ANSLYSIS OF CF-PI AND CF-PS

| | Assumed Genotype[a] | Predicted Frequency[b] | Observed[c] | Expected[d] |
|---|---|---|---|---|
| Pancreatic insufficient (PI) | FF | 0.459 | 21 | 21.1 |
| | FS | 0.331 | 14 | 15.2 |
| | SS | 0.060 | 4 | 2.7 |
| | Total | 0.850 | 39 | — |
| Pancreatic sufficient (PS) | FM | 0.106 | 15[e] | 14.8 |
| | SM | 0.038 | 6 | 6.2 |
| | MM | 0.006 | | |
| | Total | 0.150 | 21 | |

(a) Allele designations: F=the 3 bp deletion (deletion or phenylalanine at amino acid position 508); S=uncharacterized severe mutant alleles; M=uncharacterized mild mutant alleles.

(b) Assuming that tht CF-PI mutant phenotype is recessive to the CF—PS mutant phenotype, the frequency of CF-PI mutant alleles, including the 3 bp deletion, could be estimated from the observed proportion of the CF-PI patients in the CF clinic (Corey et al *J. Pediatr.* 115:274 (1989)), i.e., (0.85)=0.92. The observed allele frequency for F in the total CF population is 0.68 (Table 3); the frequency for S=0.92-0.68=0.24; the frequency for M=1-0.92-0.08. The frequency for each genotype was then calculated by using the Hardy-Weinberg Law.

Figure 15:
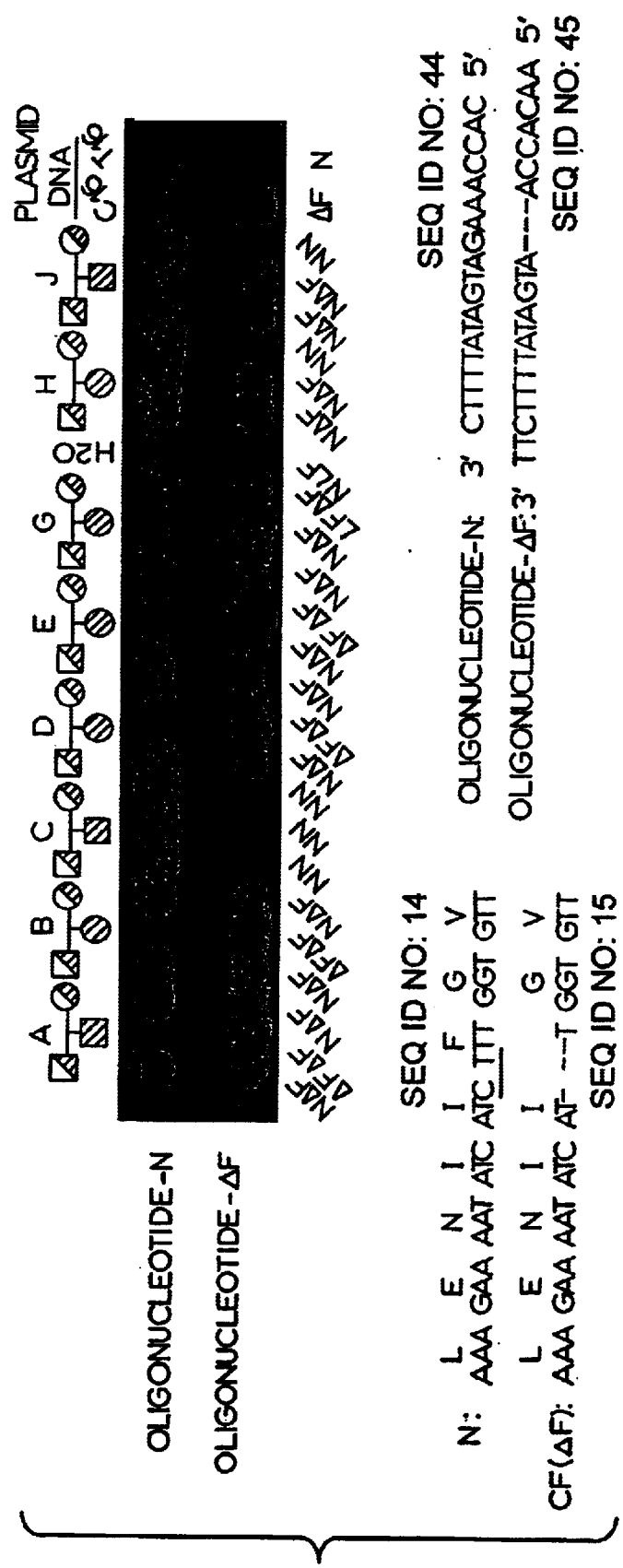
FIG. 15 represents the detection of the F508 mutation by oligonucleotide hybridization with Probe N detecting the normal sequence and Probe F detecting the CF mutant sequence.

(c) The number of CF-PI and CF-PS patients in each category was obtained by oligonucleotide hybridization analysis as illustrated in FIG. 15. The patients were from the CF families used in our linkage analysis with 14 additional CF—PS patients/families from a subsequent study. Since SM and MM could not be distinguished genotypically or phenotypically, they were combined in the analysis.

(d) The expected numbers were calculated for CF-PI and CF-PS after normalization within each group. The $x^2$ of fit is 0.86, d.f. =3, 0.74<p <0.90

(e) This number is higher than would be expected (15 observed vs. 9.6 expected) if the F508 deletion is in Hardy-Weinberg equilibrium among all CF chromosomes ($x^2$=6.48, d.f.=1, p<0.011

Since the majority of CF-PI patients were found to be homozygous for the F508 mutation (F), it was reasonable to assume that this mutation corresponded to one of the severe alleles. Given the observed frequency of F (0.68) in the studied CF population, the frequency of the remaining severe alleles (S) could be derived. The proportion of FF, SS, MM, FS, FM and SM patients was then calculated. Since individuals with SM and MM could not be distinguished phenotypically or genotypically, they were combined in the analysis. As shown in Table 6, the observed frequencies for all 5 groups of patients were as expected from this hypothesis.

The above analysis thus provides strong support for our position that CF-PI is due to the presence of 2 severe alleles and that a CF-PS patient carries either a single severe allele or 2 mild alleles. This model also explains the lower frequency of the F508 deletion in the CF-PS than in the CF-PI population and the excess number of CF-PS patients with one copy of the deletion (see note in Table 6).

Given the predicted dominant phenotype conferred by the M alleles, it was necessary to examine the CF chromosomes in CF-PS patients individually in order to identify those carrying the M alleles. As shown in Table 7, five of the 7 representative CF—PS patients carry one copy of the F508 deletion; at least 5 different haplotypes could be assigned to the other CF chromosomes.

TABLE 7

Haplotypes of CF chromosomes in CF-PS individuals and families with MI

| Family # | 1 | 2 | 3 | 4 | 5 | 6 | 7 | 8 | 9 | CF Alleles |
|---|---|---|---|---|---|---|---|---|---|---|
| (a) CF-PS individuals | | | | | | | | | | |
| 3 | A | A | A | A | A | A | — | — | A | F (Group Ia) |
|  | D | C | B | A | A | C | B | A | A | M (predicted, Group IIIb) |
| 14 | B | A | A | A | — | A | A | A | A | F (Group Ia) |
|  | B | C | B | B | — | B | A | C | C | M (predicted, Group IIa) |
| 27 | A | B | — | A | A | A | A | A | E | F (Group Ia) |
|  | A | C | — | A | A | A | A | A | A | M (predicted, Group Ib) |
| 29 | A | C | — | C | — | A | A | A | B | F (Group Ia) |
|  | B | A | — | B | — | B | A | A/C | B | M (predicted, Group IIa) |
| 40 | D | A | A | A | A | A | A | A | B | F (Group Ia) |
|  | F | C | B | A | A | C | B | C | A | M (predicted, Group IV) |
| 51 | C | C | A | B | B | B/C | A | C | A | M (predicted, Group IIa) |
|  | F | D | A | B | B | B/C | A | C | C | M (predicted, Group IIa) |
| 54 | B | C | A | B | C | C | A | C | A | M or S (predicted, Group Vb) |
|  | B | B | A | A | A | C | B | A | A | M (predicted, Group IIIb) |
| (b) Families with MI | | | | | | | | | | |
| 4 | B | A | A | A | A | A | A | A | A | F (Group Ia) |
|  | B | A | A | A | A | A | A | A | A | F (Group Ia) |
| 10 | D | B | A | A | — | A | — | A | A | F (Group Ia) |
|  | A | D | A | A | — | A | A | A | B | F (Group Ia) |
| 23 | A | E | B | A | A | A | A | A | E | F (Group Ia) |
|  | B | C | A | A | A | A | A | A | B | S (predicted, Group Ib) |
| 28 | A | A | — | A | A | A | A | A | C | F (Group Ia) |
|  | A | A | — | A | A | A | A | A | B | F (Group Ia) |
| 33 | B | B | — | A | A | A | — | A | B | F (Group Ia) |
|  | B | A | — | A | A | A | A | A | B | F (Group Ia) |
| 49 | A | A | A | A | A | A | A | A | B | F (Group Ia) |
|  | A | A | A | A | A | A | A | A | B | F (Group Ia) |

(a) The haplotype definitions are the same as in Table 5.
(b) Allele designations are the same as in Table 6: F = the F508 deletion; S = uncharacterized severe mutant allele; M = uncharacterized mild mutant allele.

These latter observations provide further support that the majority of CF—PS patients are compound heterozygotes.

4.0 CFTR Protein

As discussed with respect to the DNA sequence of FIGS. 1A–1H, analysis of the sequence of the overlapping cDNA clones predicted an unprocessed polypeptide of 1480 amino acids with a molecular mass of 168,138 daltons. As later described, due to polymorphisms in the protein, the molecular weight of the protein can vary due to possible substitutions or deletion of certain amino acids. The molecular weight will also change due to the addition of carbohydrate units to form a glycoprotein. It is also understood that the functional protein in the cell will be similar to the unprocessed polypeptide, but may be modified due to cell metabolism.

Accordingly, the invention provides purified normal CFTR polypeptide characterized by a molecular weight of about 170,000 daltons and having epithelial cell transmembrane ion conductance activity. The normal CFTR polypeptide, which is substantially free of other human proteins, is encoded by the aforementioned DNA sequences and according to one embodiment, that of FIGS. 1A–1H. Such polypeptide displays the immunological or biological activity of normal CFTR polypeptide. As will be later discussed, the CFTR polypeptide and fragments thereof may be made by chemical or enzymatic peptide synthesis or expressed in an appropriate cultured cell system. The invention also provides purified mutant CFTR polypeptide which is characterized by cystic fibrosis-associated activity in human epithelial cells. Such mutant CFTR polypeptide, as substantially free of other human proteins, can be encoded by the mutant DNA sequence.

4.1 Structure of CFTR

The most characteristic feature of the predicted protein is the presence of two repeated motifs, each of which consists of a set of amino acid residues capable of spanning the membrane several times followed by sequence resembling consensus nucleotide (ATP)-binding folds (NBFs) (FIGS. 11, 12 and 16A–16B). These characteristics are remarkably similar to those of the mammalian multidrug resistant P-glycoprotein and a number of other membrane-associated proteins, thus implying that the predicted CF gene product is likely to be involved in the transport of substances (ions) across the membrane and is probably a member of a membrane protein super family.

Figure 13:
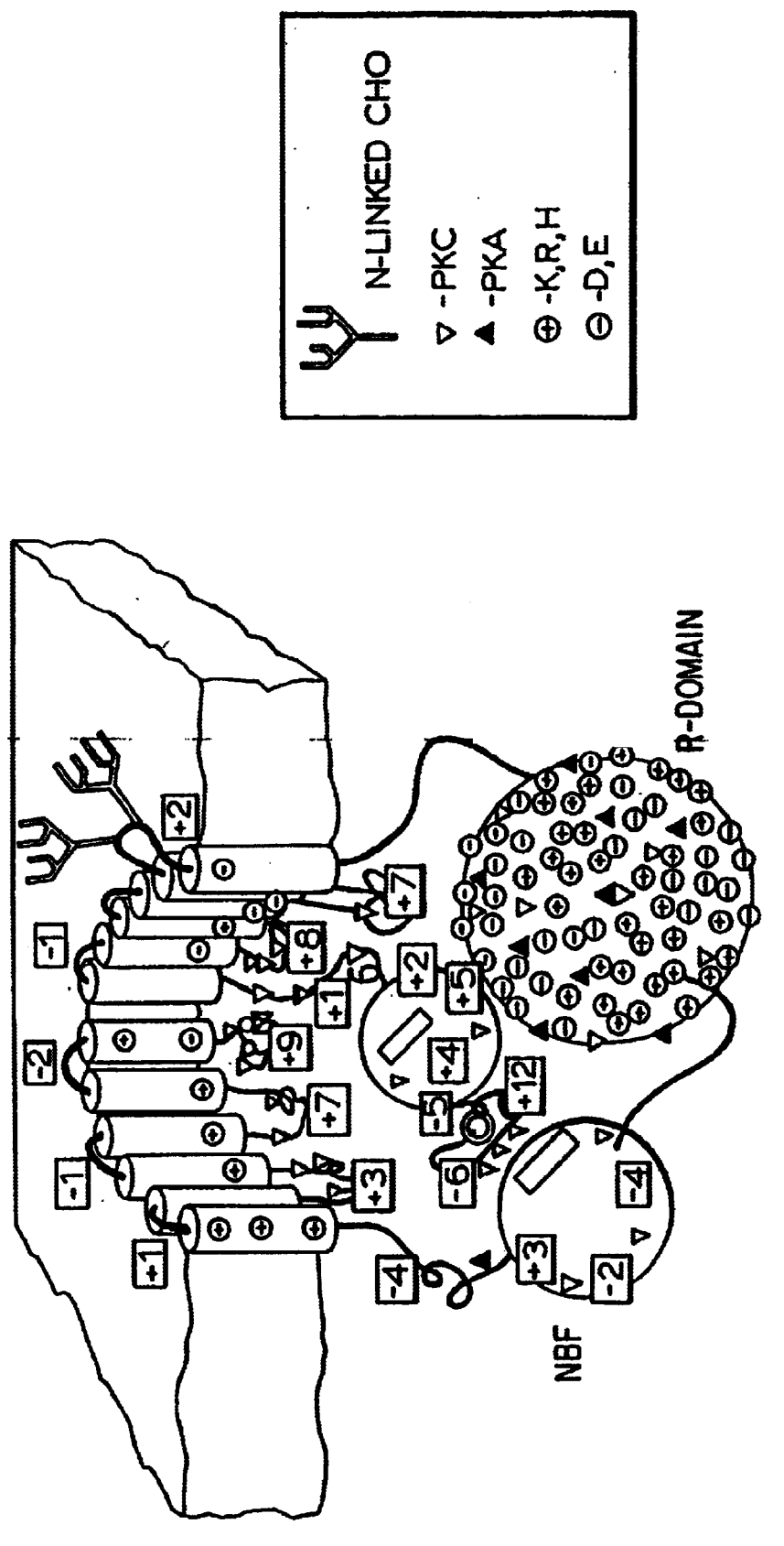
FIG. 13 is a schematic model of the predicted CFTR protein.

FIG. 13 is a schematic model of the predicted CFTR protein. In FIG. 13, cylinders indicate membrane spanning helices, hatched spheres indicate NBFS. The stippled sphere is the polar R-domain. The 6 membrane spanning helices in each half of the molecule are depicted as cylinders. The inner cytoplasmically oriented NBFs are shown as hatched spheres with slots to indicate the means of entry by the nucleotide. The large polar R-domain which links the two halves is represented by an stippled sphere charged individual amino acids within the transmembrane segments and on the R-domain surface are depicted as small circles containing the charge sign. Not charges on the internal and external loops joining the membrane cylinders and on regions of the NBFs are contained in open squares. Sites for phosphorylation by protein kinases A or C are shown by closed and open triangles respectively. K,R,H,D, and E are standard nomenclature for the amino acids, lysine, arginine, histidine, aspartic acid and glutamic acid respectively.

Figure 16A:
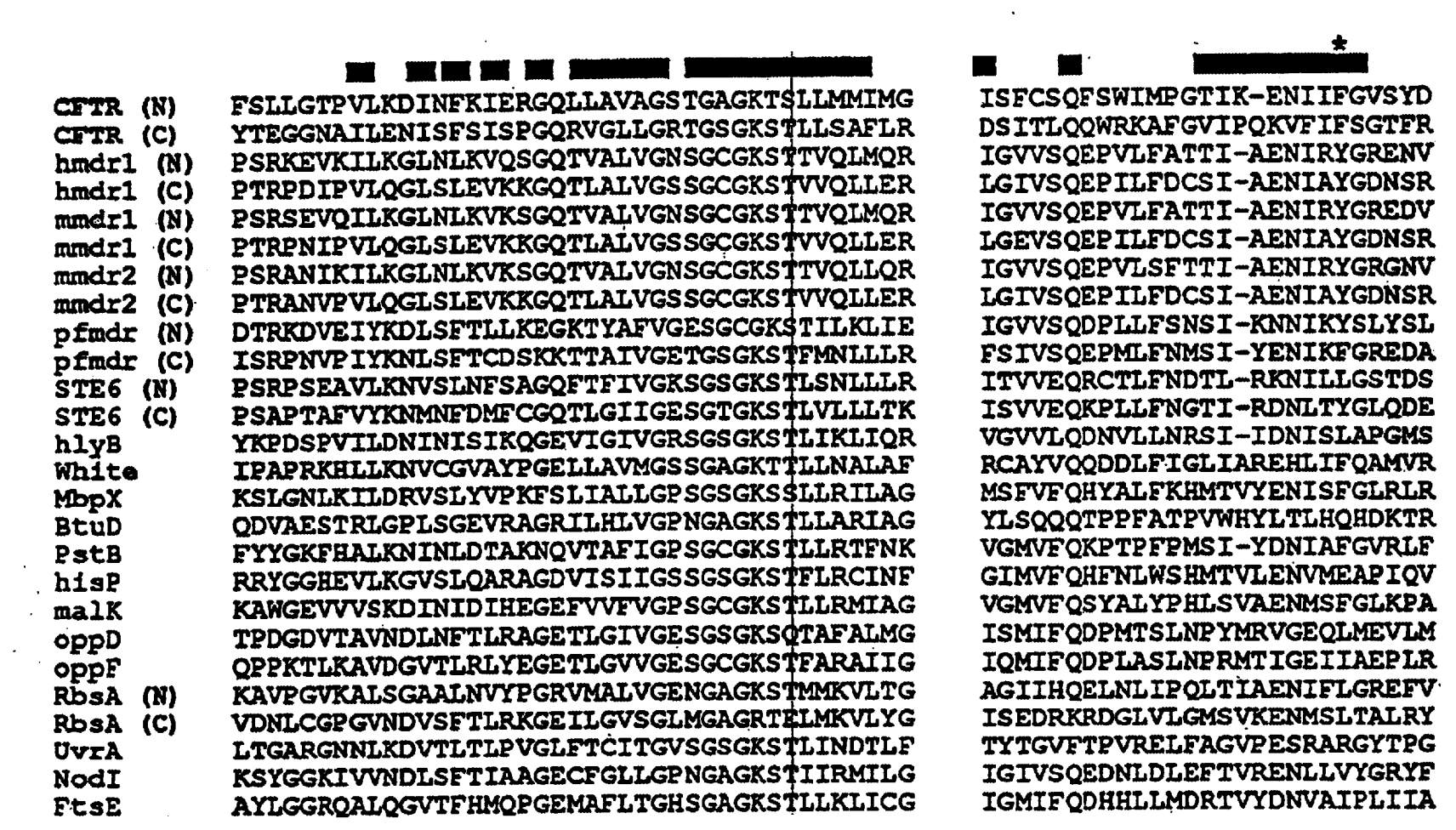

Each of the predicted membrane-associated regions of the CFTR protein consists of 6 highly hydrophobic segments capable of spanning a lipid bilayer according to the algorithms of Kyte and Doolittle and of Garnier et al (*J. Mol. Biol.* 120, 97 (1978) (FIG. 13). The membrane-associated regions are each follow d by a large hydrophilic region containing the NBFs. Based on sequence alignment with other known nucleotide binding proteins, each of the putative NBFs in CFTR comprises at least 150 residues (FIG. 13). The 3 bp deletion detected in the majority of CF patients is located between the 2 most highly conserved segments of the first NBF in CFTR. The amino acid sequence identity between the region surrounding the phenylalanine deletion and the corresponding regions of a number of other proteins suggests that this region is of functional importance (FIGS. 16A–16B). A hydrophobic amino acid, usually one with an aromatic aide chain, is present in moat of these proteins at the position corresponding to F508 of the CFTR protein. It is understood that amino acid polymorphism may exist as a result of DNA polymorphisms.

FIGS. 16A–16B shows alignment of the 3 most conserved segments of the extended NBF's of CFTR with comparable regions of other proteins. These 3 segments consist of residues 433–473, 488–513, and 542–584 of the N-terminal half and 1219–1259, 1277–1302, and 1340–1382 of the C-terminal half of CFTR. The heavy overlining points out the regions of greatest similarity. Additional general homology can be seen even without the introduction of gaps.

Figure 12:
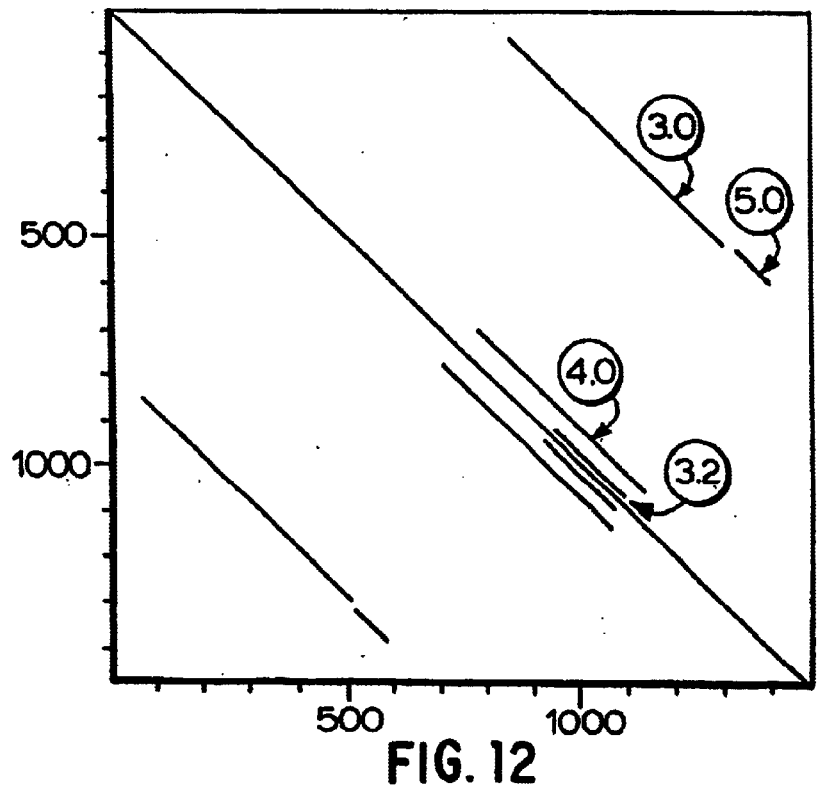
FIG. 12 is a dot matrix analysis of internal homologies in the predicted CFTR polypeptide.

Despite the overall symmetry in the structure of the protein and the sequence conservation of the NBFs, sequence homology between the two halves of the predicted CFTR protein is modest. This is demonstrated in FIG. 12, where amino acids 1-1480 are represented on each axis. Lines on either side of the identity diagonal indicate the positions of internal similarities. Therefore, while four sets of internal sequence identity can b detected as shown in FIG. 12, using the Dayhoff scoring matrix as applied by Lawrence at al. (C. B. Lawrence, D. A. Goldman, and R. T. Hood, *Bull Math Biol*, 48, 569 (1986)), three of these are only apparent at low threshold settings for standard deviation. The strongest identity is between sequences at the carboxyl ends of the NBFs. Of the 66 residues aligned 27% are identical and another 11% are functionally similar. The overall weak internal homology is in contrast to the much higher degree (>70%) in P-glycoprotein for which a gene duplication hypothesis has been proposed (Gros et al, *Cell* 47, 371, 1986, C. Chan et al, *Cell* 47, 381, 1986, Gerlach et al, *Nature*, 324, 485, 1986, Gros et al, *Mol. Cell. Biol.* 8, 2770, 1988). The lack of conservation in the relative positions of the exon-intron boundaries may argue against such a model for CF M (FIGS. 2A–2G).

Since there is apparently no signal-peptide sequence at the amino-terminus of CFTR, the highly charged hydrophilic segment preceding the first transmembrane sequence is probably oriented in the cytoplasm. Each of the 2 sets of hydrophobia helices are expected to form 3 transversing loops across the membrane and little sequence of the entire protein is expected to be exposed to the exterior surface, except the region between transmembrane segment 7 and 8. It is of interest to note that the latter region contains two potential sites for N-linked glycosylation.

Each of the membrane-associated regions is followed by a NBF as indicated above. In addition, a highly charged cytoplasmic domain can be identified in the middle of the predicted C m polypeptide, linking the 2 halves of the protein. This domain, named the R-domain, is operationally defined by a single large axon in which 69 of the 241 amino acids are polar residues arranged in alternating clusters of positive and negative charges. Moreover, 9 of the 10 consensus sequences required for phosphorylation by protein kinase A (PKA), and, 7 of the potential substrate sites for protein kinase C (PKC) found in CFTR are located in this exon.

4.2 Function of CFTR

Properties of CFTR can be derived from comparison to other membrane-associated proteins (FIGS. 16A–16B). In addition to the overall structural similarity with the mammalian P-glycoprotein, each of the two predicted domains in CFTR also shows remarkable resemblance to the single domain structure of hemolysin B of *E. coli* and the product of the White gene of *Drosophila*. These latter proteins are involved in the transport of the lytic peptide of the hemolysin system and of eye pigment molecules, respectively. The vitamin B12 transport system of *E. coli*, BtuD and MbpX which is a liverwort chloroplast gene whose function is unknown also have a similar structural motif. Furthermore, the CFTR protein shares structural similarity with several of the periplasmic-solute transport systems of gram negative bacteria where the transmembrane region and the ATP-binding folds are contained in separate proteins which function in concert with a third substrate-binding polypeptide.

The overall structural arrangement of the transmembrane domains in CFTR is similar to several cation channel proteins and some cation-translocating ATPases as well as the recently described adenylate cyclase of bovine brain. The functional significance of this topological classification, consisting of 6 transmembrane domains, remains speculative.

Short regions of sequence identity have also been detected between the putative transmembrane regions of CFTR and other membrane-spanning proteins. Interestingly, there are also sequences, 18 amino acids in length situated approximately 50 residues from the carboxyl terminus of CFTR and the raf serine/threonine kinase protooncogene of *Xanopus laevis* which are identical at 12 of these positions.

Finally, an amino acid sequence identity (10/13 conserved residues) has been noted between a hydrophilic segment (position 701-713) within the highly charged R-domain of CFTR and a region immediately preceding the first transmembrane loop of the sodium channels in both rat brain and eel. The charged R-domain of CFTR is not shared with the topologically closely related P-glycoprotein; the 241 amino acid linking-peptide is apparently the major difference between the two proteins.

In summary, features of the primary structure of the CFTR protein indicate its possession of properties suitable to participation in the regulation and control of ion transport in the epithelial cells of tissues affected in CF. Secure attachment to the membrane in two regions serve to position its three major intracellular domains (nucleotide-binding folds 1 and 2 and the R-domain) near the cytoplasmic surface of the cell membrane where they can modulate ion movement through channels formed either by CFTR transmembrane segments themselves or by other membrane proteins.

In view of the genetic data, the tissue-specificity, and the predicted properties of the CFTR protein, it is reasonable to conclude that CFTR is directly responsible for CF. It, however, remains unclear how CFTR is involved in the regulation of ion conductance across the apical membrane of epithelial cells.

It is possible that CFTR serves as an ion channel itself. As depicted in FIG. 13, 10 of the 12 transmembrane regions contain one or more amino acids with charged side chains, a property similar to the brain sodium channel and the GABA receptor chloride channel subunits, where charged residues are present in 4 of the 6, and 3 of the 4, respective membrane-associated domains per subunit or rep at unit. The amphipathic nature of these transmembrane segments is believed to contribute to the channel-forming capacity of these molecules. Alternatively, CFTR may not be an ion channel but instead serve to regulate ion channel activities. In support of the latter assumption, none of the purified polypeptides from trachea and kidney that are capable of reconstituting chloride channels in lipid membranes (Landry et al, *Science* 224:1469 (1989)) appear to be CFTR if judged on the basis of the molecular mass.

In either case, the presence of ATP-binding domains in CFTR suggests that ATP hydrolysis is directly involved and required for the transport function. The high density of phosphorylation sites for PKA and PKC and the clusters of charged residues in the R-domain may both serve to regulate this activity. The deletion of a phenylalanine residue in the NBF may prevent proper binding of ATP or the conformational change which this normally elicits and consequently result in the observed insensitivity to activation by PKA- or PKC-mediated phosphorylation of the CF apical chloride conductance pathway. Since the predicted protein contains several domains and belongs to a family of proteins which frequently function as parts of multi-component molecular systems, CFTR may also participate in epithelial tissue functions of activity or regulation not related to ion transport.

With the isolated CF gene (cDNA) now in hand it is possible to define the basic biochemical defect in CF and to further elucidate the control of ion transport pathways in epithelial cells in general. Most important, knowledge gained thus far from the predicted structure or CFTR tog there with the additional information from studies of the protein itself provide a basis for the development of improved means of treatment of the disease. In such studies, antibodies have been raised to the CFTR protein as later described.

4.3 Protein Purification

The CFTR protein can be purified by methods selected on the basis of properties as revealed by its sequence. For example, since it possesses distinctive properties of an integral membrane protein, a membrane fraction of the epithelial cells in which it is highly expressed (e.g., the cultured colonic carcinoma cell line, T84) is first isolated using established methods (J. E. Langridge, et al, *Biochim. Biophys. Acts.* 751: 318 (1983)). The peripheral proteins of these membranes are those removed by extraction with high salt concentrations, high pH or chaotropic agents such as lithium diiodosalicylate. All of the integral proteins remaining including the CFTR protein are then solubilized using a detergent such as octyl glucoside (Landry, et al, supra), CHAPS (D. J. Beros et al, *J. Biol. Chem.* 262: 10613 (1987)), or other compounds of similar action. Making use of the nucleotide binding domains of CFTR, cibacron-blue (S. T. Thompson et al. *Proc. Nat, Acad. Sci. U.S.A.* 72: 669 (1975)) affinity chromatography is then used to bind the CFTR protein and remove it from other integral proteins of the detergent stabilized mixture. Since CFTR is a glycoprotein, differential lectin chromatography can bring about further purification (Riordan et al. *J. Biol. Chem,* 254: 1270 (1979)). Final purification to homogeneity is then achieved using other standard protein purification procedures; i.e., ion exchange chromatography, gel permeation chromatography, adsorption chromatography or isoelectric focussing as necessary. Alternatively, use is made of single step purification procedures, such as immuno-affinity chromatography using immobilized antibodies to the CFTR protein (or fragments thereof) or preparative polyacrylamide gel electrophoresis using advanced instrumentation such as the Applied Biosystems "230A HPEC System". Based on experience in the purification of P-glycoprotein (Riordan et al, supra), another member of the general category of nucleotide binding transport-associated membrane proteins, the purification of the CFTR protein is facilitated.

In addition to purification from tissues and cells in which the CFTR protein is highly expressed, similar procedures are used to purify CFTR from calls transfected with vectors containing the CF gene (cDNA) as described above. Protein products resulting from expression of modified version of the cDNA sequence are purified in a similar manner. Criteria of the homogeneity of protein so provided include those standard to the field of protein chemistry including one and two dimensional gel electrophoresis and N-terminal amino acid determination. The purified protein is used in further physical biochemical analysis to determine features of its secondary and tertiary structure, to aid in the design of drugs to promote the proper functioning of the mutant CF forms. In preparation for use in protein therapy, the absence of potentially toxic contaminating substances is considered. It is recognized that the hydrophobic nature of the protein necessitates the inclusion of amphiphilic compounds such as detergents and others (J. V. Ambud Kar and P. C. Maloney *J. Biol. Chem.* 261: 10079 (1986)) at all stages of its handling.

5.0 CF Screening 5.1 DNA Based Diagnosis

Given the knowledge of the major mutation as disclosed herein, carrier screening and prenatal diagnosis can be carried out as follows.

The high risk population for cystic fibrosis is Caucasians. For example, each Caucasian woman and/or man of child-bearing age would be screened to determine if she or he was a carrier (approximately a 5% probability for each individual). If both are carriers, they are a couple at risk for a cystic fibrosis child. Each child of the at risk couple has a 25% chance of being affected with cystic fibrosis. The procedure for determining carrier status using the probes disclosed herein is as follows.

One major application of the DNA sequence information of the normal and mutant CF genes is in the area of genetic testing, carrier detection and prenatal diagnosis. Individuals carrying mutations in the CF gene (disease carrier or patients) may be detected at the DNA level with the use of a variety of techniques. The genomic DNA used for the diagnosis may be obtained from body cells, such as those present in peripheral blood, urine, saliva, tissue biopsy, surgical specimen and autopsy material. The DNA may be used directly for detection of specific sequence or may be amplified enzymatically in vitro by using PCR (Saiki et al. *Science* 230: 1350–1353, (1985), Saiki et al. *Nature* 324: 163–166 (1986)) prior to analysis. RNA or its cDNA form may also be used for the same purpose. Recent reviews of this subject have been presented by Caskey, (*Science* 236: 1223-8 (1989) and by Landegren et al (*Science* 242: 229–237 (1989).

The detection of specific DNA sequences may be achieved by methods such as hybridization using specific oligonucleotides (Wallace et al. *Cold Spring Harbour Symp. Quant. Biol.* 51: 257–261 (1986)), direct DNA sequencing (Church and Gilbert, *Proc. Nat. Acad. Sci. U. S. A.* 81: 1991–1995 (1988)), the use of restriction enzymes (Flavell et al. *Cell* 15: 25 (1978), Geever et al *Proc. Nat. Acad. Sci. U.S.A.* 78: 5081 (1981)), discrimination on the basis of electrophoretic mobility in gels with denaturing reagent (Myers and Maniatis, *Cold Spring Harbour Sym. Quant Biol.* 51: 275–284 (1986)), RNase protection (Myers, R. M., Larin, J., and T. Maniatis *Science* 230: 1242 (1985)), chemical cleavage (cotton et al *Proc. Nat, Acad. Sci, U. S. A.* 95: 4397–4401, (1985)) and the ligase-mediated detection procedure (Landegren at al *Science* 241:1077 (1988)).

Oligonucleotides specific to normal or mutant sequences are chemically synthesized using commercially available machines, labelled radioactively with isotopes (such as $^{32}$P) or non-radioactively (with tags such as biotin (Ward and Langer et al. *Proc. Nat. Acad. Sci. U. S. A.* 78: 6633–6657

(1981)), and hybridized to individual DNA samples immobilized on membranes or other solid supports by dot-blot or transfer from gels after electrophoresis. The presence or absence of these specific sequences are visualized by methods such as autoradiography or fluorometric (Landegren at al, 1989, supra) or colorimetric reactions (Gebeyehu et al. *Nucleic Acids Research* 15: 4513–4534 (1987)). An embodiment of this oligonucleotide screening method has been applied in the detection of the F508 deletion as described herein.

Sequence differences between normal and mutants may be revealed by the direct DNA sequencing method of Church and Gilbert (supra). Cloned DNA segments may be used as probes to detect specific DNA segments. The sensitivity of this method is greatly enhanced when combined with PCR (Wrichnik et al, *Nucleic Acids Res.* 15:529–542 (1987) Wong et al, *Nature* 330:384–386 (1987); Stoflet et al, *Science* 239:491–494 (1988). In the latter procedure, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent-tags.

Sequence alterations may occasionally generate fortuitous restriction enzyme recognition sites which are revealed by the use of appropriate enzyme digestion followed by conventional gel-blot hybridization (Southern, *J. Mol. Biol* 98: 503 (1975)). DNA fragments carrying the site (either normal or mutant) are detected by their reduction in size or increase of corresponding restriction fragment numbers. Genomic DNA samples may also be amplified by PCR prior to treatment with the appropriate restriction enzymes fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high resolution gel electrophoresis. For example, the PCR product with the 3 bp deletion is clearly distinguishable from the normal sequence on an 8% non-denaturing polyacrylamide gel. DNA fragments of different sequence compositions may be distinguished on denaturing formamide gradient gel in which the mobilities of different DNA fragments are retarded in the gal at different positions according to their specific "partial-melting" temperatures (Myers, supra). In addition, sequence alterations, in particular small deletions, may be detected as changes in the migration pattern of DNA heteroduplexes in non-denaturing gel electrophoresis, as have been detected for the 3 bp (F508) mutation and in other experimental systems (Nagamine et al, *Am. J. Hum. Genet,* 45:337–339 (1989)). Alternatively, a method of detecting a mutation comprising a single base substitution or other small change could be based on differential primer length in a PCR. For example, on invariant primer could be used in addition to a primer specific for a mutation. The PCR products of the normal and mutant genes can then be differentially detected in acrylamide gels.

Sequence changes at specific locations may also be revealed by nuclease protection assays, such as RNase (Myers, supra) and S1 protection (Berk, A. J., and P. A. Sharpe *Proc. Nat. Acad. Sci. U.S.A.* 75: 1274 (1978)), the chemical cleavage method (Cotton, supra) or the ligase-mediated detection procedure (Landegren supra).

In addition to conventional gel-electrophoresis and blot-hybridization methods, DNA fragments may also be visualized by methods where the individual DNA samples are not immobilized on membranes. The probe and target sequences may be both in solution or the probe sequence may be immobilized (Saiki et al, *Proc. Natl. Acad. Sci U.S.A.,* 86:6230–6234 (1989)). A variety of detection methods, such as autoradiography involving radioisotopes, direct detection of radioactive decay (in the presence or absence of scintillant), spectrophotometry involving colorigenic reactions and fluorometry involving fluorogenic reactions, may be used to identify specific individual genotypes.

Since more than one mutation is anticipated in the CF gene, a multiples system is an ideal protocol for screening CF carriers and detection of specific mutations. For example, a PCR With multiple, specific oligonucleotide primers and hybridization probes, may be used to identify all possible mutations at the same time (Chamberlain et al. *Nucleic Acids Research* 16: 1141–1155 (1988)). The procedure may involve immobilized sequence-specific oligonucleotides probes (Saiki et al, supra).

5.2 Detecting the Major Mutation

These detection methods may be applied to prenatal diagnosis using amniotic fluid cells, chorionic villi biopsy or sorting fetal cells from maternal circulation. The test for CF carriers in the population may be incorporated as an essential component in a broad-scale genetic testing program for common diseases.

According to an embodiment of the invention, the portion of the DNA segment that is informative for a mutation, such as the mutation according to this embodiment, that is, the portion that immediately surrounds the F508 deletion, can then be amplified by using standard PCR techniques (as reviewed in Landegren, Ulf, Robert Kaiser, C. Thomas Caskey, and Leroy Hood, DNA Diagnostics-Molecular Techniques and Automation, in Science 242: 229–237 (1988)). It is contemplated that the portion of the DNA segment which is used may be a single DNA segment or a mixture of different DNA segments. A detailed description of this technique now follows.

A specific region of genomic DNA from the person or fetus is to be screened. Such specific region is defined by the oligonucleotide primers C16B (5'GTTTT CCTGGATTATGCCTGGGCAC3') (SEQ ID NO:6) and C16D (5'GTTGGCATGCTTGATGACGCTTC3') (SEQ ID NO.7). The specific regions were amplified by the polymerase chain reaction (PCR). 200–400 ng of genomic DNA, from either cultured lymphoblasts or peripheral blood samples of CF individuals and their parents, were used in each PCR with the oligonucleotides primers indicated above. The oligonucleotides were purified with Oligonucleotide Purification Cartridges™ (Applied Biosystems) or NENSORB™ PREP columns (Dupont) with procedures recommended by the suppliers. The primers were annealed at 62° C. for 45 sec, extended at 72° C. for 120sec (with 2 units of Taq DNA polymerase) and d natured at 94° C. for 60 sec, for 28 cycles with a final cycle at 7 min for extension in a Perkin-Elmer/Cetus automatic thermocycler with a Step-Cycle program (transition setting at 1.5 min). Portions of the PCR products were separated by electrophoresis on 1.4% agarose gels, transferred to Zetabindu™; (Biorad) membrane according to standard procedures. The two oligonucleotide probes of FIG. 15 (10 ng each) were labeled separately with 10 units of T4 polynucleotide kinase (Pharmacia) in a 10 μl reaction containing 50 mM Tris-HCl (pH7.6), 10 mM Mgcl$_2$, 0.5 MM dithiothreitol, 10 mM spermidine, 1 mM EDTA and 30–40 µCi of γ[$^{32}$P]-ATP for 20–30 min at 37° C. The unincorporated radionucleotides were removed with a Sephadax G-25 column before use. The hybridization conditions were as described previously (J. M. Rommens at al *Am. J. Hum. Genet.* 43,645 (1988)) except that the temperature was 37° C. The membranes were washed twice at room temperature with 5×SSC and twice at 39° C. with 2×SSC (1×SSC=150 mM NaCl and 15 mM Na citrate). Autoradiography was performed at room temperature overnight. Autoradiographs show the hybridization results of genomic DNA with the 2 Specific oligonucleotide probes as indicated in FIG. 15. Probe C detects the normal DNA sequence and Probe F detects the mutant sequence. Genomic DNA sample from each family member was amplified by the polymerase chain reaction and the products separated by electrophoresis on a 1.4% agarose gel and then transferred to Zetabind (Biorad) membrane according to standard procedures. Water blank and plasmid DNA, T16 and C16, corresponding to the normal sequence (N) and the 7508 deletion (CF), respectively, were included as controls.

The 3 bp deletion was also revealed by polyacrylamide gel electrophoresis. When the PCR generated by the above-mentioned C16B and C16D primers were applied to an 8% polyacrylamide gel, electrophoresed for 2 hrs at 20 V/cm in a 90AM Tris-borate buffer (pH 8.3), DNA fragments of a different mobility were clearly detectable for individuals without the 3 bp deletion, heterozygous or homozygous for the deletion. In addition, an extra DNA band, presumably the heteroduplex between normal and mutant DNA strands, was noted in heterozygotes. Similar alteration in gel mobility for heteroduplexes formed during PCR has also been reported for experimental systems where small deletions are involved (Nagamine et al supra). These mobility shifts may be used an the basis for the non-radioactive genetic screening tests.

5.3 CF Screening Programs

It is appreciated that only 70% of the carriers can be detected using the specific F508 probes of this particular embodiment of the invention. Thus, if an individual tested is not a carrier using the F508 probes, their carrier status can not be excluded, they may carry some other mutation as previously noted. However, if both the individual and the spouse of the individual tested are a carrier for the F508 mutation, it can be stated with certainty that they are an at risk couple. The sequence of the gone an disclosed herein is an essential prerequisite for the determination of the other mutations.

Prenatal diagnosis is a logical extension of carrier screening. A couple can be identified as at risk for having a cystic fibrosis child in one of two ways: if they already have a cystic fibrosis child, they are both, by definition, obligate carriers of the disease, and each subsequent child has a 25% chance of being affected with cystic fibrosis. A major advantages of the present invention eliminates the need for family pedigree analysis, whereas, according to this invention, a gene mutation screening program as outlined above or other similar method can be used to identify a genetic mutation that leads to a protein with altered function. This is not dependent on prior ascertainment of the family through an affected child. Petal DNA samples, for example, can be obtained, as previously mentioned, from amniotic fluid cells and chorionic villi specimens. Amplification by standard PCR techniques can then be performed on this template DNA.

If both parents are shown to be carriers with the F508 deletion, the interpretation of the results would be the following. If there is hybridization of the fetal DNA to the normal (no deletion, as shown in FIG. 15) probe, the fetus will not be affected with cystic fibrosis, although it may be a CF carrier (50% probability for each fetus of an at risk couple). If the fetal DNA hybridizes only to the F508 deletion probe and not to the normal probe (as shown in FIG. 15), the fetus will be affected with cystic fibrosis.

It is appreciated that for this and other mutations in the CF gene, a range of different specific procedures can be used to provide a complete diagnosis for all potential CF carriers or patients. A complete description of these procedures is later described.

The invention therefore provides a method and kit for determining if a subject is a CF carrier or CF patient. In summary, the screening method comprises the steps of:

providing a biological sample of the subject to be screened; and providing an assay for detecting in the biological sample, the presence of at least a member from the group consisting of the normal CF gene, normal CF gene products, a mutant CF genes mutant CF gene products and mixtures thereof.

The method may be further characterized by including at least one more nucleotide probe which is a different DNA sequence fragment of, for example, the DNA of FIGS. 1A–1H, or a different DNA sequence fragment of human chromosome 7 and located to either side of the DNA sequence of FIGS. 1A–1H.

A kit, according to an embodiment of the invention, suitable for use in the screening technique and for assaying for the presence of the CF gene by an immunoassay comprises:

(a) an antibody which specifically binds to a gene product of the CF gene;

(b) reagent means for detecting the binding of the antibody to the gene product; and (c) the antibody and reagent means each being present in amounts effective to perform the immunoassay.

The kit for assaying for the presence for the CF gene may also be provided by hybridization techniques.

The kit comprises:

(a) an oligonucleotide probe which specifically binds to the CF gene;

(b) reagent means for detecting the hybridization of the oligonucleotide probe to the CF gene; and (c) the probe and reagent means each being present in amounts affective to perform the hybridization assay.

5.4 Antibodies to Detect CFTR

As mentioned, antibodies to epitopes within the CFTR protein are raised to provide extensive information on the characteristics of the protein and other valuable information which includes:

1. To enable visualization of the protein in cells and tissues in which it is expressed by immunoblotting ("Western blots") following polyacrylamide gel electrophoresis. This allows an estimation of the molecular size of the mature protein including the contribution from the cells of post-translationally added moieties including oligosaccharide chains and phosphate groups, for example. Immunocytochemical techniques including immunofluorescence and immuno-el etron-microscopy can be used to establish the subcellular localization of the protein in cell membranes. The antibodies can also be used to provide another technique in detecting any of the other CF mutations which result in the synthesis of a protein with an altered size.

2. Antibodies to distinct domains of the protein can be used to determine the topological arrangement of the protein in the cell membrane. This provides information on segments of the protein which are accessible to externally added modulating agents for purposes of drug therapy.

3. The structure-function relationships of portions of the protein can be examined using specific antibodies. For example, it is possible to introduce into cells antibodies recognizing each of the charged cytoplasmic loops which join the transmembrane sequences as well as portions of the nucleotide binding folds and the R-domain. The influence of these antibodies on functional parameters of the protein provide insight into cell regulatory mechanisms and potentially suggest means of modulating the activity of the defective protein in a CF patient.

4. Antibodies with the appropriate avidity also enable immunoprecipitation and immuno-affinity purification of the protein. Immunoprecipitation will facilitate characterization of synthesis and post translational modification including ATP binding and phosphorylation. Purification will be required for studies of protein structure and for reconstitution of its function, as well as protein based therapy.

Figure 19A:
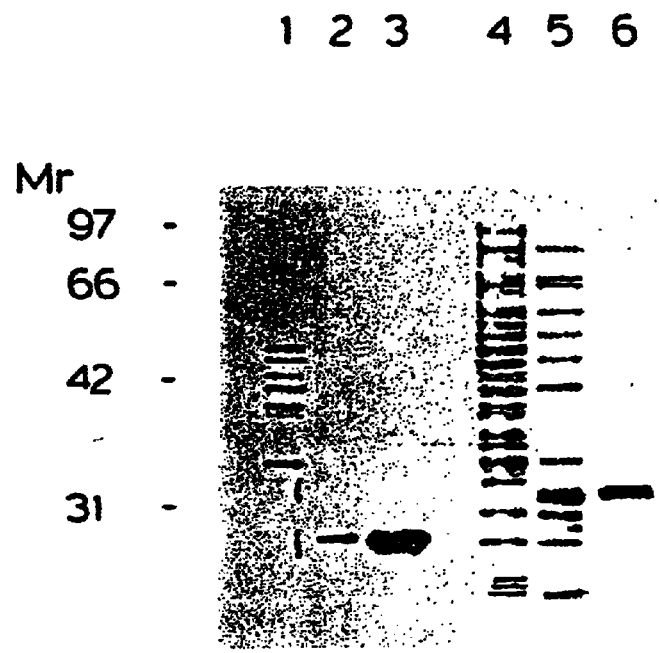
FIGS. 19A and 19B are Coomassie Blue stained polyacrylamide gels following electrophoresis of protein from bacterial lysates (JM 101) which bacteria was transformed with the pGEX plasmids.
Figure 19B:
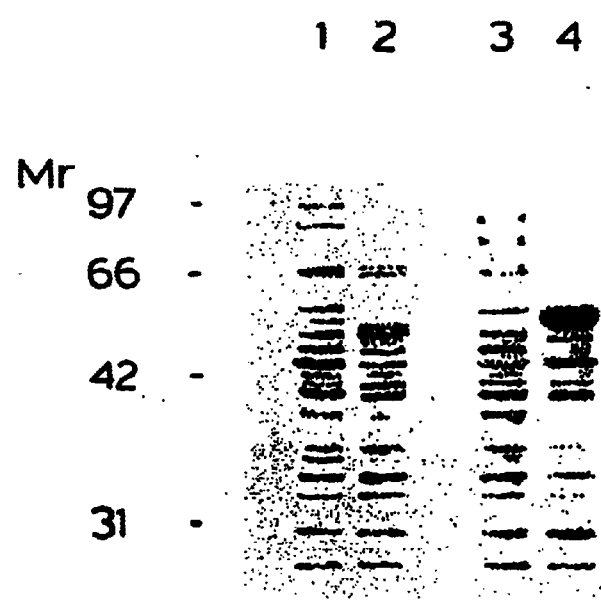
Figures 20, 21:
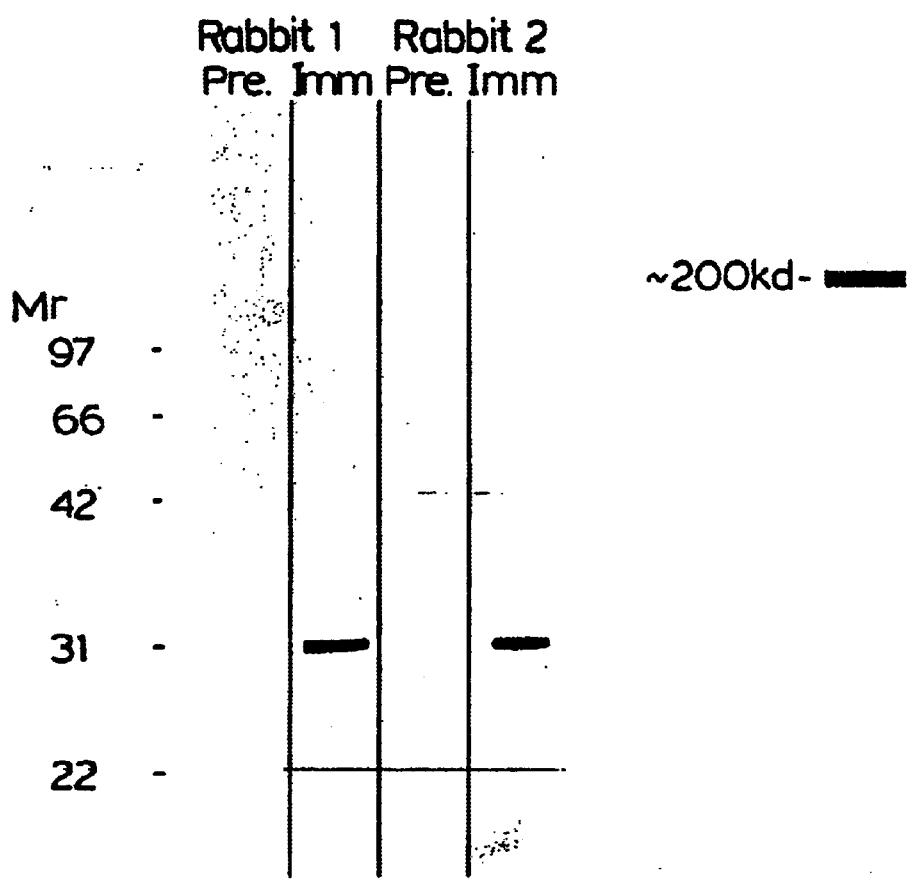
FIG. 20 is immunoblots of bacterial lysates containing fusion protein #1 (on Table 8) with preimmune and immune sera from two different rabbits.
FIG. 21 is an immunoblot of T-84 membranes using immune serum from rabbit #1 of FIG. 20.

In order to prepare the antibodies, fusion proteins containing defined portions of CFTR polypeptides have been synthesized in bacteria by expression of corresponding DNA sequence in a suitable cloning vehicle whereas smaller peptides were synthesized chemically as described in Table 8. The fusion proteins were purified, for example, by affinity chromatography on glutathione-agarose and the peptides were coupled to a carrier protein (hemocyanin), mixed with Freund's adjuvant and injected into rabbits. Following booster injections at bi-weekly intervals, the rabbits were bled and sera isolated. The stained fusion proteins are shown in FIG. 19A. Lane 1, uninduced control plasmid; lane 2, IPTG-induced control plasmid expressing just glutathione-S-transferase (GST); lane 3, affinity purified GST band at 27 kilodaltons (kD); lane 4 is uninduced, lane 5 is induced and lane 6 is the purified fusion protein #1 of Table 8. In FIG. 19B, the gel electrophoresis is of lysates from bacteria transformed with pGEX plasmids containing fusion proteins #5 of Table 8 for lanes 1 and 2 and fusion proteins #2 of Table 8 for lanes 3 and 4. Lane 1 of FIG. 19B is for the uninduced plasmid whereas lane 2 is for the induced plasmid to express the fusion protein #5. Lane 3 of FIG. 19B is for the uninduced plasmid whereas lane 4 is for the induced plasmid to express the fusion protein #2. Immunoblots of fusion protein #1 probed with antisera obtained from the second bleeds of two different rabbits are shown in FIG. 20. The staining is with alkaline-phosphatase conjugated second antibody (Blake et al, al, *Anal. Biochem.* 136:175, (1984)). Both of these immune sera stain the 32 kD fusion protein whereas the preimmune sera do not. FIG. 21 shows the reactivity of one of these immune sera with a band of approximately 200 kD in size in membranes isolated from T-84 colonic carcinoma cells which express the CFTR transcript at a high level. This band is in the size range which might be expected for the CFTR protein which has a predicted molecular weight of 169 kD prior to post-translational modifications.

Figure 22:
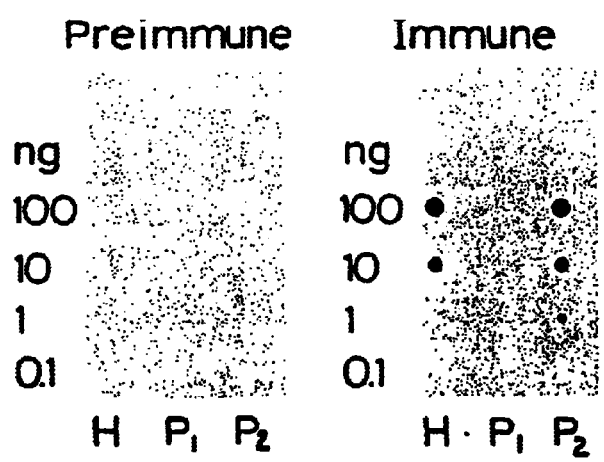
FIG. 22 is immunodot blots probed with preimmune and immune sera from a rabbit immunized with the KLH conjugate of peptide #2 of Table 8.

Sera from rabbits immunized with the LKH conjugate of peptide #2 were screened again both pure peptide and KLH as shown in FIG. 22. In this Figure, H denotes hemocyanin; P1, peptide #1: P2, peptide #2. Amounts of protein or peptide dotted in ng are indicated. This antiserum detects as little as 1 ng of the peptide and does not react at all with control peptide #1.

Thus, it is possible to raise polyclonal antibodies specific for both fusion proteins containing portions of the CFTR protein and peptides corresponding to short segments of its sequence. Similarly, mice can be injected with KLH conjugates of peptides 1, 2 and 7 of Table 8 to initiate the production of monoclonal antibodies to these segments of CFTR protein. Monoclonal antibodies can be similarly raised to other domains of the CFTR protein.

An for the generation of polyclonal antibodies, immunogens for the raising of monoclonal antibodies (mAbs) to the CFTR protein are bacterial fusion proteins (Smith et al, *Gene* 67:31 (1988)) containing portions of the CFTR polypeptide or synthetic peptides corresponding to short (12 to 25 amino acids in length) segments of the sequence. The essential methodology is that of Kohler and Milstein (*Nature* 256: 495 (1975).

Balb/a mice are immunized by intraperitoneal injection with 500 $\mu$g of pure fusion protein or synthetic peptide in incomplete Freund's adjuvant. A second injection is given after 14 days, a third after 21 days and a fourth after 28 days. Individual animals, so immunized are sacrificed one, two and four weeks following the final injection. Spleens are removed, their cells dissociated, collected and fused with Sp2/0-Ag14 myeloma cells according to Gefter et al, *Somatic Call Genetics* 3:231 (1977). The fusion mixture is distributed in culture medium selective for the propagation of fused cells which are grown until they are about 25% confluent. At this time, culture supernatants are tested for the presence of antibodies reacting with a particular CFTR antigen. An alkaline phosphatase labelled anti-mouse second antibody is then used for detection of positives. Cells from positive culture wells are then expanded in culture, their supernatants collected for further testing and the cells stored deep frozen in cryoprotectant-containing medium. To obtain large quantities of a mAb, producer cells are injected into the peritoneum at $5\times10^6$ cells per animal, and ascites fluid is obtained. Purification is by chromotography on Protein G- or Protein A-agarose according to Ey et al, *Immunochemistry* 15:429 (1977).

Reactivity of these mAbs with the CFTR protein is confirmed by polyacrylamide gel electrophoresis of membranes isolated from epithelial cells in which it is expressed and immunoblotting (Towbin at al, *Proc. Natl. Acad. Sci. USA* 76:4350 (1979)).

In addition to the use m monoclonal antibodies specific for each of the different domains of the CFTR protein to probe their individual functions, other mAbs, which can distinguish between the normal and mutant forms of CFTR protein, are used to detect the mutant protein in epithelial call samples obtained from patients, such as nasal mucosa biopsy "brushings"(R. De-Lough and J. Rutland, *J. Clin. Pathol.* 42, 613(1989)) or skin biopsy specimens containing sweat glands.

Antibodies capable of this distinction are obtained by differentially screening hybridomas from paired sets of mice immunized with a peptide containing the phenylalanine at amino acid position 508 (e.g. GTIKENIIEGVSY) (SEQ ID NO.8) or a peptide which is identical except for the absence of P508 (GTIKENIIGVSY) (SEQ ID NO.11 mAbs capable of recognizing the other mutant forms of CFTR protein present in patients in addition or instead of F508 deletion are obtained using similar monoclonal antibody production strategies.

Antibodies to normal and CF versions of CFTR protein and of segments thereof are used in diagnostically immunocytochemical and immunofluorescence light microscopy and immunoelectron microscopy to demonstrate the tissue, cellular and subcellular distribution of CFTR within the organs of CF patients, carriers and non-CF individuals.

Antibodies are used to therapeutically modulate by promoting the activity of the CFTR protein in CF patients and in cells of CF patients. Possible modes of such modulation might involve stimulation due to cross-linking of CFTR protein molecules with multivalent antibodies in analogy with stimulation of some cell surface membrane receptors, such as the insulin receptor (O'Brien et al, *Euro. Mol. Biol. Organ. J.* 6:4003 (1987)), epidermal growth factor receptor (Schreiber et al, *J. Biol. Chem.* 258:846 (1983)) and T-cell receptor-associated molecules such as CD4(Veillette et al *Nature,* 338:257 (1989)).

Antibodies are used to direct the delivery of therapeutic agents to the cells which express defective CFTR protein in CF. For this purpose, the antibodies are incorporated into a vehicle such as a liposome (Matthay et al, *Cancer Res.* 46:4904 (1896)) which carries the therapeutic agent such as a drug or the normal gene.

TABLE 8

CFTR FRAGMENTS USED TO RAISE ANTIBODIES

| GST[a] fusion proteins containing CFTR residues | CFTR Domain of FIG. 13 |
|---|---|
| 1. 204–249 | TM3, Ext. 2, TMA |
| 2. 347–698 | NBF-1, N-term 1/2 R-domain |
| 3. 710–757 | Neg. charged middle of R-domain |
| 4. 758–796 | Pos. charged segment of R-domain |
| 5. 1188–1480 | C-term. cyto. domain with NBF-2 |
| KLH[b] conjugates containing CFTR peptides: | |
| 1. 28–45 | N-term. cytoplasmic |
| 2. 58–75 | N-term. cytoplasmic |
| 3. 104–117 | 1st extracellular |
| 4. 139–153 | 2nd cytoplasmic |
| 5. 279–294 | N-term. of 3rd cytoplasmic |
| 6. 500–512 | NBF-1; around the F508 deletion |
| 7. 725–739 | Charged middle of R-domain |
| 8. 933–946 | 5th cytoplasmic |
| 9. 1066–1084 | 6th cytoplasmic |

[a]restriction fragments coding for these fragments ligated to 3' end of glutathione S-transferase (GST) of *Schistosoma japonicum* in pGEX plasmid expression vector as identified in Smith et al, Gene 67:31, (1988).
[b]Peptides coupled through an N-terminal cysteine to the carrier protein keyhole limpet hemocyanin (KLH) according to Green et al Cell 28:477 (1982). TM denotes transmembrane sequences.

5.5 RFLP Analysis

This invention provides a number of benefits stemming directly from the discovery and characterization of the CF gene which are of immediate practical application. The amino acid sequence of CFTR provides insight into the structure and function of the protein as well am the molecular mechanisms in which CFTR participates and which are defective in cystic fibrosis. This information enables the generation of further tools and concepts, in research on and therapy for this disease.

Carrier detection, DNA diagnosis and family counselling are some of the applications of the invention. Previously DNA-based genetic testing for CF has primarily been available to families with affected children and to their close relatives. Knowledge of the CF mutations at the DNA sequence level permits testing of any random individual; our estimate shows that 46% of CF patients without a previous family history can be accurately diagnosed by DNA analysis, and 68% of the CF carriers in the population can be identified via the F508 deletion.

Given that the carrier frequency in the North American population is approximately 1 in 20, it is feasible to screen all women and/or men of child-bearing age, for example, for their carrier status. Carrier detection using probes specific for the F508 deletion will pick up 70% of the carriers. The remaining carriers will be detected by a battery of probes specific for the various haplotype groups identified above.

Since the F508 deletion constitutes about 70% of all CF mutations, RFLP analysis may be used in supplement to the direct deletion testing for family members or close relative of CF patients. About 55% of the CF parents not carrying the F508 mutation are expected to be informative for the DNA marker JG2E1 (KH19)(Kerem at al *Am. J. Hum. Genet* 44:827–834 (1989); Estivill et al, *Genomics* 1:257 (1987)) based on retrospective analysis of our CF linkage families; an additional 39% would be informative if E6 (Taq 3)(Kerem et al supra) and J3.11 Msp I) (Wainright at al *Nature* (1985)) were also tested; virtually all parents would be informative if H2.3 (XV2C-Taq I) (Kerem et al, supra; Estivill et al, *Nature* (1987)) E2.6(E.9) (Msp I) (probe available on request) E4.1 (Mp6d.9) (Msp I) (probe available upon request; Estivill at al, *Am. J. Hum. Genet*. (1989)), J44 (E3.1) (Xba I) (probe available on request) and metD (Ban I)(Spence et al, *Am. J. Hum. Genet* (1986),(ATCC #40219) were included.

The utility of theme probes lies in the fact that they recognize polymorphic restriction sites. Thus, the probes are typically not defined by their sequence across the particular polymorphic site, but rather, can be utilized based on knowledge of flanking sequences, allowing for polymerase chain reaction (PCR) generation of the region in question, as would be known by one skilled in the art.

For example, the probe E2.6 (Mop 1) is completely defined by two flanking oligomers: 5'GTGATCCAGTTTGCTCTCCA3' (SEQ ID NO:10), and 5'GGAATCACTCTTCCTGATAT3'. (SEQ ID NO:11)

Use of this E2.6 PCR generated probe to detect an Msp I polymorphism will detect two different alleles: either one 850 bp fragment, or a 490 bp and a 360 bp fragment, depending on the presence or absence of the Map I site. Similarly, the probe J44 (E3.1) (Xba I) is completely defined by two flanking oligomers: 5'CAATGTGATTGGTGAAACTA3', (SEQ ID NO:12) and 5'CTTCTCCTCCTAGACCTGCAT3'. (SEQ ID NO:13)

Use of this J44 (E3.1) PCR generated probe to detect an Xba I polymorphism will detect two different alleles: either an 860 bp fragment or a 610 bp and a 250 bp fragment, depending on the presence or absence of the Xba I site.

The linked RFLPs may also be used in risk calculation for individuals who do not carry the F508 deletion. A general risk estimate procedure has been discussed in Beaudet et al *Am. J. Hum. Genet* 44:319–326)).

For prenatal diagnosis, microvillar intestinal enzyme analysis (Brock, *Lancet* 2: 941 (1983)) may be performed to increase the confidence of diagnosis in cases where DNA diagnosis is inconclusive.

DNA diagnosis is currently being used to assess whether a fetus will be born with cystic fibrosis, but historically this has only been done after a particular set of parents has already had one cystic fibrosis child which identifies them as obligate carriers. However, in combination with carrier detection as outlined above, DNA diagnosis for all pregnancies of carrier couples will be possible. If the parents have already had a cystic fibrosis child, an extended haplotype analysis can be done on the fetus and thus the percentage of false positive or false negative will be greatly reduced. If the parents have not already had an affected child and the DNA diagnosis on the fetus is being performed on the basis of carrier detection, haplotype analysis can still be performed.

Although it has been thought for many years that there is a great deal of clinical heterogeneity in the cystic fibrosis disease, it is now emerging that there are two general categories, called pancreatic sufficiency (CF-PS) and pancreatic insufficiency (CF-PI). If the mutations related to these disease categories are well characterized, one can associate a particular mutation with a clinical phenotype of the disease. This allows changes a in the treatment of each patient. Thus the nature of the mutation will to a certain extent predict the prognosis of the patient and indicate a specific treatment.

6.0 Molecular Biology of Cystic Fibrosis

The postulate that CFTR may regulate the activity of ion channels, particularly the outwardly rectifying C1 channel implicated as the functional defect in CF, can be tested by the injection and translation of full length in vitro transcribed CFTR mRNA in Xenopus oocytes. The ensuing changes in ion currants across the oocyte membrane can be measured as the potential is clamped at a fixed value. CFTR may regulate endogenous oocyte channels or it may be necessary to also introduce epithelial cell RNA to direct the translation of channel proteins. Use of mRNA coding for normal and for mutant CFTR, as provided by this invention, makes these experiments possible.

Other modes of expression in heterologous cell system also facilitate dissection of structure-function relationships. The complete CFTR DNA sequence ligated into a plasmid expression vector is used to transfect cells so that its influence on ion transport can be assessed. Plasmid expression vectors containing part of the normal CFTR sequence along with portions of modified sequence at selected sites can be used in vitro mutagenesis experiments performed in order to identify those portions of the CFTR protein which are crucial for regulatory function.

6.1 Expression of DNA Sequence

The DNA sequence can be manipulated in studies to understand the expression of the gone and its product, and, to achieve production of large quantities of the protein for functional analysis, antibody production, and patient therapy. The changes in the sequence may or may not alter the expression pattern in terms of relative quantities, tissue-specificity and functional properties. The partial or full-length cDNA sequences, which encode for the subject protein, unmodified or modified, may be ligated to bacterial expression vectors such as the pRIT (Nilsson et al. *EMBO J.* 4: 1075–1080 (1985)), pGEX (Smith and Johnson, *Gene* 67: 31–40 (1998)) or pATH (Spindler et al. *J. Virol.* 49: 132–141 (1984)) plasmids which can be introduced into *E. coli* cells for production of the corresponding proteins which may be isolated in accordance with the previously discussed protein purification procedures. The DNA sequence can also be transferred from its existing context to other cloning vehicles, such as other plasmids, bacteriophages, cosmids, animal virus, yeast artificial chromosomes (YAC) (Burke et al. *Science* 236: 806–812, (1987)), somatic cells, and other simple or complex organisms, such as bacteria, fungi (Timberlake and Marshall, *Science* 244: 1313–1317 (1989), invertebrates, plants (Gasser and Fraley, *Science* 244: 1293 (1989), and pigs (Pursel et al. *Science* 244: 1281–1288 (1969)).

For expression in mammalian cells, the cDNA sequence may be ligated to heterologous promoters, such as the simian virus (SV) 40, promoter in the pSV2 vector (Mulligan and Berg, *Proc. Natl. Acad. Sci USA,* 78:2072–2076 (1981) and introduced into cells, such as monkey COS-1 cells (Gluzman, *Cell,* 23:175–182 (1981) to achieve transient or long-term expression. The stable integration of the chimeric gone construct may be maintained in mammalian cells by biochemical selection, such as neomycin (Southern and Berg, *J. Mol, Appln. Genet.* 1:327–341 (1982) and mycophoenolic acid (Mulligan and Berg, supra).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it), or a mini gene (a cDNA with an intron and its own promoter) is introduced into eukaryotic expression vectors by conventional techniques. These vectors are designed to permit the transcription of the cDNA in eukaryotic calls by providing regulatory sequences that initiate and enhance the transcription of the cDNA and ensure its proper splicing and polyadenylation. Vectors containing the promoter and enhancer regions of the simian virus (SV)40 or long terminal repeat (LTR) of the Rous sarcoma virus and polyadenylation and splicing signal from SV 40 are readily available (Mulligan et al *Proc. Natl. Acad. Sci, USA* 78:1078–2076, (1981); Gorman et al *Proc Natl. Acad, Sci USA* 79: 67.77–6781 (1982)). Alternatively, the CFTR endogenous promoter may be used. The level of expression of the cDNA can be manipulated with this type of vector, either by using promoters that have different activities (for example, the baculovirus pAC373 can express cDNAs at high levels in *S. frunqiperda* cells (M. D. Summers and G. E. Smith in, Genetically Altered Viruses and the Environment (B. Fields, et al, eds.) vol. 22 no 319–328, Cold Spring Harbour Laboratory Press, Cold Spring Harbour, N.Y., 1985) or by using vectors that contain promoters amenable to modulation, for example the glucccorticoid-responsive promoter from the mouse mammary tumor virus (Lee et al, *Nature* 294:228 (1982)). The expression of the cDNA can be monitored in the recipient calls 24 to 72 hours after introduction (transient expression).

In addition, some vectors contain selectable markers such as the gpt (Mulligan et Berg supra) or neo (Southern and Berg *J. Mol. Appln. Genet* 1:327–341 (1982)) bacterial genes that permit isolation of cells, by chemical selection, that have stable, long term expression of the vectors (and therefore the cDNA) in the recipient cell. The vectors can be maintained in the cells as episomal, freely replicating entities by using regulatory elements of viruses such as papilloma (Sarver et al *Mol. Cell Biol.* 1:486 (1981)) or Epstein-Barr (Sugden et al *Mol. Cell Biol,* 5:410 (1985)). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al. *J. Biol Chem.* 253: 1357 (1978)).

The transfer of DNA into eukaryotic, in particular human or other mammalian cells is now a conventional technique. The vectors are introduced into the recipient calls as pure DNA (transfection) by, for example, precipitation with calcium phosphates (Graham and vander Eb, *Virology* 52:466 (1973)) or strontium phosphate (Brash et al *Mol. Cell Biol.* 7:2013 (1987)), electroporation (Neumann et al *EMBO J* 1:841 (1982)), lipofection (Felgner et al *Proc Natl. Acad. Sci U.S.A.* 84:7413 (1987)), DEAE dextran (McCuthan et al *J. Natl Cancer Inst.* 41:351 1968)), microinjection (Mueller et al *Cell* 15:579 1978)), protoplast fusion (Schafner, *Proc Natl. Aca. Sci U.S.A.* 72:2163) or pellet guns (Klein et al, *Nature* 327: 70 (1987)). Alternatively, the cDNA can be introduced by infect on with virus vectors. Systems are developed that use, for example, retroviruses (Bernstein et al. *Genetic Engineering* 7: 235, (1985)), adenoviruses (Ahmad et al *J. Virol* 57:267 (1986)) or Herpes virus (Spaete at al *Cell* 30:295 (1982)).

These eukaryotic expressing systems a can be used for many studies of the CF gene and the CFTR product. These include, for example: (1) determination that th gene is properly expressed and that all post-translational modifications necessary for full biological activity have been properly completed (2) identify regulatory elements located in the 5' region of the CF gene and their role in the tissue- or temporal-regulation of the expression of the CF gene (3) production of large amounts of the normal protein for isolation and purification (4) to use cells expressing the CFTR protein as an assay system for antibodies generated against the CFTR protein or an assay system to test the effectiveness of drugs, (5) study the function of the normal complete protein, specific portions of the protein, or of naturally occurring or artificially produced mutant proteins. Naturally occurring mutant proteins exist in patients with CF while artificially produced mutant protein can be designed by site directed sequence alterations. These latter studies can probe the function of any desired amino acid residue in the protein by mutating the nucleotides coding for that amino acid.

Using the above techniques, the expression vectors containing the CF gene sequence or fragments thereof can be introduced into human cells, mammalian calls from other species or non-mammalian cells as desired. The choice of cell is determined by the purpose of the treatment. For example, one can use monkey COS cells (Gluzman, *Cell* 23:175 (1981)) that produce high levels of the SV40 T antigen and permit the replication of vectors containing the SV40 origin of replication, can be used to show that the vector can express the protein, product, since function is not required. Similar treatment could be performed with Chinese hamster ovary (CHO) or mouse NIK 3T3 fibroblasts or with human fibroblasts or lymphoblasts.

The recombinant cloning vector, according to this invention, then comprises the selected DNA of the DNA sequences of this invention for expression in a suitable host. The DNA is operatively linked in the vector to an expression control sequence in the recombinant DNA molecule so that normal CFTR polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the tro system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of *E. coli, Pseudomonas, Bacillus subtilis, Bacillus stearothermophilus* or other bacili; other bacteria; yeast: fungi; insect; mouse or other animal; or plant hosts; or human tissue cells.

It is appreciated that for the mutant DNA sequence similar systems are employed to express and produce the mutant product.

6.2. Protein Function Consideration

To study the function of the CFTR protein, it is preferable to use epithelial cells as recipients, since proper functional expression may require the presence of other pathways or gene products that are only expressed in such cells. Cells that can be used include, for example, human epithelial cell lines such as T84 (ATCC #CRL 248) or PANC-1 (ATCC # CLL 1469), or the T43 immortalized CF nasal epithelium cell line (Jettan et al, *Science* (1989)) and primary (Yanhoskes et al. *Ann. Rev. Resp. Dis.* 132:1281 (1985)) or transformed (Scholte et al. *Exp. Cell. Res.* 182: 559(1989)) human nasal polyp or airways cells, pancreatic cells (Harris and Coleman *J. Call, Sci.* 87: 695 (1987)), or sweat gland cells (Collie at al. *In Vitro* 21: 597 (1985)) derived from normal or CF subjects. The CF calls can be used to test for the functional activity of mutant CF genes. Current functional assays available include the study of the movement of anions (Cl or I) across cell membranes an a function of stimulation of cells by agents that raise intracellular AMP levels and activate chloride channels (Stutto et al. *Proc. Nat. Acad. Sci. U.S.A.* 82: 6677 (1985)). Other assays include the measurement of changes in cellular potentials by patch clamping of whole calls or of isolated membranes (Frizzell et al. *Science* 233: 558 (1986), Welsch and Liedtke *Nature* 322: 467 (1986)) or the study of ion fluxes in epithelial sheets of confluent cells (Widdicombe et al. *Proc. Nat. Acad. Sci.* 82: 6167 (1985)). Alternatively, RNA made from the CF gene could be injected into *Xenopus* oocytes. The Oocyte will translate RNA into protein and allow its study. As other more specific assays are developed these can also be used in the study of transfected CFTR protein function.

"Domain-switching" experiments between CFTR and the human multidrug resistance P-glycoprotein can also be performed to further the study of the CFTR protein. In these experiments, plasmid expression vectors are constructed by routine techniques from fragments of the CFTR sequence and fragments of the sequence of P-glycoprotein ligated together by DNA ligase a that a protein containing the respective portions of theme two proteins will be synthesized by a host cell transfected with the plasmid. The latter approach has the advantage that many experimental parameters associated with multidrug resistance can be measured. Hence, it is now possible to assess the ability of segments of CFTR to influence these parameters.

These studies of the influence of CFTR on ion transport will serve to bring the field of epithelial transport into the molecular arena. This is the first transport related molecule from epithelial cells for which the complete primary structure is shown. Knowledge of CFTR can be used to better understand at a molecular level the characteristics of the epithelial cell membrane in this area. For example, the molecules in closest proximity to CFTR can be determined by cross-linking experiments. The hypothesis that the role of CFTR is to regulate ion channels would predict that these channels would necessarily fall into that category. The large, high quality cDNA libraries constructed for the cloning of CFTR cDNAs will also be useful for the molecular cloning of cDNAs for polypeptides constituting other epithelial ion transport systems, including other channels as well as co-, counter-, and active-transport systems.

6. Therapies

It in understood that the major aim of the various biochemical studies using the compositions of this invention is the development of therapies to circumvent or overcome the CF defect, using both the pharmacological and the "gene-therapy" approaches.

In the pharmacological approach, drugs which circumvent or overcome the FF defect are sought. Initially, compounds may be tested essentially at random, and screening systems are required to discriminate among many candidate compounds. This invention provides host cell systems, expressing various of the mutant CF genes, which are particularly well suited for use as first level screening systems. Preferably, a cell culture system using mammalian calls (most preferably human cells) transfected with an expression vector comprising a DNA sequence coding for CFTR protein containing a CF-generating mutation, for example the F508 deletion, is used in the screening process. Candidate drugs are tested by incubating the calls in the presence of the candidate drug and measuring those cellular functions dependent on CFTR, especially by measuring ion currents where the transmembrane potential is clamped at a fixed value. To accommodate the large number of assays, however, more convenient assays are based, for example, on the use of ion-sensitive fluorescent dyes. To detect changes in Cl⁻ion concentration SPQ or its analogues are useful.

Alternatively, a cell-free system could be used. Purified CFTR could be reconstituted into artificial membranes and drugs could be screened in a cell-free assay (Al-Aqwatt, *Science*, (1989)).

At the second level, animal testing is required. It is possible to develop a model of CF by interfering with the normal expression of the counterpart of the CF gene in an animal such as the mouse. The "knock-out" of this gene by introducing a mutant form of it into the germ line of animals will provide a strain of animals with CF-like syndromes. This enables testing of drugs which showed a promise in the first level call-based screen.

As further knowledge is gained about the nature of the protein and its function, it will be possible to predict structures of proteins or other compounds that interact with the CFTR protein. That in turn will allow for certain predictions to be made about potential drugs that will interact with this protein and have some effect on th treatment of the patients. Ultimately such drugs may be designed and synthesized chemically on the basis of structures predicted to be required to interact with domains of CFTR. This approach is reviewed in Capsey and Delvatte, *Genetically Engineered Human Therapeutic Drugs* Stockton Press, New York, 1988. These potential drugs must also be tested in the screening system.

6.3.1 Protein Replacement Therapy

Treatment of CF can be performed by replacing the defective protein with normal protein, by modulating the function of the defective protein or by modifying another step in the pathway in which CFTR participates in order to correct the physiological abnormality.

To be able to replace the defective protein with the normal version, one must have reasonably large amounts of pure CFTR protein. Pure protein can be obtained as described earlier from cultured cell systems. Delivery of the protein to the affected airways tissue will require its packaging in lipid-containing vesicles that facilitate the incorporation of the protein into the call membrane. It may also be feasible to use vehicles that incorporate proteins such as surfactant protein, such as SAP(Val) or SAP(Phe) that performs this function naturally, at least for lung alveolar cells. (PCT Patent Application WO/8803170, Whitsett at al, May 7, 1988 and PCT Patent Application WO89/04327, Benson et al, May 18, 1989). The CFTR-containing vesicles are introduced into the airways by inhalation or irrigation, techniques that are currently used in CF treatment (Boat et al, supra).

6.3.2 Drug Therapy

Modulation of CFTR function can be accomplished by the use of therapeutic agents (drugs). These can be identified by random approaches using a screening program in which their effectiveness as in modulating the defective CFTR protein is monitored in vitro. Screening programs can use cultured cell systems in which the defective CFTR protein is expressed. Alternatively, drugs can be designed to modulate CFTR activity from knowledge of the structure and function correlations of CFTR protein and from knowledge of the specific defect in the various CFTR mutant proteins (Capsey and Delvatte, supra). It is possible that each mutant CFTR protein will require a different drug for specific modulation. It will then be necessary to identify the specific mutations) in each CF patient before initiating drug therapy.

Drugs can be designed to interact with different aspects of CFTR protein structure or function. For example, a drug (or antibody) can bind to a structural fold of the protein to correct a defective structure. Alternatively, a drug might bind to a specific functional residue and increase its affinity for a substrate or cofactor. Since it is known that members of the class of proteins to which CFTR has structural homology can interact, bind and transport a variety of drugs, it is reasonable to expect that drug-related therapies may be effective in treatment of CF.

A third mechanism for enhancing the activity of an effective drug would be to modulate the production or the stability of CFTR inside the cell. This increase in the amount of CFTR could compensate for its defective function.

Drug therapy can also be used to compensate for the defective CFTR function by interactions with other components of the physiological or biochemical pathway necessary for the expression of the CFTR function. These interactions can lead to increases or decreases in the activity of these ancillary proteins. The methods for the identification of these drugs would be similar to those described above for CFTR-related drugs.

In other genetic disorders, it has been possible to correct for the consequences of altered or missing normal functions by use of dietary modifications. This has taken the form of removal of metabolites, as in the case of phenylketonuria, where phenylalanine is removed from the diet in the first five years of life to prevent mental retardation, or by the addition of large amounts of metabolites to the diet, as in the case of adenosime deaminase deficiency where the functional correction of the activity of the enzyme can be produced by the addition of the enzyme to the diet. Thus, once the details of the CF function have been elucidated and the basic defect in CF has been defined, therapy may be achieved by dietary manipulations.

The second potential therapeutic approach is so-called "gene-therapy" in which normal copies of the CF gene are introduced in to patients so as to successfully code for normal protein in the key epithelial calls of affected tissues. It is most crucial to attempt to achieve this with the airway epithelial cells of the respiratory tract. The CF gene is delivered to these cells in a form in which it can be taken up and code for sufficient protein to provide regulatory function. As a result, the patient's quality and length of life will be greatly extended. Ultimately, of course, the aim is to deliver the gene to all affected tissues.

6.3.3 Gene Therapy

One approach to therapy of CF is to insert a normal version of the CF gene into the airway epithelium of affected patients. It is important to note that the respiratory system is the primary cause of mordibity and mortality in CF; while pancreatic disease is a major feature, it is relatively well treated today with enzyme supplementation. Thus, somatic cell gene therapy (for a review, see T. Friedmann, *Science* 244:1275 (1989)) targeting the airway would alleviate the most severe problems associated with CF.

A. Retroviral Vectors. Retroviruses have been considered the preferred vector for experiments in somatic gene therapy, with a high efficiency of infection and stable integration and expression (Orkin et al *Prog. Med. Genet* 7;130, (1988)). A possible drawback is that cell division is necessary for retroviral integration, so that the targeted cells in the airway may have to be nudged into the cell cycle prior to retroviral infection, perhaps by chemical means. The full length CF gene cDNA can be cloned into a retroviral vector and driven from either its endogenous promoter or from the retroviral LET (long terminal repeat). Expression of levels of the normal protein as low as 10% of the endogenous mutant protein in CF patients would be expected to be beneficial, since this is a recessive disease. Delivery of the virus could be accomplished by aerosol or instillation into the trachea.

B. Other Viral Vectors. Other delivery systems which can be utilized include adeno-associated virus (AAV, McLaughlin et al *J. Virol* 62:1963 (1988)), vaccinia virus [Moss et al *Annu. Rev. Immunol,* 5:305, 1987)), bovine papilloma virus (Rasmussen et al, *Methods Enzymol* 139:642 (1987)) or member of the herpesvirus group such as Epstein-Barr virus (Margolskee et al *Mol. Cell. Biol* 8:2973 (1988)). Though much would need to be learned about their basic biology, the idea of using a viral vector with natural tropism for the respiratory tree (e.g. respiratory syncytial virus, echovirus, Coxsackie virus, etc.) is possible.

C. Non-viral Gene Transfer. Other methods of inserting the CF gone into respiratory epithelium may also be productive; many of these are lower efficiency and would potentially require infection in vitro, selection of transfectants, and reimplantation. This would include calcium phosphate, DEAE dextran, electroporation, and protoplast fusion. A particularly attractive idea is the use of liposome, which might be possible to carry out in vivo (Ostro, *Liposomes*, Marcel-Dekker, 1987)). Synthetic cationic lipids such as DOTMA (Felger et al *Proc. Natl. Acad. Sci USA* 84:7413 (1987)) may increase the efficiency and ease of carrying out this approach.

6.4 CF Animal Models

The creation of a mouse or other animal model for CF will be crucial to understanding the disease and for testing of possible therapies (for general review of creating animal models, see Erickson, *Am. J. Hum. Genet* 43:582 (1988). Currently no animal model of the CF exists. The evolutionary conservation of the CF gene (as demonstrated by the cross-species hybridization blots for E4.3 and H1.6), as is shown in FIGS. 4A–4D, indicate that an orthologous gene exists in the mouse (hereafter to be denoted mCFTR, and its corresponding protein as mCFTR), and this will be possible to clone in mouse genomic and cDNA libraries using the human CF gene probes. It is expected that the generation of a specific mutation in the mouse gene analogous to the F508 mutation will be most optimum to reproduce the phenotype, though complete inactivation of the mCFTR gene will also be a useful mutant to generate.

A. *Mutagenesis.* Inactivation of the mCF gene can be achieved by chemical (e.g. Johnson at al *Proc. Natl. Aced. Sci. USA* 78:3138 (1981) or X-ray mutagenesis (Popp et al *J. Mol. Biol.* 127:141 (1979)) of mouse gametes, followed by fertilization. Offspring heterozygous for inactivation of mCFTR can then be identified by Southern blotting to demonstrate loss of one allele by dosage, or failure to inherit one parental allele if an RFLP marker is being assessed. This approach has previously been successfully used to identify mouse mutants for α-globin (Whitney et al *Proc. Natl. Acad. Sci. USA* 77:1087 (1980)) phenylalanine hydroxylase (McDonald et al *Pediatr, Res* 23:63 (1988)), and carbonic anhydrase II (Lewis et al *Proc. Natl. Acad. Sci. USA* 85:1962, (1988)).

B. Transgenic A normal or mutant version of CFTR or mCFTR can be inserted into the mouse germ line using now standard techniques of oocyte injection (Camper, *Trends in Genetics* (1988)); alternatively, if it is desirable to inactivate or replace the endogenous mCF gene, the homologous recombination system using embryonic stem (ES) cells (Capecchi, *Science* 244:1288 (1989)) may be applied.

1. Oocyte Injection Placing one or more copies of the normal or mutant mCF gene at a random location in the mouse germline can be accomplished by microinjection of the pronucleus of a just-fertilized mouse oocyte, followed by reimplantation into a pseudo-pregnant foster mother. The liveborn mice can then be screened for integrants using analysis of tail DNA for the presence of human CF gene sequences. The same protocol can be used to insert a mutant mCF gene. To generate a mouse model, one would want to place this transgene in a mouse background where the endogenous mCF gene has been inactivated, either by mutagenesis (see above) or by homologous recombination (see below). The transgene can be either: a) a complete genomic sequence, though the size of this (about 250 kb) would require that it be injected as a yeast artificial chromosome or a chromosome fragment; b) a cDNA with either the natural promoter or a heterologous promoter; c) a "minigene" containing all of the coding region and various other elements such as introns, promoter, and 3' flanking elements found to b necessary for optimum expression.

2. Retroviral Infection of Early Embryos. This alternative involves inserting the CFTR or mCF gene into a retroviral vector and directly infecting mouse embroyos at early stages of development generating a chimera (Soriano et al *Cell* 46:19 (1986)). At least some of these will lead to germline transmission.

3. ES Cells and Homologous Recombination.

The embryonic stem cell approach (Capecchi, supra and Capecchi, *Trends Genet* 5:70 (1989)) allows the possibility of performing gene transfer and then screening the resulting totipotent cells to identify the rare homologous recombination events. Once identified, these can be used to generate chimeras by injection of mouse blastocysts, and a proportion of the resulting mice will show germline transmission from the recombinant line. There are several ways this could be useful in the generation of a mouse model for CF:

a) Inactivation of the mCF gene can be conveniently accomplished by designing a DNA fragment which contains sequences from a mCFTR exon flanking a selectable marker such as neo. Homologous recombination will lead to insertion of the neo sequences in the middle of an exon, inactivating mCFTR. The homologous recombination events (usually about 1 in 1000) can be recognized from the heterologous ones by DNA analysis of individual clones (usually using PCR, Kim et al *Nucleic Acids Res.* 16:8887 (1988), Joyner et al *Nature* 338:153 (1989); Zimmer et al supra, p. 150) or by using a negative selection against the heterologous event (such as the use of an HSV TK gene at the end of the construct, followed by the gancyclovir selection, Mansour et al, *Nature* 336:348 (1988)). This inactivated mCFTR mouse can then be used to introduce a mutant CF gene or mCF gene containing the F508 abnormality or any other desired mutation.

b) It is possible that specific mutants of mCFTR DNA be created in one step. For example, one can make a construct containing mCF intron 9 sequences at the 5' end, a selectable neo gene in the middle, and intro 9+exon 10 (containing the mouse version of the F508 mutation) at the 3' end. A homologous recombination event would lead to the insertion of the neo gene in intron 9 and the replacement of exon 10 with the mutant version.

c) If the presence of the selectable neo marker in the intron altered expression of the mCF gene, it would be possible to excise it in a second homologous recombination step.

d) It is also possible to create mutations in the mouse germline by injecting oligonucleotides containing the mutation of interest and screening the resulting cells by PCR.

This embodiment of the invention has considered primarily a mouse model for cystic fibrosis. FIGS. 4A–4D shows cross-species hybridization not only to mouse DNA, but also to bovine, hamster and chicken DNA. Thus, it is contemplated that an orthologous gene will exist in many other species also. It is thus contemplated that it will be possible to generate other animal models using similar technology.

Although preferred embodiments of the invention have been described herein in detail, it will be understood by those skilled in the art that variations may be made thereto without departing from the spirit of the invention or the scope of the appended claims.

We claim:

1. A recombinant vector containing a purified DNA molecule comprising a normal cystic fibrosis transmembrane conductance regulator (CFTR) DNA sequence encoding an amino acid sequence depicted in FIGS. 1A–1H selected from the group consisting of amino acid positions:
   (a) 28 to 45;
   (b) 58 to 75;
   (c) 104 to 117;
   (d) 139 to 153;
   (e) 204 to 249;
   (f) 279 to 294;
   (g) 347 to 698;
   (h) 500 to 512;
   (i) 710 to 757;
   (l) 725 to 739;
   (k) 758 to 796;
   (l) 933 to 946;
   (m) 1066 to 1084; and
   (n) 1188 to 1480.

2. A recombinant cloning vector containing a purified DNA molecule comprising a mutant CFTR DNA sequence selected from the group consisting of:
   (a) a mutant DNA sequence encoding a mutant CFTR protein having the amino acid sequence depicted in FIGS. 1A–1H, wherein said DNA sequence contains at least one cystic fibrosis (CF) mutation;
   (b) a mutant DNA sequence which hybridizes under stringent conditions to at least 16 contiguous nucleotides of the DNA coding sequence depicted in FIG. 1, said DNA sequence containing said at least one CF mutation; and
   (c) a mutant DNA sequence complementary to the mutant DNA sequence of (a) or (b);

wherein said CF mutation includes at least one of a nucleotide substitution, deletion or insertion, of or to the DNA sequence of FIGS. 1A–1H; and wherein said mutant DNA sequence of (a), (b) or (c), when present as part of a coding sequence of a mutant CFTR gene, is expressed in human epithelial cells and is characterized as having cystic fibrosis associated activity.

3. A recombinant vector according to claim 2, wherein said purified DNA molecule is cDNA.

4. A recombinant vector according to claim 2, wherein said CF mutation is a F508 mutation which comprises a three base pair deletion of a DNA sequence encoding a phenylalanine corresponding to amino acid position 508 of a normal CFTR protein.

5. A recombinant vector according to claim 2, wherein said DNA molecule is operatively linked to an expression control sequence in said recombinant cloning vector so that a mutant normal CFTR polypeptide can be expressed, said expression control sequence being selected from the group consisting of sequences that control the expression of genes of prokaryotic or eukaryotic cells and their viruses, or combinations thereof.

6. A recombinant vector according to claim 5, wherein the expression control sequence is selected from the group consisting of a lac system, a trp system, a tac system, a trc system, a major operator and promoter region of a phage lambda, a control region of fd coat protein, an early or late promoter of SV40, a promoter derived from a polyoma, an adenovirus, a retrovirus, a baculovirus or a simian virus, a promoter for 3-phosphoglycerate kinase, a promoter of yeast acid phosphatase, a promoter of a yeast alpha-mating factor and combinations thereof.

7. A recombinant vector according to claim 2, wherein said mutant DNA sequence comprising the protein coding sequence of FIGS. 1A–1H, wherein said mutant DNA sequence contains said at least one CF mutation.

8. A host cell transformed with a recombinant cloning vector according to claim 2.

9. A host cell according to claim 8, wherein said host cell is a bacterial cell.

10. A host cell according to claim 9, wherein said host cell is of a strain of a bacteria selected from the group consisting of *E. coli, Pseudomonas, Bacillus subtilis,* and *Bacillus stearothermophilus.*

11. A host cell according to claim 8, wherein said host cell is a eukaryotic cell.

12. A host cell according to claim 11, wherein said host cell is derived from an organism selected from the group consisting of a yeast; a fingi; an insect; a non-human animal; a plant host; or human tissue cells.

13. A host cell according to claim 12, wherein said human tissue cells are human epithelial cells.

14. A method for producing a mutant CFTR polypeptide, comprising
   (a) culturing a host cell according to claim 8 in a medium and under conditions favorable for expression of said mutant CFTR polypeptide in recoverable amounts; and
   (b) isolating the expressed mutant CFTR polypeptide.

* * * * *